United States Patent
Møller et al.

(10) Patent No.: US 10,415,066 B2
(45) Date of Patent: Sep. 17, 2019

(54) USE OF OCTAKETIDE SYNTHASES TO PRODUCE KERMESIC ACID AND FLAVOKERMESIC ACID

(71) Applicants: Danmarks Tekniske Universitet, Lyngby (DK); Københavns Universitet, København K (DK)

(72) Inventors: Birger Lindberg Møller, Brønshøj (DK); Bjørn Madsen, Helsingør (DK); Dan Stærk, Lynge (DK); Finn Thyge Okkels, Roskilde (DK); Johan Andersen-Ranberg, Berkeley, CA (US); Kenneth Thermann Kongstad, København V (DK); Kim Binderup, Charlottenlund (DK); Mads Bennedsen, Græsted (DK); Majse Nafisi, Vanløse (DK); Paiman Khorsand-Jamal, Kgs. Lyngby (DK); Rubini Maya Kannangara, Frederiksberg (DK); Uffe Hasbro Mortensen, København N (DK); Ulf Thrane, Helsinge (DK); Rasmus John Normand Frandsen, Allerød (DK)

(73) Assignees: Danmarks Tekniske Universitet, Lyngby (DK); Københavns Universitet, København K (DK)

( * ) Notice: Subject to any disclaimer, the term of this patent is extended or adjusted under 35 U.S.C. 154(b) by 53 days.

(21) Appl. No.: 15/735,051

(22) PCT Filed: Jun. 10, 2016

(86) PCT No.: PCT/EP2016/063242
§ 371 (c)(1),
(2) Date: Dec. 8, 2017

(87) PCT Pub. No.: WO2016/198564
PCT Pub. Date: Dec. 15, 2016

(65) Prior Publication Data
US 2019/0127767 A1 May 2, 2019

(30) Foreign Application Priority Data
Jun. 10, 2015 (EP) ..................... 15171375

(51) Int. Cl.
*C12P 7/66* (2006.01)
*C12N 9/00* (2006.01)
*C12P 19/18* (2006.01)
*C12N 9/10* (2006.01)

(52) U.S. Cl.
CPC .............. *C12P 7/66* (2013.01); *C12N 9/1048* (2013.01); *C12N 9/93* (2013.01); *C12P 19/18* (2013.01)

(58) Field of Classification Search
None
See application file for complete search history.

(56) References Cited

U.S. PATENT DOCUMENTS 5,424,421 A 6/1995 Tyman et al.

FOREIGN PATENT DOCUMENTS

WO WO 2004/111254 A1 12/2004
WO WO 2006/056585 A1 6/2006

OTHER PUBLICATIONS

Abe, Ikuro et al., "Engineered Biosynthesis of Plant Polyketides: Chain Length Control in an Octaketide-Producing Plant Type III Polyketide Synthase" J. Am. Chem. Soc., 2005, pp. 12709-12716, vol. 127.
Baig, Irfan et al., "On the Acceptor Substrate of C-Glycosyltransferase UrdGT2: Three Prejadomycin C-Glycosides from an Engineered Mutant of *Streptomyces globisporus* 1912 ΔlndE(urdGT2)" Angew. Chem. Int. Ed., 2006, pp. 7842-7846, vol. 45.
Genta, Fernado A. et al., "Potential role for gut microbiota in cell wall digestion and glucoside detoxification in Tenebrio molitor larvae" Journal of Insect Physiology, 2006, pp. 593-601, vol. 52.
Geuder, Martina et al., "Sequestration and Metabolism of Host-Plant Flavonoids by the Lycaenid Butterfly" Journal of Chemical Ecology, 1997, pp. 1361-1372, vol. 23, No. 5.
Gutmann, Alexander et al., "Enzymatic C-glycosylation: Insights from the study of a complementary pair of plant O- and C-glucosyltransferases" Pure Appl. Chem., 2013, pp. 1865-1877, vol. 85, No. 9.
Hansen, Esben Halkjær et al., "Substrate specificities of family 1 UGTs gained by domain swapping" Phytochemistry, 2009, pp. 473-482, vol. 70.
Jadhav, Supriya et al., "Polyketide synthesis in tobacco plants transformed with a Plumbago zeylanica type III hexaketide synthase" Phytochemistry, 2014, pp. 92-100, vol. 98.
Karppinen, Katja et al., "Octaketide-producing type III polyketide synthase from Hypericum perforatum is expressed in dark glands accumulating hypericins" FEBS Journal, 2008, pp. 4329-4342, vol. 275.
Mizuuchi, Yuusuke et al., "Novel type III polyketide synthases from Aloe arborescens" FEBS Journal, 2009, pp. 2391-2401, vol. 276.
Osmani, Sarah A. et al., "Catalytic Key Amino Acids and UDP-Sugar Donor Specificity of a Plant Glucuronosyltransferase, UGT94B1: Molecular Modeling Substantiated by Site-Specific Mutagenesis and Biochemical Analyses" Plant Physiology, Nov. 2008, pp. 1295-1308, vol. 148.

(Continued)

*Primary Examiner* — Suzanne M Noakes
*Assistant Examiner* — Jae W Lee
(74) *Attorney, Agent, or Firm* — Knobbe Martens Olson & Bear LLP

(57) ABSTRACT

A method for producing an octaketide derived aromatic compound of interest (e.g. carminic acid), wherein the method comprises (I): heterologous expression of a recombinantly introduced Type III polyketide synthase (PKS) gene encoding an octaketide synthase (OKS) to obtain non-reduced octaketide in vivo within the recombinant host cell and (II): converting in vivo the non-reduced octaketide of step (I) into a $C_{14}$-$C_{34}$ aromatic compound of interest (e.g. carminic acid).

15 Claims, 4 Drawing Sheets

Figure 1:
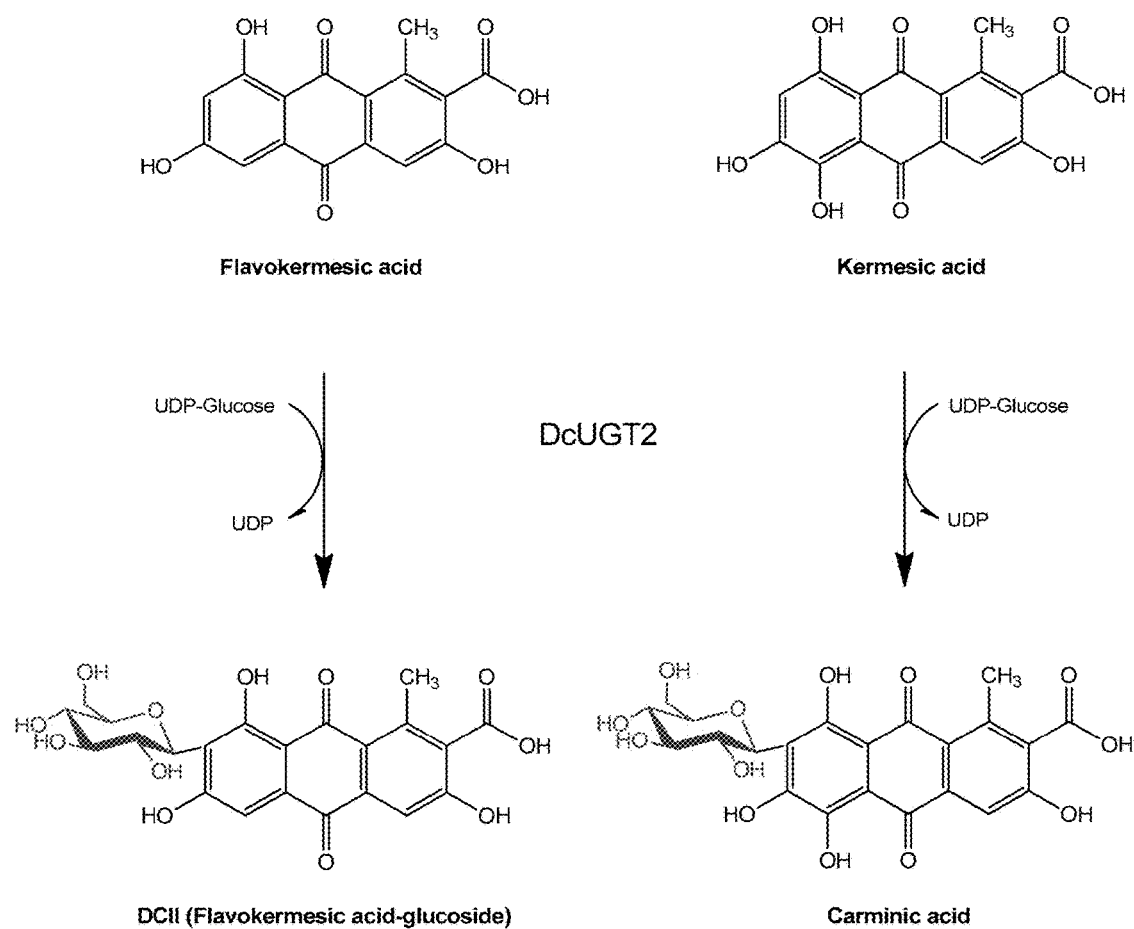

Specification includes a Sequence Listing.

(56) References Cited

OTHER PUBLICATIONS

Radominska-Pandya, Anna et al., "The crystal structure of human UDP-glucuronosyltransferase 2B7 C-terminal end is the first mammalian UGT target to be revealed: the significance for human UGTs from both the 1A and 2B families" Drug Metabolism Reviews, 2010, pp. 133-144, vol. 42, No. 1.
Stathopoulou, Konstantina et al., "Structure elucidation and chromatographic identification of anthraquinone components of cochineal (Dactylopius coccus)detected in historical objects" Analytica Chimica Acta, 2013, pp. 264-272, vol. 804.
Tang, Yi et al., "Engineered Biosynthesis of Regioselectively Modified Aromatic Polyketides Using Bimodular Polyketide Synthases" PLoS Biology, Feb. 2004, pp. 0227-0238, vol. 2, Issue 2.
Yu, Dayu et al., "Type III Polyketide Synthases in Natural Product Biosynthesis" IUBMB Life, Apr. 2012, pp. 285-295, vol. 64, No. 4.
Zagrobelny, Mika et al., "Cyanogenic glucosides and plant-insect interactions" Phytochemistry, 2004, pp. 293-306, vol. 65.
European Search Report for EP 15171375 dated Dec. 22, 2015.
International Search Report for PCT/EP2016/063242 dated Jul. 29, 2016.

9,10-anthraquinone skeleton

Anthrone

FK antrone

USE OF OCTAKETIDE SYNTHASES TO PRODUCE KERMESIC ACID AND FLAVOKERMESIC ACID

CROSS REFERENCE TO RELATED APPLICATIONS

This application is a U.S. National Phase Application of PCT International Application Number PCT/EP2016/063242, filed on Jun. 10, 2016, designating the United States of America and published in the English language, which is an International Application of and claims the benefit of priority to European Patent Application No. 15171375.7, filed on Jun. 10, 2015. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-PLOUG227-002APC.txt, the date of creation of the ASCII text file is Nov. 28, 2017, and the size of the ASCII text file is 93 KB.

FIELD OF THE INVENTION

The present invention relates to a method for producing an octaketide derived aromatic compound of interest (e.g. carminic acid), wherein the method comprises (I): heterologous expression of a recombinantly introduced Type III polyketide synthase (PKS) gene encoding an octaketide synthase (OKS) to obtain non-reduced octaketide in vivo within the recombinant host cell and (II): converting in vivo the non-reduced octaketide of step (I) into a $C_{14}$-$C_{34}$ aromatic compound of interest (e.g. carminic acid).

BACKGROUND OF THE INVENTION

The natural pigment carminic acid is one of the most frequently used colorants of food, medicine, cosmetics and textiles.

Carminic acid is a colorant, which can be extracted from the female insect bodies of *Dactylopius coccus costa* (alternative name *Coccus cacti* L.). The insects live on *Nopalea coccinellifera*, *Opuntia fidus* indica and other plants of the family Cactaceae cultivated for instance in the desert areas of Mexico, Central and South America and Canary Islands. Depending on the pH the colorant may be a color in a spectrum from orange over red to purple and is generally known as cochineal or cochineal color. Carmine colorant is widely used in foods and beverages.

As known in the art *Porphyrophora polonica* is also producing carminic acid and was cultured for production of carminic acid in e.g. Poland.

In relation to current industrial relevant production, carminic acid is harvested by extraction from the insect's dried bodies with water or alcohol.

In order to try to resolve the problem of undesirable variations and price fluctuations—U.S. Pat. No. 5,424,421 (European Colour, published 1995) describes chemical synthesis of carminic acid by a route of synthesis involving different intermediates.

As discussed in e.g. WO2006/056585A1 (Chr. Hansen A/S), during the aqueous based extraction of carminic acid from the insect, an amount of insect protein is also released from the insect and will be contained in the color extract and it has been reported that the cochineal insect proteins could create some allergy related problems. In WO2006/056585A1 a special process to reduce the amount of insect protein from the insect extract solution is described. However, the final produced color composition/product of WO2006/056585A1 will still comprise some amounts *Dactylopius coccus costa* insect proteins.

The structure of carminic acid is shown in FIG. 1 herein. As can be seen from the Figure, it is a so-called C-glucoside (i.e. wherein the glucose is joined/conjugated to the aglucon by a carbon-carbon linkage).

As shown in FIG. 1 herein, hydrolysis of the C-glucoside carminic acid can give glucose and the aglucon kermesic acid (KA).

The in vivo biosynthetic pathway of carminic acid in the insect (*Dactylopius coccus*) is currently not described in details. Accordingly, based on the prior art the skilled person does not know which compound is the aglucon during the in vivo biosynthetic production of carminic acid in *Dactylopius coccus*.

Analysis of *Dactylopius coccus* has shown that a broad range of compounds related to carminic acid are present in extracts from *Dactylopius coccus* and numerous of these compounds could in principle be glucosylated during the in vivo biosynthetic production of carminic acid.

For instance, in the article of Stathopoulou et al. (Analytica Chimica Acta 804 (2013) 264-272) six new anthraquinones were described in an extract from *D. coccus* and any of these six new anthraquinones (see e.g. FIG. 1 of the article) could in principle be the molecule which is glucosylated during the in vivo biosynthetic production of carminic acid in *Dactylopius coccus*. Further, as known in the art the primary glucosylated compound formed during the in vivo biosynthetic production of the glucoside end product may be an unstable intermediate compound that will not be identified in an isolated extract from *Dactylopius coccus* as e.g. analyzed in the above discussed article of Stathopoulou et al.

As understood by the skilled person in the present context, based on the prior art, it could be speculated that a relevant primary glucosylated compound during the in vivo biosynthetic production of carminic acid in *Dactylopius coccus* could e.g. be an unstable intermediate polyketide compound with around the same number of carbon atoms as e.g. flavokermesic acid.

A herein relevant DNA or amino acid sequence of a glycosyltransferase involved in the in vivo insect (*Dactylopius coccus*) biosynthetic pathway of carminic acid is not explicitly described in the prior art.

As known in the art, for insects that accumulate low molecular weight chemicals the relevant biosynthetic pathway genes are sometimes not present in the insect genome. For instance, some insects take up glycosides from the plants they feed on—see e.g. the article of Zagrobelny et al (Cyanogenic glucosides and plant-insect interactions; Phytochemistry. 2004 February; 65(3):293-306) or the article of Geuder et al (Journal of Chemical Ecology, Vol. 23, No. 5, 1997).

*Dactylopius coccus* insects feed on cactus plants and it could be that *Dactylopius coccus* insects (like other insects) take up relevant glycosides from the cacti they feed on. As known in the art, for insects that accumulate low molecular weight glycosides, the relevant biosynthetic pathway genes are sometimes found in the microorganisms living in the insects, see e.g. the article of Genta et al. (Potential role for gut microbiota in cell wall digestion and glucoside detoxification in *Tenebrio molitor* larvae), Journal of Insect Physiology 52 (2006) 593-601.

Accordingly, based on the prior art the skilled person could not know if the genome of *Dactylopius coccus* actually would comprise a gene encoding a glycosyltransferase involved in the in vivo biosynthetic pathway leading to carminic acid.

Polyketides are synthesized by a group of enzymes which commonly is referred to as polyketide synthases (PKS). All PKSs share the ability to catalyze Claisen condensation based fusion of acyl groups by the formation of carbon-carbon bonds with the release of carbon dioxide. This reaction is catalyzed by a beta-ketosynthase domain (KS). In addition to this domain/active site, synthesis can also depend on, but not exclusively, the action of Acyl-Carrier-Protein (ACP), Acyl-transferase (AT), Starter-Acyl-Transferase (SAT), Product Template (PT), ThioEsterase (TE), Chain Length Factor (CLF, also known as KSβ), Claisen CYClase (CYC), Ketoreductase (KR), dehydratase (DH), enoyl reductase (ER) and C-methyl transferase (Cmet). The substrates for polyketide synthesis are typically classified into starter and extender units, where the starter unit, including but not limited to acetyl-CoA is the first added unit of the growing polyketide chain; and extender units, e.g. but not exclusively malonyl-CoAs, are all subsequently added carbon-carbon units. At the primary sequence level (amino acid sequence), secondary structure level (local fold), tertiary structure level (all over fold) and quaternary structure level (protein-protein interactions) the PKSs display a very large diversity, and are hence subdivided into different types.

Type I PKS systems are typically found in filamentous fungi and bacteria, where they are responsible for both the formation of aromatic, polyaromatic and reduced polyketides. Members of the type I PKS possess several active sites on the same polypeptide chain and the individual enzyme is able to catalyze the repeated condensation of two-carbon units. The minimal set of domains in type I PKS includes KS, AT and ACP. The type I PKSs is further subdivided into modular PKSs and iterative PKSs, where iterative PKSs only possess a single copy of each active site type and reuse these repeatedly until the growing polyketide chain has reached its predetermined length. Type I iterative PKS that forms aromatic and polyaromatic compounds typically rely on the PT and CYC domain to direct folding of the formed non-reduced polyketide chain. Modular PKSs contain several copies of the same active sites, these are organized into repeated sequences of active sites which are called modules, each module is responsible for adding and modifying a single ketide unit. Each active site in the individual modules is only used once during synthesis of a single polyketide. Type I iterative PKS are typically found in fungi, while type I modular PKSs are typically found in bacteria.

Type II PKS systems are responsible for formation of aromatic and polyaromatic compounds in bacteria.

Type II PKSs are protein complexes where individual enzymes interact to form the functional PKS enzyme. The individual enzymes include activities for KS, CLF and ACP. This type of PKS is characterized by being composed of multiple different enzymes that form a protein complex, which collectively is referred to as an active PKS. The type II PKSs form non-reduced polyketides that spontaneously folds into complex aromatic/cyclic compounds. However, in the bacterial systems folding of polyketide backbones is most often assisted/directed by different classes of enzymes, that act in trans (independent of the PKS enzyme) to promote a non-spontaneous fold. The involved enzyme classes are referred to as aromatases and cyclases. The biosynthesis of a single polyaromatic compound in these systems typically involves the successive action of multiple different aromatases/cyclases. The aromatases and cyclases can be divided into two groups based on which types of substrates they act on: where the first group only acts on linear polyketide chains and catalyzes formation of the first aromatic/cyclic group, the second group of enzymes only accepts substrates that include aromatic or cyclic groups (=products from the first group of aromatases/cyclases). It has proven impossible to functionally express type II PKS systems in a suitable production host (*E. coli*, *Bacillus*, yeast), likely due to the fact that these are multienzyme complexes which require a balanced expression level, and which may rely on unknown factors.

Type III PKSs generally only consist of a KS domain, which in the literature may e.g. be referred to as a KASIII or a Chalcone synthase domain that acts independently of the ACP domain. Type III PKS from bacteria, plant and fungi have been described.

Type III PKSs have long been known in plants, where they are responsible for formation of compounds such as flavonoids (pigments/anti-oxidants) and stilbenes, which are found in many different plant species. The products of type III PKSs often spontaneously folds into complex aromatic/cyclic compounds.

The article of Yu et al. (2012) provides a review of Type III Polyketide synthases in natural product biosynthesis. The Yu et al. (2012) article reads: "Type III PKSs are selfcontained enzymes that form homodimers. Their single active site in each monomer catalyzes the priming, extension, and cyclization reactions iteratively to form polyketide products. Despite their structural simplicity, type III PKSs produce a wide array of compounds such as chalcones, pyrones, acridones, phloroglucinols, stilbenes, and resorcinolic lipids. In recent years, type III PKSs have drawn more attention due to their diverse products, wide distribution, relatively simple structures, and easy genetic manipulability. In this article, we will systematically discuss type III PKSs from plants, bacteria, and fungi as well as the recent progress in the type III PKS research."

In short, based on the prior art, the skilled person knows if a specific PKS of interest is a Type I, Type II or Type III PKS.

In addition to the protein structural and functional based classification of PKS systems, an alternative classification is based on the level of modifications found in the final polyketide product. Note that these modifications can either be introduced by the PKS itself or by post-acting enzymes. In this classification scheme the products are divided into two groups: (I) non-reduced and (II) reduced polyketides. The non-reduced type is characterized by the presence of ketone groups in the ketides (—CH2-CO—), originating from the starter or extender units, either as ketones or in the form of double bonds in aromatic groups. In reduced polyketides a single or all ketones have been reduced to alcohol (—CH2-CHOH—) groups by a KR domain/enzyme, or further to an alkene group (—C=C—) by a DH domain/enzyme, or even further to an alkane group (—CH2-CH2-) by an ER domain/enzyme. Based on these chemical features of the formed products the involved PKSs are categorized as either being a non-reducing PKS or a reducing PKS.

Folding of the formed polyketide chain into complex structures with cyclic motifs is typically a post-PKS enzyme guided and catalyzed process. The responsible enzymes belong to several different enzyme families, typically aromatases and/or cyclases. Fungal Type I iterative PKSs are special by posing a PT domain which is responsible for the formation of aromatic rings while CYC domains are responsible for product release coupled to formation of aromatic rings. The aromatases and cyclases acting on polyketides have been described from bacterial and plant systems. In addition, several examples exist where folding of the polyketide is a spontaneous process, e.g. flavonoids in plants.

PKSs have been isolated and functionally characterized from bacteria, fungi and plants. However, no PKS of animal origin has been described, and synthesis of polyketides in insects has in several instances been linked to the metabolic activity of endosymbiotic bacteria.

The article of Tang, Y. et al. (2004) describes that expression in the bacteria Streptomyces coelicolor CH999 strain, which contains chromosomal deletion affecting the entire Act gene cluster responsible for actinorhodin biosynthesis. The mini PKS (Act PKS=Act KS, Act CLF and Act ACP), belonging to the type II PKSs, yields flavokermesic acid (FK) (called TMAC in bacterial articles) when combined with heterologous expression of the ZhuI aromatase/cyclase and ZhuJ cyclase from the zhu gene cluster in Streptomyces sp. R1128. Accordingly, this article describes recombinant introduction of a Streptomyces PKS gene into a Streptomyces host cell, so the PKS is not of a different genus than the host cell.

Figure 2:
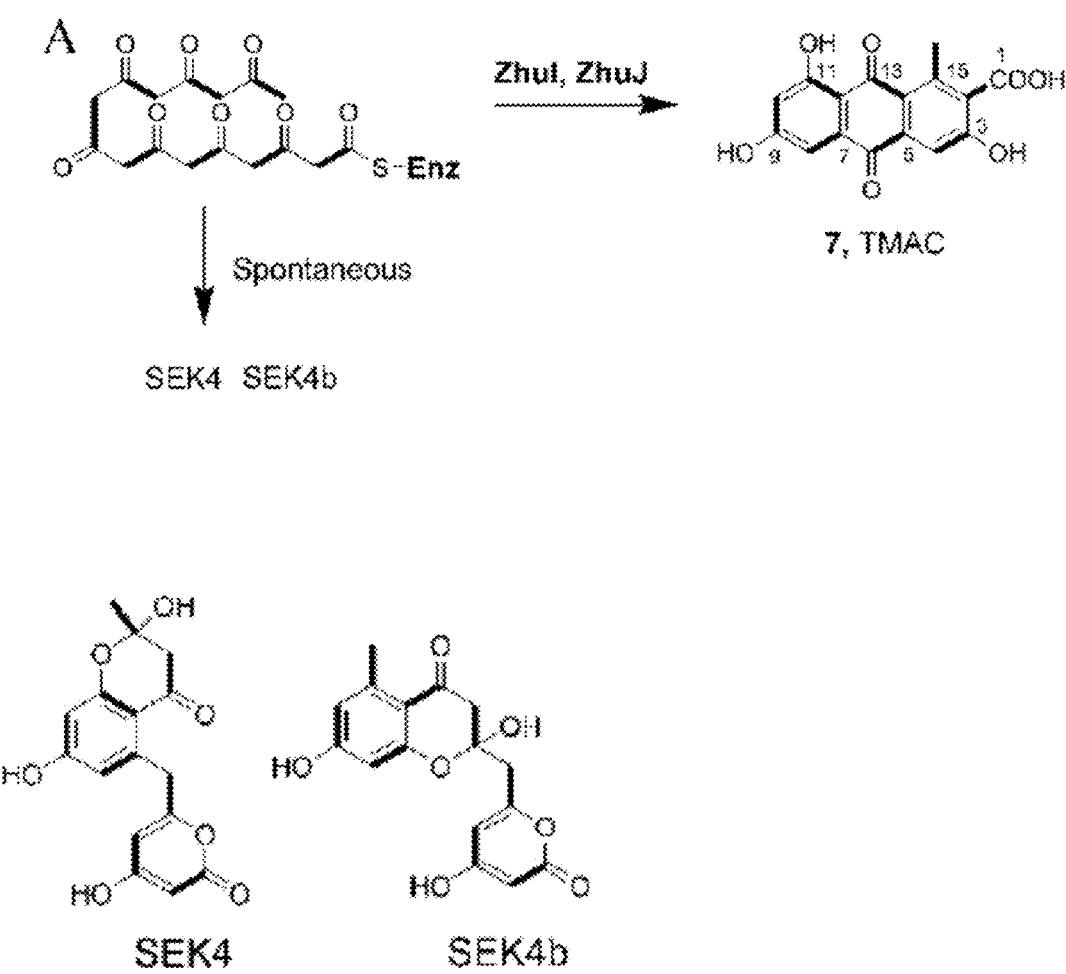

In FIG. 2 herein is shown FIG. 5A of the Tang, Y. et al (2004) article. As can be seen in the figure and as further described in the article, the Act PKS (termed octaketide synthase (OKS)) creates a non-reduced octaketide and this octaketide is via the ZhuI aromatase/cyclase and ZhuJ cyclase converted into flavokermesic acid (FK) (called TMAC). The SEK4 and SEK4B compounds are also spontaneously produced (structures shown in FIG. 2 may herein be termed shunt products).

In the plant Aloe arborescens, identified PKSs have been shown to produce polyketides of various lengths including octaketides, see e.g. Mizuuchi et al (2009) where it in FIG. 1 is illustrated that the octaketide synthases (OKSs) termed PKS4 and PKS5 may, by using malonyl-CoA as extender units, create a non-reduced octaketide. The SEK4 and SEK4B shunt compounds are also spontaneously formed.

The plant Hypericum perforatum (St. John's wort) also comprises octaketide synthases, see e.g. Karppinen et al (2008), where it is described that the PKS termed HpPKS2 was expressed in E. coli, followed by purification and in vitro biochemical characterization of the enzyme. In FIG. 1 of the article is illustrated that the PKS termed HpPKS2 creates a non-reduced octaketide (using acetyl-CoA as starter unit and malonyl-CoA as extender units) and the shunt products SEK4 and SEK4B are spontaneously formed.

The article of Yu et al. (2012) provides a review of Type III Polyketide synthases in natural product biosynthesis; the article reads on page 293: "Various type III PKSs have been engineered into E. coli to generate novel polyketides. The production of plant-specific curcuminoids has been reconstituted in E. coli by co-expressing CUS with phenylalanine ammonia-lyase from Rhodotorula rubra and 4-coumarate: CoA ligase (4CL) from Lithospermum erythrorhizon". As explained in the article, the PKS termed "CUS" synthesizes a diketide-CoA and therefore CUS is not an octaketide synthase.

The article Jadhav et al (2014) describes that a type III hexaketide PKS from Plumbago zeylanica (PzPKS) was cloned and expressed in tobacco plants to study whether the transgenic tobacco plants expressing PzPKS synthesize the pharmacologically important polyketide, plumbagin.

In none of the above mentioned PKS related articles are discussed production of carminic acid.

Without being limited to theory, it is believed that the prior art does not describe that herein relevant type III PKS octaketide synthases (OKS) may be active in vivo in a heterologous production host cell of a different genus, e.g. a plant type III OKS may be able to create non-reduced octaketides in vivo in a heterologous production host cell, such as e.g. a recombinant Aspergillus production host cell.

The patent application PCT/EP2014/078540 was filed 18 Dec. 2014. At the filing/priority date of the present patent application PCT/EP2014/078540 was not published. It describes a glycosyltransferase (GT) isolated from Dactylopius coccus costa insect which is capable of: (I): conjugating glucose to flavokermesic acid (FK); and/or (II): conjugating glucose to kermesic acid (KA) and use of this GT to e.g. make carminic acid.

PCT/EP2014/078540 does not directly and unambiguously describe herein discussed relevant non-reduced octaketides and/or polyketide synthases (PKS).

SUMMARY OF THE INVENTION

The problem to be solved by the present invention relates to the provision of a suitable biosynthetic pathway that may lead to carminic acid.

An advantage of the provision of such a suitable biosynthetic pathway as described herein is that it opens up the possibility for heterologous production (in e.g. Aspergillus or yeast) of carminic acid without the need to make an extraction from insects and thereby be able to make a carminic acid color composition/product that is free of unwanted Dactylopius coccus costa insect proteins.

One part of the solution relates to that the present inventors identified a Dactylopius coccus extract (including extracts of the endosymbionts present in Dactylopius coccus) with a herein relevant glycosyltransferase GT activity. As discussed herein, the present inventors analyzed the GT and identified that it is capable of: (I): conjugating glucose to flavokermesic acid (FK); and/or (II): conjugating glucose to kermesic acid (KA). Accordingly, this GT can be used to e.g. make carminic acid.

The polynucleotide sequence encoding herein described isolated/cloned novel Dactylopius coccus costa glycosyltransferase is shown in SEQ ID NO: 1 herein and the polypeptide amino acid sequence is shown in SEQ ID NO: 2 herein.

The herein relevant glycosyltransferase enzyme of SEQ ID NO: 2 may herein be termed "DcUGT2" or simply "DcUGT".

FIG. 1 shows a schematic presentation of the herein relevant glycosyltransferase activity of the herein described isolated/cloned DcUGT glycosyltransferase of SEQ ID NO:2 herein, as illustrated in the figure, it was found to be able to conjugate glucose to the aglycons flavokermesic acid (FK) and kermesic acid (KA).

Based on the prior art the skilled person does not know which compound is the primary glucosylated compound during the biosynthetic production of carminic acid in vivo in Dactylopius coccus.

The present inventors demonstrated that Dactylopius coccus contains a GT able to C-glycosylate flavokermesic acid (FK) and/or kermesic acid (KA). Accordingly, and without being limited to theory, it is plausible that flavokermesic acid (FK) and/or kermesic acid (KA) are suitable aglucons for e.g. in vivo heterologous biosynthesis of e.g. carminic acid.

Based on this knowledge, that it is plausible that flavokermesic acid (FK) and/or kermesic acid (KA) are suitable aglycons for e.g. in vivo heterologous biosynthesis of e.g. carminic acid, the present inventors identified that herein relevant glycosyltransferases may also be identified in *Aloe* plants, *Haworthia* plants and *Sorghum* or rice plants.

Having identified possible suitable aglucons, the present inventors could go back and try to identify suitable prior intermediate compounds that could be suitable for in vivo biosynthesis of the relevant aglucons (e.g. FK/KA).

As discussed in working Example 6 herein, the present inventors recombinantly expressed plant (*Aloe arborescens* (AaOKS) and/or *Hypericum perforatum* (HpPKS2)) type III polyketide synthases (PKS) octaketide synthases (OKS) in *Aspergillus nidulans* and identified that the OKS actually worked in the heterologous host, there were created non-reduced octaketides in vivo in the *Aspergillus nidulans* cells. The non-reduced octaketides are unstable and the identification that non-reduced octaketides were present in vivo was verified by the accumulation of the shunt/degradation products SEK4 and SEK4B (see FIG. 2 herein and above discussed prior art+Example 6 herein).

As discussed in the conclusion paragraph of working Example 6 herein, expression of plant type III PKS (HpPKS2 or AaOKS) resulted in the production of different compounds including the compounds SEK4, SEK4B and flavokermesic acid (FK) in vivo in *Aspergillus nidulans*. Since there in this Example 6, were not inserted heterologous cyclases and/or aromatases into the *Aspergillus* strains and FK compound was identified, it indicates that the *Aspergillus* strains may comprise homologous cyclases and/or aromatases capable of converting non-reduced octaketide into FK compound in vivo.

As discussed in the conclusion paragraph of working Example 8 herein, the present inventors made a co-expression of the heterologous plant PKS (AaOKS) and glycosyltransferase (DcUGT2) in *Aspergillus nidulans* and it resulted in the in vivo production of carminic acid (CA) and DcII.

With respect to experimental work of the present inventors in relation to heterologous expression/production in *Nicotiana benthamiana* plant (a close relative of tobacco plant), as discussed in the conclusion paragraph of working Example 11 herein, the results of this Example 11 demonstrated that:

(i): The plant PKS AaOKS gene of *Aloe arborescens* was transiently expressed in *N. benthamiana* and in vivo this resulted in formation of SEK4 and SEK4B, which demonstrated that AaOKS can function as an active octaketide synthase in vivo in *N. benthamiana*;

(ii): Since no flavokermesic acid (FK) anthrone or FK could be observed when AaOKS was agroinfiltrated alone, *N. benthamiana* may lack endogenous enzymes to further metabolize the non-reduced octaketide into these compounds.

(iii): The *Streptomyces* sp. R1128 cyclase genes, ZhuI and ZhuJ, were co-agroinfiltrated (i.e. in vivo co-expressed) with AaOKS and in vivo production/accumulation of different compounds including FK was observed. Accordingly, heterologous expression of *Streptomyces* R1128 cyclase genes resulted in the in vivo production of different compounds including FK;

(iv): In vivo production of DcII and carminic acid (CA) was detected when DcUGT2 was co-expressed with AaOKS, ZhuI and ZhuJ in *N. benthamiana*.

Accordingly, the present inventors demonstrated:

(I): A recombinantly introduced Type III-like polyketide synthase (PKS) gene encoding an octaketide synthase (OKS) (such as e.g. *Aloe arborescens* (AaOKS) and/or *Hypericum perforatum* (HpPKS2)) and wherein the OKS is of a different genus than the host cell (such as e.g. a fungal *Aspergillus nidulans* or *Nicotiana benthamiana* plant host cell) is capable of converting suitable starter and extender units into a non-reduced octaketide under suitable growth conditions and there is then in vivo produced the non-reduced octaketide; and (II): It is possible to convert in vivo within the growing recombinant host cell the non-reduced octaketide of step (I) into a $C_{14}$-$C_{34}$ aromatic aglycon compound of interest (e.g. flavokermesic acid (FK) or kermesic acid (KA)), wherein the aromatic aglycon compound of interest is not SEK4 and/or SEK4B (i.e. SEK4 and/or SEK4B are derived spontaneously from the non-reduced octaketide and may herein be termed shunt products);

(III): If the recombinant host cell also comprises a glycosyltransferase gene encoding a glycosyltransferase then the in step (II) produced aromatic aglycon compound of interest may be in vivo glycosylated by the glycosyltransferase to produce a $C_{14}$-$C_{34}$ aromatic glycoside compound of interest (e.g. carminic acid (CA) or DcII)).

It is believed that above step (II) may by itself be seen as a novel significant contribution to the art by the present invention, since based on the prior art the skilled person could not know for sure that the in step (I) created non-reduced octaketide would in fact be "freely" available in vivo within the recombinant host cell of the different genus to actually be converted into a different aromatic aglycon compound of interest (e.g. flavokermesic acid (FK)) and not only the spontaneously produced SEK4 and/or SEK4B compounds.

As discussed herein, it may be preferred that in vivo conversion of the non-reduced octaketide is done via involvement of in trans acting (independent of the PKS enzyme) a romatases/cyclases.

As discussed above, the experimental work of the present inventors as discussed in working examples herein demonstrated that it is possible to make heterologous in vivo production of e.g. insect *Dactylopius costa* carminic acid (CA) in different recombinant production host cells such as fungal *Aspergillus nidulans* cells or *Nicotiana benthamiana* plant (a close relative of tobacco plant) cells.

As discussed above, today one may only get carminic acid (CA) by direct isolation from *Dactylopius* insect bodies or via chemical synthesis of carminic acid by a route involving different intermediates (U.S. Pat. No. 5,424,421).

Accordingly, it may be seen as a major contribution to the art that it is herein demonstrated that it is possible to make in vivo heterologous production of carminic acid (CA) in e.g. fungal *Aspergillus* cells or *Nicotiana* plant cells.

As understood by the skilled person in the present context, based on the novel technical information herein there is no reason to believe that it should not be possible to make in vivo heterologous recombinant cell production of different octaketide derived compounds of interest—such as e.g. a $C_{14}$-$C_{34}$ aromatic compounds of interest, where examples of such $C_{14}$-$C_{34}$ aromatic compound could e.g. be Mutactin (see e.g. FIG. 2 in above discussed Tang, Y. et al (2004) article); Emodin, Hypericin or Pseudohypericin (see e.g. FIG. 1 in above discussed Karppinen et al (2008) article); or Barbaloin (see e.g. FIGS. 1 and 4 in above discussed Mizuuchi et al (2009) article); or carminic acid (CA).

As understood by the skilled person in the present context, in step (II) of the method of the first aspect as described herein, the specific types of in vivo created $C_{14}$-$C_{34}$ aromatic aglycon specific compounds of interest (such e.g. flavokermesic acid (FK) or kermesic acid (KA)) will generally depend on the post-PKS enzymes (e.g. homologous or heterologous aromatases and/or cyclases) present within the used recombinant host cell.

In the prior art is described numerous different e.g. aromatases and/or cyclases that a skilled person may use to create specific $C_{14}$-$C_{34}$ aromatic aglycon of interest in step (II) of the method of the first aspect as described herein.

Figure 3:
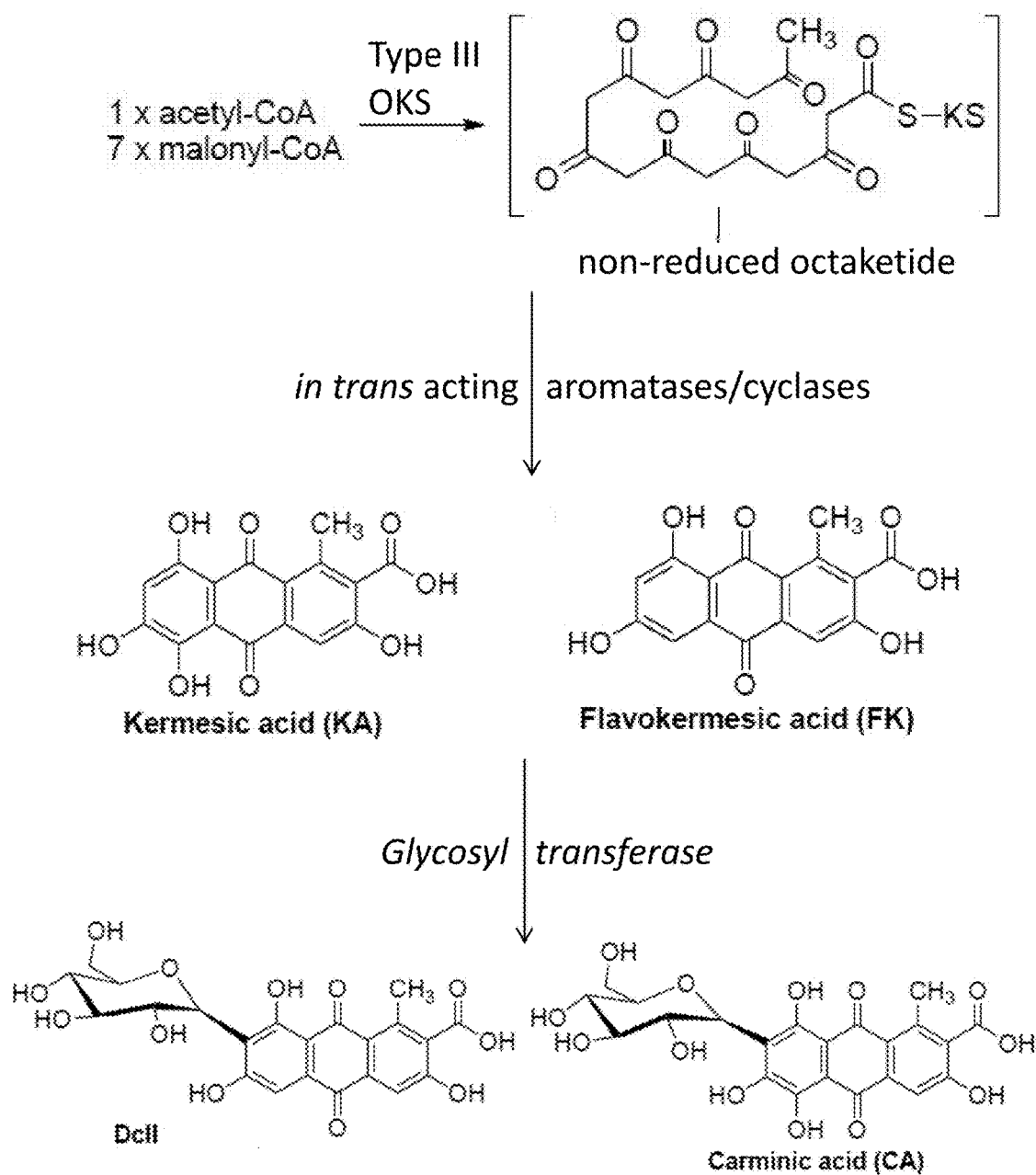

Based on the results discussed herein, there is in FIG. 3 herein shown an example of a model for a suitable biosynthetic pathway that may lead to carminic acid.

In short, the example of a biosynthetic pathway model comprises following steps:

(i): using a type III PKS octaketide synthase to create a non-reduced octaketide;

(ii): conversion of the non-reduced octaketide via in trans acting (independent of the PKS enzyme) aromatases/cyclases into flavokermesic acid (FK) and/or kermesic acid (KA); and (iii): (1): the kermesic acid (KA) aglucon is glucosylated to yield carminic acid CA; or
(2): the FK is glucosylated to yield DcII, which is further hydroxylated to yield carminic acid (CA).

As discussed above and without being limited to theory, it is believed that the prior art does not describe that herein relevant type III PKS octaketide synthases (OKS) may be active in vivo in a heterologous production host cell of a different genus, e.g. a plant type III OKS may be able to create non-reduced octaketides in vivo in a heterologous production host cell such as e.g. a recombinant *Aspergillus* production host cell.

As discussed above, in the prior art it is known that non-reduced octaketides may in vivo be converted into different octaketide derived aromatic compounds of interest, the specific type of aromatic compound of interest will generally depend on the specific post-PKS enzymes (e.g. aromatases and/or cyclases) present in vivo in the host cell. For instance, in FIG. 1 of above discussed Karppinen et al (2008) article is shown that non-reduced octaketides may in vivo in *H. perforatum* be converted into the aromatic compounds Emodin anthrone and/or Emodin (an Anthraquinone).

In FIG. 1 of above discussed Mizuuchi et al. (2009) article is shown that non-reduced octaketide may in vivo in *A. arborescens* be converted into the aromatic octaketide anthrone barbaloin compound.

Accordingly, a first aspect of the present invention relates to a method for producing an octaketide derived aromatic compound of interest, wherein the method comprises following steps:

(I): contacting in vivo in a recombinant host cell comprising a recombinantly introduced Type III polyketide synthase (PKS) gene encoding an octaketide synthase (OKS) and wherein the OKS is of a different genus than the host cell:

(i): suitable starter unit and extender units with the recombinantly introduced OKS capable of converting the starter and extender units into a non-reduced octaketide under suitable conditions wherein there in vivo is produced the non-reduced octaketide; and (II): converting in vivo within the recombinant host cell the non-reduced octaketide of step (I) into a $C_{14}$-$C_{34}$ aromatic aglycon compound of interest, wherein the aromatic aglycon compound of interest is not SEK4 and/or SEK4B; and (III): optionally, the recombinant host cell also comprises a glycosyltransferase gene encoding a glycosyltransferase and the in step (II) produced aromatic aglycon compound of interest is in vivo glycosylated by the glycosyltransferase to produce a $C_{14}$-$C_{34}$ aromatic glycoside compound of interest; and (IV): isolating the aromatic aglycon compound of interest of step (II) and/or isolating the aromatic glycoside compound of interest of step (III) to get a composition, wherein the composition comprises less than 1% w/w dry matter of recombinant host cell material.

As discussed above, the present inventors recombinantly expressed plant (*Aloe arborescens* and/or *Hypericum perforatum*) Type III polyketide synthases (PKS) octaketide synthases (OKS) in *Aspergillus nidulans* and identified that the OKS actually worked in the heterologous host. Accordingly, an example of a host cell in step (I) could e.g. be *Aspergillus nidulans* and an example of a Type III PKS/OKS of step (I) could e.g. be an OKS from *Aloe arborescens* and/or *Hypericum perforatum*.

As discussed above and as known in the art, non-reduced octaketides may in vivo be converted spontaneously into the SEK4 and SEK4B compounds (structures shown in FIG. 2 may be termed shunt products).

As understood by the skilled person in the present context, the identification of SEK4 and/or SEK4B in vivo within the recombinant host cell demonstrates that non-reduced octaketide is present in vivo.

Accordingly and as understood by the skilled person, a Type III octaketide synthase (OKS) of step (I) may be defined as an OKS, which in vitro is capable of producing the octaketide-derived shunt products SEK4 and/or SEK4B.

An assay for such an in vitro analysis is described e.g. in working Example 9 herein.

As discussed above, the term Type III polyketide synthase (PKS) is well-known to the skilled person and the skilled person can therefore routinely identify if a PKS of interest is understood to be a Type III PKS and therefore not a Type I or a Type II PKS.

As discussed above, in the prior art it is known that non-reduced octaketides may in vivo be converted into different octaketide-derived aromatic compounds of interest and this will generally depend on the specific post-PKS enzymes (e.g. aromatases and/or cyclases) present in vivo in the host cell.

Accordingly and as understood by the skilled person, in the present context, the conversion in step (II) of the non-reduced octaketide into a $C_{14}$-$C_{34}$ aromatic aglycon compound of interest is generally done by involvement of suitable post-PKS enzymes (e.g. aromatases and/or cyclases) present in vivo in the host cell.

The aromatic aglycon compound of interest of step (II) may in principle be any herein relevant $C_{14}$-$C_{34}$ aromatic aglycon compound of interest, such as e.g. an aromatic anthraquinone compound or an aromatic anthrone compound (for further details see below).

As discussed above—the present inventors identified that flavokermesic acid (FK) was present in the *Aspergillus nidulans* cells comprising recombinantly introduced Type III OKS from *Aloe arborescens* and/or *Hypericum perforatum*.

Flavokermesic acid (FK) and kermesic acid (KA) both have 16 carbon (C) atoms, —they are understood to be examples of $C_{16}$ aromatic aglycon compounds and as such examples of $C_{14}$-$C_{34}$ aromatic aglycon compounds of interest in step (II).

As discussed herein, if the in step (IV) isolated aromatic aglycon compound of interest is FK this may e.g. in vitro via glucosylation be converted into DcII and thereafter into carminic acid (CA) (see e.g. FIG. 3 herein).

As discussed herein, another optional alternative example could be that the host cell also in vivo expresses a herein relevant glycosyltransferase and there in step (III) in vivo in the host cell is produced e.g. DcII and/or carminic acid (CA). This may be seen as an example of optional step (III) of the first aspect.

Working Examples herein show preferred examples of this optional alternative.

DcII and/or carminic acid (CA) are both glucosides and the aglycon part (i.e. not including the glucose) of these compounds have 16 carbon (C) atoms.

Accordingly, both of these DcII and/or carminic acid (CA) compounds are herein understood to be examples of $C_{16}$ aromatic glycoside compounds and as such examples of $C_{14}$-$C_{34}$ aromatic glycoside compounds of interest in optional step (III).

As understood by the skilled person, in the present context, the isolating step (IV) essentially relates to a step to isolate/purify the aromatic compound of interest from recombinant host cell material (or cultivation/growth media if the host cell is e.g. a fungal/microorganism cell).

The present inventors identified that flavokermesic acid (FK) was present in the *Aspergillus nidulans* cells comprising recombinantly introduced Type III OKS from *Aloe arborescens* and/or *Hypericum perforatum*.

One may say that it is surprising that the prior art does not describe that herein relevant type III PKS octaketide synthases (OKS) may be active in vivo in a heterologous production host cell of a different genus, e.g. a plant type III OKS may be able to create non-reduced octaketides in vivo in a heterologous production host cell such as e.g. a recombinant *Aspergillus* production host cell.

As discussed above, the prior art describes numerous examples of in vitro tests on different OKS enzymes. However, no prior art describes that the OKS works in vivo in a host cell of a different genus.

Without being limited to theory, type III OKS may work in a heterologous host when the OKS is being protected in vivo against degradation (e.g. via formation of metabolons/complexes with other proteins). This degradation mechanism is not present in vitro.

The fact, that an OKS works in *Aspergillus nidulans* and *Nicotiana* plant cells demonstrates that the plant cells are capable of protecting a heterologous recombinant introduced OKS.

It is believed that this may be considered a general matter, i.e. that such protective systems will also be present in many other host cell types (such as e.g. yeast, tobacco plants etc).

In addition the octaketide product of the OKS is spontaneously degraded into SEK4 and/or SEK4B, which may inhibit the enzyme at the in vivo concentrations. When enzymes metabolizing the octaketide are present the PKS will not be inhibited by SEK4 and/or SEK4B and remain active.

In conclusion, a suitable method to produce an active OKS is to express it together with enzymes metabolizing the octaketide and/or forming complexes with the enzymes. These enzymes may be present natively in the cells expressing the introduced OKS or may be recombinantly introduced.

The fact as shown herein, that flavokermesic acid (FK) was present in the *Aspergillus nidulans* cells comprising recombinantly introduced Type III OKS from *Aloe arborescens* and/or *Hypericum perforatum* shows that *Aspergillus nidulans* cells comprise enzymes (e.g. aromatases/cyclase) metabolizing the produced non-reduced octaketide.

Without being limited to theory, it is believed that this may be considered a general matter, i.e. that such cyclases and/or aromatases will also be present in many other host cell types (such as e.g. yeast, tobacco plants etc).

Definitions

All definitions of herein relevant terms are in accordance of what would be understood by the skilled person in relation to the herein relevant technical context.

The term "aglycon" denotes non-carbohydrate part of the corresponding glycosylated form of the aglycon. When the sugar is glucose the aglycon may be termed aglucon. Further, when the sugar is glucose the term glucosylated may be used instead of glycosylated. When the aglycon is glycosylated at a hydroxy group there is generally created a so-called β-glycosidic bond, i.e. a so-called β-Glycoside (or O-Glucoside if the sugar is glucose). When the aglycon is glycosylated by a carbon-carbon linkage it may herein be termed a C-glycosidic bond, i.e. a so-called C-Glycoside (or C-Glucoside if the sugar is glucose).

The term "glycoside" denotes a compound, which on hydrolysis can give a sugar and a non-sugar (aglycon) residue, e. g. glucosides can give glucose, galactosides can give galactose.

The term "glycosyltransferase" denotes an enzyme capable of conjugating a nucleotide activated sugar to a compound (e.g. an aglycon compound). The sugar may e.g. be D and L isomers of galactose, glucosamine, N-acetylglusamine, xylose, glucuronic acid, rhamnose, arabinose, mannose or glucose. Alternatively the sugar may be a carbohydrate derivative such as e.g. inositol, olivose, rhodinose and etc. available as nucleotide diphosphates. Further the sugar may for instance be a monosaccharide, a disaccharide or a trisaccharide. In the case of oligo- and polysaccharides the sugars are linked one by one by e.g. involving the use of one or several glycosyltransferases. If the sugar is glucose the glycosyltransferase may be termed a glucosyltransferase.

When the glycosyltransferase conjugates a nucleotide-activated sugar to a compound via a C-glycosidic bond it may herein be termed a C-glycosyltransferase.

When the glycosyltransferase conjugates a sugar to an aglycon via an β-glycosidic bond it may herein be termed an β-glycosyltransferase.

The term "hybridizes" in relation to a polynucleotide which hybridizes under at least medium stringency conditions with (i) nucleotides 1 to 1548 of SEQ ID NO:1 or (ii) a complementary strand of (i) relates to the nucleotide sequence hybridizes to a labeled nucleic acid probe corresponding to the nucleotide sequence shown in SEQ ID NO:1 or its complementary strand under medium to very high stringency conditions. Molecules to which the nucleic acid probe hybridizes under these conditions can be detected using e.g. X-ray film.

Herein relevant hybridization stringency conditions are stringency conditions that the skilled person normally would understand are relevant, i.e. for medium stringency conditions the conditions that skilled person would understand are medium stringency conditions. The skilled person knows herein relevant hybridization stringency conditions, see e.g.

(J. Sambrook, E. F. Fritsch, and T. Maniatus, 1989, Molecular Cloning, A Laboratory Manual, 2d edition, Cold Spring Harbor, N.Y.).

According to the art, for long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

The term "in vitro" (Latin: in glass) relates to studies that are conducted using components of an organism that have been isolated from its usual biological surroundings in order to permit a more detailed or more convenient analysis than can be done with whole organisms. Colloquially, these experiments are commonly called "test tube experiments". In contrast, in vivo studies are those that are conducted with living organisms in their normal intact state.

The term "in vivo" (Latin for "within the living") relates to experimentation using a whole, living organism as opposed to a partial or dead organism, or an in vitro ("within the glass", e.g., in a test tube or petri dish) controlled environment.

The term "isolated polynucleotide" essentially relates herein to that the polynucleotide is isolated from its natural environment. Said in other words that the polynucleotide preparation is essentially free of other polynucleotide material with which it is natively associated. The polynucleotide sequence encoding the herein described isolated/cloned novel glycosyltransferase is shown in SEQ ID NO:1 and it was isolated from the insect *Dactylopius coccus*. Accordingly, as understood by the skilled person, the term "isolated polynucleotide" as used herein does not cover the polynucleotide of SEQ ID NO:1 as it is naturally present in the genome of *Dactylopius coccus*. The term "isolated polynucleotide" essentially relates to that the isolated polynucleotide is in a form suitable for use within genetically engineered protein production systems. Thus, an isolated polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. The term "isolated polynucleotide" may herein alternatively be termed "cloned polynucleotide".

The term "isolated polypeptide" essentially relates herein to that the polypeptide is isolated from its natural environment. The herein described novel glycosyltransferase polypeptide as shown in SEQ ID NO: 2 herein was isolated from the insect *Dactylopius coccus*. Accordingly, as understood by the skilled person in the present context, the term "isolated polypeptide" as used herein does not cover the glycosyltransferase polypeptide of SEQ ID NO:2 as it is naturally present in the genome of *Dactylopius coccus*. The term "isolated polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated, as understood by the skilled person in the present context, the term "other polypeptide material with which it is natively associated" may in relation to the herein described novel glycosyltransferase polypeptide as shown in SEQ ID NO: 2 be seen in relation to other polypeptide material with which it is natively associated in *Dactylopius coccus*. In some case, it may be preferred that the "isolated polypeptide" refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

The term "non-reduced octaketide" denotes a non-reduced octaketide, wherein the non-reduced type is characterized by the presence of the originally ketone groups in the ketides (—CH2-CO—), originating from the starter or extender units, either as ketones or in the form of double bonds in aromatic groups. In reduced polyketides a single or all ketones have been reduced to alcohol (—CH2-CHOH—) groups by e.g. a KR domain/enzyme, or further to an alkene group (—C=C—) by e.g. a DH domain/enzyme, or even further to an alkane group (—CH2-CH2-) by e.g. an ER domain/enzyme. Based on these chemical features of the formed products the involved PKSs are categorized as either being a non-reducing PKS or a reducing PKS.

The term "non-reducing PKS" or "non-reducing polyketide synthase" denotes a PKS which does not reduce the ketone groups in the formed polyketide chain. The lack of reductions can for instance be due to (I) a lack of the necessary keto-reductase (KR) active sites in the enzyme; and/or (II) lack of tailoring enzymes capable of catalyzing the keto-reduction reaction.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention. As known in the art control sequences include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "octaketide" (greek for "eight") denotes a polyketide chain consisting of eight ketide units, meaning that the polyketide backbone consists of 16 carbon atoms. The term "ketide" refers to a —CH2-CO— unit or modification of this group.

The term "recombinant expression vector" relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites.

The term "recombinant host cell" should herein be understood according to the art. As known in the art, recombinant polynucleotide (e.g. DNA) molecules are polynucleotide (e.g. DNA) molecules formed by laboratory methods of genetic recombination (such as molecular cloning) to bring together genetic material from multiple sources, creating sequences that would not otherwise be found in biological organisms. As understood by the skilled person, a recombinant host cell comprises recombinant polynucleotide (e.g. DNA) molecules and a recombinant host cell will therefore not be understood as covering a natural wildtype cell as such, like e.g. a natural wildtype *Dactylopius coccus* cell.

The term "Sequence Identity" relates to the relatedness between two amino acid sequences or between two nucleotide sequences.

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment).

For purposes of the present invention, the degree of sequence identity between two nucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment).

As understood by the skilled person in the present context, for both "sequence identity between two nucleotide sequences" and "sequence identity between two amino acid sequences", the term "Length of Alignment" should be understood as the actual length of alignment between the two sequences to be compared for sequence identity.

For instance, if a reference sequence is a specific SEQ ID of e.g. 100 amino acids and the other sequence is an identical sequence with 25 amino acids less at one end (i.e. the other sequence is of a length of 75 amino acids) then the "Length of Alignment" will be 75 amino acids and the percent identity will be 100%.

Another example is for instance, if a reference sequence is a specific SEQ ID of e.g. 100 amino acids and the other sequence is an identical sequence with 25 amino acids extra at one end (i.e. the other sequence is of a length of 125 amino acids) then will the "Length of Alignment" be 100 amino acids and the percent identity will be 100%.

The term "Type III polyketide synthase (PKS)" is, as discussed herein, a well-known term to the skilled person and the skilled person will know if a specific PKS of interest is a Type III PKS. As discussed in the review article of Yu et al (2012), Type III PKSs are self-contained enzymes that form homodimers. Their single active site in each monomer catalyzes the priming and extension to form polyketide products.

Embodiments of the present invention is described below, by way of examples only.

DRAWINGS

FIG. 1: Schematic presentation of the herein relevant glycosyltransferase activity of the herein described isolated/cloned novel glycosyltransferase of SEQ ID NO:2 herein. As illustrated in the figure, it was found to be able to conjugate glucose to the aglycons flavokermesic acid (FK) and kermesic acid (KA).

FIG. 2: Shows FIG. 5A of the Tang, Y. et al (2004) article. As can be seen in the figure and as further described in the article, the Act PKS (termed octaketide synthase (OKS)) creates a non-reduced octaketide and this octaketide is via the ZhuI aromatase/cyclase and ZhuJ cyclase converted into flavokermesic acid (FK) (called TMAC). The SEK4 and SEK4B compounds are also formed spontaneously (structures shown in FIG. 2 may be termed shunt products).

FIG. 3: Shows an example of a model for a suitable biosynthetic pathway that may lead to carminic acid.

Figure 4:
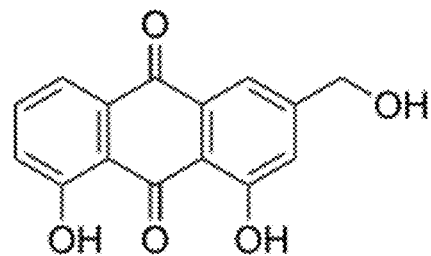
Figure 4:
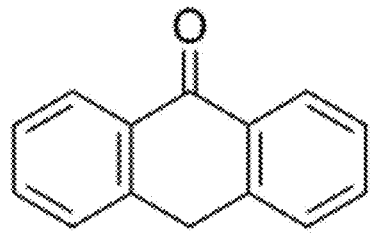
Figure 4:
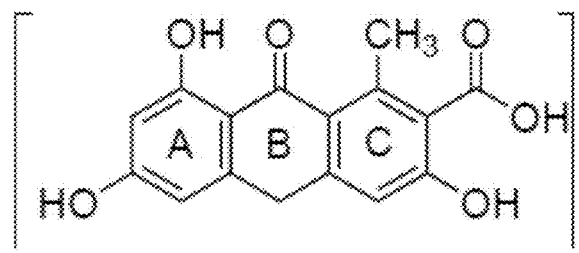

FIG. 4: Shows 9,10-anthraquinone skeleton; anthrone skeleton and FK antrone compound structure.

DETAILED DESCRIPTION OF THE
INVENTION

A Recombinant Host Cell—e.g. Step (I)

Based on e.g. the sequence information disclosed herein, it is routine work for the skilled person to make a herein relevant recombinant host cell. As an example, based on the prior art the skilled person knows numerous different suitable recombinant host cells that for years have been used as recombinant host cells for e.g. expression of different polypeptides of interest.

The recombinant host cell in the method of the first aspect may be a growing recombinant host cell or e.g. in a so-called stationary phase.

Preferably, the recombinant host cell in the method of the first aspect is a growing recombinant host cell and step (I) and step (II) of the first aspect are:

(I): contacting in vivo in a growing recombinant host cell comprising a recombinantly introduced Type III polyketide synthase (PKS) gene encoding an octaketide synthase (OKS) and wherein the OKS is of a different genus than the host cell:

(i): suitable starter unit and extender units with the recombinantly introduced OKS capable of converting the starter and extender units into a non-reduced octaketide under suitable growth conditions wherein there in vivo is produced the non-reduced octaketide; and (II): converting in vivo within the growing recombinant host cell the non-reduced octaketide of step (I) into a $C_{14}$-$C_{34}$ aromatic aglycon compound of interest, wherein the aromatic aglycon compound of interest is not SEK4 and/or SEK4B.

The recombinant host cell may be any suitable cell such as any eukaryotic cell [e.g. mammalian cells (such as e.g. Chinese hamster ovary (CHO) cells) or a plant cell] or any prokaryotic cell.

It may be preferred that the recombinant host cell is a plant cell, preferably wherein the plant cell is a plant cell selected from the group consisting of: *Nicotiana* sp. (e.g. *Nicotiana benthamiana* cells); rhubarb, buckweed, *Hypericum* and *Aloe* sp. Preferably, the plant cell is a *Nicotiana* sp., more preferably the plant cell is *Nicotiana benthamiana*.

The recombinant host cell may be a cell selected from the group consisting of a filamentous fungal cell and a microorganism cell.

Filamentous fungi include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

It may be preferred that the filamentous fungal cell is a cell of a species selected form the group consisting of, but not limited to, *Acremonium, Aspergillus, Fusarium, Humicola, Mucor, Myceliophthora, Neurospora, Penicillium, Thielavia, Tolypocladium*, and *Trichoderma* or a teleomorph or synonym thereof.

A preferred *Aspergillus* cell is *Aspergillus niger, Aspergillus oryzae* or *Aspergillus nidulans*. The most preferred *Aspergillus* cell is *Aspergillus nidulans*.

A preferred microorganism cell herein is a microorganism cell selected from the group consisting of a yeast cell and a prokaryotic cell.

A preferred yeast cell is a yeast cell of a phylum selected from the group consisting of Ascomycetes, Basidiomycetes and fungi imperfecti. Preferably the yeast cell is of the phylum Ascomycetes.

A preferred Ascomycetes yeast cell is of a genus selected from the group consisting of *Ashbya, Botryoascus, Debaryomyces, Hansenula, Kluveromyces, Lipomyces, Saccharomyces*, sush as *Saccharomyces cerevisiae, Pichia* and *Schizosaccharomyces*.

A preferred yeast cell is a yeast cell of a genus selected from the group consisting of *Saccharomyces*, such as *Saccharomyces cerevisiae* and *Pichia*.

A preferred prokaryotic cell is selected from the group consisting of: *Bacillus, Streptomyces, Corynebacterium, Pseudomonas*, lactic acid bacteria and an *E. coli* cell.

A preferred *Bacillus* cell is *B. subtilis, Bacillus amyloliquefaciens* or *Bacillus licheniformis*.

A preferred *Streptomyces* cell is *Streptomyces setonii* or *Streptomyces coelicolor*.

A preferred *Corynebacterium* cell is *Corynebacterium glutamicum*.

A preferred *Pseudomonas* cell is *Pseudomonas putida* or *Pseudomonas fluorescens*.

Polyketide synthase (PKS) gene encoding an octaketide synthase (OKS)—e.g. step (I) Step (I) of the first aspect relates to "Type III polyketide synthase (PKS) gene encoding an octaketide synthase (OKS) and wherein the OKS is of a different genus than the host cell".

As discussed above and as known in the art—non-reduced octaketides may spontaneously be converted in vivo to the SEK4 and SEK4B compounds (structures shown in FIG. 2 herein—may herein be termed shunt products).

As understood by the skilled person in the present context—identification of SEK4 and/or SEK4B in vivo within the recombinant host cell demonstrates that non-reduced octaketide is present in vivo.

Accordingly, the Type III octaketide synthase (OKS) of step (I) may be defined as an OKS, which in vitro is capable of producing the octaketide-derived shunt products SEK4 and/or SEK4B.

Assay for such an in vitro analysis is described e.g. in working Example 9 herein.

As discussed above, the skilled person knows if a specific PKS of interests is a Type III PKS.

As discussed above, in the prior art is known several different type III PKSs from plants, bacteria and/or fungi.

Accordingly, it may be preferred that the Type III polyketide synthase (PKS) gene of step (I) is a PKS gene from a plant, a bacterium or a fungi, Preferably, the Type III polyketide synthase (PKS) gene of step (I) is a PKS gene from a plant.

If the Type III polyketide synthase (PKS) gene of step (I) is a PKS gene from a plant it is preferred that the plant is a plant selected from the group consisting of: *Aloe* spp. (preferably *Aloe arborescens*), *Hypericum* spp. (preferably *Hypericum perforatum*), rhubarb, buckweed and *Hawortia* spp.

Preferably the plant is a plant selected from the group consisting of: *Aloe* spp. and *Hypericum* spp.

More preferably, the plant is a plant selected from the group consisting of: *Aloe arborescens* and *Hypericum perforatum*.

If the Type III polyketide synthase (PKS) gene of step (I) is a PKS gene from a bacterium it is preferred that the bacterium is a bacterium selected from the group consisting of: *Streptomyces* spp. (preferably *Streptomyces coelicolor*).

If the Type III polyketide synthase (PKS) gene of step (I) is a PKS gene from a fungi it is preferred that the fungi is a fungi selected from the group consisting of: *Acremonium, Aspergillus, Fusarium, Humicola, Mucor, Myceliophthora, Neurospora, Penicillium, Thielavia, Tolypocladium*, and *Trichoderma*.

A preferred *Aspergillus* is *Aspergillus niger, Aspergillus oryzae* or *Aspergillus nidulans*. The most preferred *Aspergillus* is *Aspergillus nidulans*.

As known in the art, a Type I PKS and/or a Type II PKS may be mutated to remove relevant elements (e.g. active sites) to convert it into what the skilled person in the present context would functionally consider being a Type III PKS. A PKS, which by the skilled person is functionally considered being a Type III PKS is herein understood to be a Type III PKS. As discussed above and in working examples herein, the present inventors recombinantly expressed plant (*Aloe arborescens* and/or *Hypericum perforatum*) type III polyketide synthases (PKS) octaketide synthases (OKS) in *Aspergillus nidulans* and identified that the OKS actually worked in the heterologous host, i.e. there were created non-reduced octaketides in vivo in the *Aspergillus nidulans* cells.

As discussed herein, flavokermesic acid (FK) was also identified in the *Aspergillus nidulans* cells.

Public available *Aloe arborescens* OKS sequences are herein shown with following SED ID numbers:

Herein termed AaOKS: SEQ ID NO:6 [Genbank ID number AY567707 (nucleotide seq.) and SEQ ID NO:7: [Genbank ID number AAT48709 (polypeptide seq)];

Herein termed AaOKS2(PKS4): SEQ ID NO:8 [Genbank ID number F3536166] (nucleotide seq.) and SEQ ID NO:9 [Genbank ID number ARC19997] (polypeptide seq);

Herein termed AaOKS3(PKS5): SEQ ID NO:10 [Genbank ID number F3536167] (nucleotide seq.) and SEQ ID NO:11 [Genbank ID number ARC19998] (polypeptide seq);

Herein termed AaPKS2_A207G: SEQ ID NO:12 (nucleotide seq.) and SEQ ID NO:13: (polypeptide seq).

Public available *Hypericum perforatum* OKS amino acid sequence is herein shown with following SED ID Number:

Herein termed HpPKS2: SEQ ID NO:14 [Genbank ID number HQ529467] (nucleotide seq.) and SEQ ID NO:15: [Genbank ID number AEE69029] (polypeptide seq);

The level of identities (%) between Type III PKSs at amino acid level:

|  | AaOKS | AaPKS2 | AaOKS3 | HpPKS2 | AaPKS2_A207G |
|---|---|---|---|---|---|
| BAaOKS | — | 96.28% | 89.88% | 43.07% | 91.32% |
| AaOKS2 |  | — | 90.12% | 43.81% | 91.07% |
| AaOKS3 |  |  | — | 45.07% | 85.93% |
| HpPKS2 |  |  |  | — | 43.56% |
| AaPKS2_A207G |  |  |  |  | — |

It may be preferred that the octaketide synthase (OKS) in step (I) of the first aspect is a OKS comprising an amino acid sequence which has at least 70% (preferably at least 80%, more preferably at least 90% and even more preferably at least 98%) identity with amino acids 1 to 403 of SEQ ID NO:7.

It may be preferred that the octaketide synthase (OKS) in step (I) of the first aspect is a OKS comprising an amino acid sequence which has at least 70% (preferably at least 80%, more preferably at least 90% and even more preferably at least 98%) identity with amino acids 1 to 403 of SEQ ID NO:9.

It may be preferred that the octaketide synthase (OKS) in step (I) of the first aspect is a OKS comprising an amino acid sequence which has at least 70% (preferably at least 80%, more preferably at least 90% and even more preferably at least 98%) identity with amino acids 1 to 405 of SEQ ID NO:11.

It may be preferred that the octaketide synthase (OKS) in step (I) of the first aspect is a OKS comprising an amino acid sequence which has at least 70% (preferably at least 80%, more preferably at least 90% and even more preferably at least 98%) identity with amino acids 1 to 403 of SEQ ID NO:13.

It may be preferred that the octaketide synthase (OKS) in step (I) of the first aspect is a OKS comprising an amino acid sequence which has at least 70% (preferably at least 80%, more preferably at least 90% and even more preferably at least 98%) identity with amino acids 1 to 393 of SEQ ID NO:15.

Step (I)—Other Matter

As discussed above, step (I)(i) of the first aspect reads: "suitable starter units and extender units with the recombinantly introduced OKS capable of converting the starter and extender units into a non-reduced octaketide under suitable conditions wherein there in vivo is produced the non-reduced octaketide".

As discussed above, suitable starter units and extender units are known in the art.

According to the art, suitable starter units may e.g. be acetyl-CoA or malonyl-CoA and suitable extender units may e.g. malonyl-CoA.

It is routine work for the skilled person to identify suitable growth conditions wherein there in vivo is produced the non-reduced octaketide as known to the skilled person, such suitable growth conditions will generally depend on the specific used recombinant host cell.

A Recombinant Host Cell and OKS of Different Genus

As discussed above, step (I) of the first aspect reads: "contacting in vivo in a recombinant host cell comprising a recombinantly introduced Type III polyketide synthase (PKS) gene encoding an octaketide synthase (OKS) and wherein the OKS is of a different genus than the host cell"

It is herein most preferred to use a preferred recombinant host cell as discussed herein and a preferred OKS of a different genus as discussed herein.

For instance, a preferred embodiment herein relates to wherein the:

recombinant host cell is a host cell selected from the group consisting of: *Aspergillus* (preferably *Aspergillus nidulans*) and *Nicotiana* sp. (preferably *Nicotiana benthamiana*); and the OKS of a different genus than the host cell is an OKS selected from the group consisting of: OKS from *Aloe* spp. (preferably *Aloe arborescens*) and *Hypericum* spp. (preferably *Hypericum perforatum*).

Preferably, the octaketide synthase (OKS) from *Aloe* spp is:

an OKS comprising an amino acid sequence which has at least 70% (preferably at least 80%, more preferably at least 90% and even more preferably at least 98%) identity with amino acids 1 to 403 of SEQ ID NO:7; or an OKS comprising an amino acid sequence which has at least 70% (preferably at least 80%, more preferably at least 90% and even more preferably at least 98%) identity with amino acids 1 to 403 of SEQ ID NO:9; or an OKS comprising an amino acid sequence which has at least 70% (preferably at least 80%, more preferably at least 90% and even more preferably at least 98%) identity with amino acids 1 to 405 of SEQ ID NO:11; or an OKS comprising an amino acid sequence which has at least 70% (preferably at least 80%, more preferably at least 90% and even more preferably at least 98%) identity with amino acids 1 to 403 of SEQ ID NO:13.

Preferably, the octaketide synthase (OKS) from *Hypericum* spp. is an OKS comprising an amino acid sequence which has at least 70% (preferably at least 80%, more preferably at least 90% and even more preferably at least 98%) identity with amino acids 1 to 393 of SEQ ID NO:15.

Aromatic Aglycon Compound of Interest—Step (II) of First Aspect

As discussed above, step (II) of the first aspect reads: "converting in vivo within the recombinant host cell the non-reduced octaketide of step (I) into a $C_{14}$-$C_{34}$ aromatic aglycon compound of interest, wherein the aromatic aglycon compound of interest is not SEK4 and/or SEK4B".

In a preferred embodiment, the aromatic aglycon compound of interest is a $C_{14}$-$C_{18}$ aromatic aglycon compound of interest.

Preferably the aromatic aglycon compound of interest is at least one compound selected from the group consisting of: anthraquinone compound and anthrone compound.

Within the group above, it is preferred that the aromatic aglycon compound of interest of step (II) is an anthraquinone compound.

According to the art, anthraquinones (also known as anthraquinonoids) are a class of phenolic compounds based on the 9,10-anthraquinone skeleton (see FIG. 4 herein). For example and as understood by the skilled person, flavokermesic acid (FK) and kermesic acid (KA) are examples of anthraquinones.

Anthrones are a class of phenolic compounds based on the anthrone skeleton (see FIG. 4 herein).

In FIG. 4 is shown FK antrone compound structure—i.e an example of a herein relevant anthrone compound.

Preferably, the aromatic aglycon compound of interest is a $C_{16}$ aromatic aglycon compound of interest.

In a preferred embodiment, the $C_{16}$ aromatic aglycon compound of interest is flavokermesic acid (FK) or kermesic acid (KA).

As discussed above, the conversion in step (II) of the non-reduced octaketide into a $C_{14}$-$C_{34}$ (preferably $C_{14}$-$C_{18}$) aromatic aglycon compound of interest is generally done by involvement of suitable post-PKS enzymes (e.g. aromatases and/or cyclases) present in vivo in the host cell.

Accordingly, it may be preferred that the conversion in vivo in step (II) of the method of the first aspect of the non-reduced octaketide into a $C_{14}$-$C_{34}$ aromatic aglycon compound of interest is done via involvement of at least one aromatase/cyclase.

Preferably, it is done via involvement of at least one in trans acting (independent of the PKS enzyme) aromatase/cyclase.

It may be preferred that step (II) of the method of the first aspect is:

(II): converting in vivo within the recombinant host cell the non-reduced octaketide of step (I) into an aromatic aglycon compound of interest, wherein the conversion in vivo of the non-reduced octaketide into an aromatic aglycon compound of interest is done via involvement of at least one in trans acting (independent of the PKS enzyme) aromatase/cyclase and wherein the aromatase/cyclase is from a fungi or a bacteria and heterologous to the recombinant host cell and from a different genus than the PKS.

SEQ ID NO: 17 herein is the public available amino sequence of *Streptomyces* ZhuI aromatase/cyclase (Genbank accession AAG30197) and SEQ ID NO: 19 herein is the public available amino sequence of *Streptomyces* ZhuJ aromatase/cyclase (Genbank accession AAG30196) (see e.g. herein discussed article of Tang, Y. et al (2004)).

As discussed below, these aromatases/cyclases were successfully used in working examples herein.

It may be preferred that the aromatase/cyclase is a aromatase/cyclase comprising an amino acid sequence which has at least 70% (preferably at least 80%, more preferably at least 90% and even more preferably at least 98%) identity with amino acids 1 to 169 of SEQ ID NO:17.

It may be preferred that the aromatase/cyclase is a aromatase/cyclase comprising an amino acid sequence which has at least 70% (preferably at least 80%, more preferably at least 90% and even more preferably at least 98%) identity with amino acids 1 to 256 of SEQ ID NO:19.

Aromatic Glycoside Compound of Interest—Step (III) of First Aspect

As discussed above, optional step (III) of the first aspect reads: "the recombinant host cell also comprises a glycosyltransferase gene encoding a glycosyltransferase and the in step (II) produced aromatic aglycon compound of interest is in vivo glycosylated by the glycosyltransferase to produce a $C_{14}$-$C_{34}$ aromatic glycoside compound of interest".

It may be preferred that this step (III) is fulfilled (i.e. not optional).

In a preferred embodiment, the aromatic glycoside compound of interest is a $C_{14}$-$C_{18}$ aromatic glycoside compound of interest.

As understood by the skilled person in the present context—preferred aromatic aglycon compound of interest of step (II) may be converted into corresponding preferred aromatic glycoside compound of interest in step (III).

Preferably the aromatic glycoside compound of interest is at least one compound selected from the group consisting of: anthraquinone compound, anthrone compound.

Within the group above it is preferred that the aromatic glycoside compound of interest of step (III) is an anthraquinone compound.

For example and as understood by the skilled person—DcII and carminic acid (CA) are examples of anthraquinones.

Preferably, the aromatic glycoside compound of interest is a $C_{16}$ aromatic glycoside compound of interest.

In a preferred embodiment, the $C_{16}$ aromatic glycoside compound of interest is a flavokermesic acid glycoside or a kermesic acid glycoside.

In a preferred embodiment, the flavokermesic acid glycoside is DcII.

In a preferred embodiment, the kermesic acid glycoside is carminic acid (CA).

The glycosyltransferase (GT) of step (III) may e.g. be herein described GT from *Dactylopius coccus*.

Alternatively, it may e.g. be herein discussed glycosyltransferases from *Aloe* plants, *Haworthia* plants, *Sorghum* and/or rice plants.

Preferably, the glycosyltransferase is a glycosyltransferase polypeptide capable of:

(I): conjugating nucleotide activated glucose to flavokermesic acid (FK); and/or (II): conjugating nucleotide activated glucose to kermesic acid (KA).

The polynucleotide sequence encoding herein described isolated/cloned novel *Dactylopius coccus costa* glycosyltransferase is shown in SEQ ID NO: 1 herein and the polypeptide amino acid sequence is shown in SEQ ID NO: 2 herein.

The herein relevant glycosyltransferase enzyme of SEQ ID NO: 2 may herein be termed "DcUGT2".

Accordingly, it may be preferred that the glycosyltransferase is a glycosyltransferase polypeptide capable of:

(I): conjugating nucleotide activated glucose to flavokermesic acid (FK); and/or (II): conjugating nucleotide activated glucose to kermesic acid (KA);

and wherein the glycosyltransferase polypeptide is at least one polypeptide selected from the group consisting of:

(a) a polypeptide comprising an amino acid sequence which has at least 70% identity with amino acids 1 to 515 of SEQ ID NO:2;

(b) a polypeptide comprising an amino acid sequence which has at least 70% identity with amino acids 1 to 468 of SEQ ID NO:2;

(c) a polypeptide which is encoded by a polynucleotide that hybridizes under at least medium stringency conditions with (i) nucleotides 1 to 1548 of SEQ ID NO:1 or (ii) a complementary strand of (i); and (d) a fragment of amino acids 1 to 515 of SEQ ID NO:2, which has the glycosyltransferase activity as specified in (I) and/or (II).

A preferred embodiment relates to wherein the glycosyltransferase polypeptide of is:

(a) a polypeptide comprising an amino acid sequence which has at least 80% identity with amino acids 1 to 515 of SEQ ID NO:2; more preferably (a) a polypeptide comprising an amino acid sequence which has at least 90% identity with amino acids 1 to 515 of SEQ ID NO:2; even more preferably (a) a polypeptide comprising an amino acid sequence which has at least 95% identity with amino acids 1 to 515 of SEQ ID NO:2; and most preferably (a) a polypeptide comprising an amino acid sequence which has at least 98% identity with amino acids 1 to 515 of SEQ ID NO:2.

It may be preferred that the glycosyltransferase polypeptide of the first aspect is a polypeptide comprising an amino acid sequence with amino acids 1 to 515 of SEQ ID NO:2.

As discussed herein, the identified data/results of working Examples 4 show that herein relevant GT enzymes can be identified in e.g. *Sorghum* and rice plants.

The *Sorghum* polypeptide sequence (Genbank ID number: AAF17077.1) is shown as SEQ ID NO: 4 herein.

The rice polypeptide sequence (Genbank ID number: CAQ77160.1) is shown as SEQ ID NO: herein.

It may be relevant that the glycosyltransferase is a glycosyltransferase comprising an amino acid sequence which has at least 70% (preferably at least 80%, more preferably at least 90% and even more preferably at least 98%) identity with amino acids 1 to 492 of SEQ ID NO:4.

It may be relevant that the glycosyltransferase is a glycosyltransferase comprising an amino acid sequence which has at least 70% (preferably at least 80%, more preferably at least 90% and even more preferably at least 98%) identity with amino acids 1 to 471 of SEQ ID NO:5.

Alternatively, glycosyltransferases may also be a glycosyltransferase from a *Haworthia* plant.

Isolating the Aromatic Compound of Interest—Step (IV)

As discussed above, step (IV) of the first aspect reads: "isolating the aromatic aglycon compound of interest of step (II) and/or isolating the aromatic glycoside compound of interest of step (III) to get a composition, wherein the composition comprises less than 1% w/w dry matter of recombinant host cell material."

In the present context, the skilled person routinely know how to isolate a specific herein relevant aromatic compound of interest in relation to step (IV), i.e. it is not believed herein necessary to discuss this in great details.

In a preferred embodiment of the method as described herein is, wherein the isolated composition in step (IV) comprises aromatic glycoside compound of interest and wherein the aromatic glycoside compound of interest is flavokermesic acid glycoside (preferably DcII) and/or a kermesic acid glycoside (preferably carminic acid (CA)).

It may be preferred to have a relative pure composition, accordingly it may be preferred that composition comprising at least 10% w/w dry matter of the aromatic compound of interest and wherein the composition comprises less than 0.5% w/w dry matter of recombinant host cell material; or that composition comprising at least 50% w/w dry matter of the aromatic compound of interest and wherein the composition comprises less than 0.1% w/w dry matter of recombinant host cell material.

If there in step (IV) is obtained a composition comprising isolated aromatic aglycon compound of interest (e.g. flavokermesic acid (FK) or kermesic acid (KA)) the method of the first aspect may comprise an extra step of:

(IVa): glycosylating the aromatic aglycon compound of interest to produce an aromatic glycoside compound of interest.

This step may be done by chemical synthesis according to the art.

Alternatively, it may be done by use of a glycosyltransferase capable of glycosylating the aglycon under suitable conditions wherein there is produced the aglycon glycoside.

An embodiment of the invention relates to wherein the aromatic aglycon compound of interest of the isolated composition of step (IV) is flavokermesic acid (FK) and/or kermesic acid (KA) and the method of the first aspect comprises an extra step of: (IVa) contacting:

(a1): flavokermesic acid (FK) with a glycosyltransferase capable of glycosylating the flavokermesic acid under suitable conditions wherein there is produced the flavokermesic acid glycoside; and/or (a2): kermesic acid (KA) with a glycosyltransferase capable of glycosylating the kermesic acid under suitable conditions wherein there is produced the kermesic acid glycoside. In a preferred embodiment, the flavokermesic acid glycoside is DcII.

In a preferred embodiment, the kermesic acid glycoside is carminic acid (CA).

As discussed herein, the glycosyltransferase (GT) of this step may e.g. be the herein described GT from *Dactylopius coccus*.

Alternatively, it may e.g. be the herein discussed glycosyltransferases from *Aloe* plants, *Haworthia* plants, *Sorghum* and/or rice plants.

Aspects and Preferred Embodiments—in so-Called Claim Format/Language

Herein described aspect(s) and preferred embodiments thereof may be presented in so-called claim format/language. This is done below for some of the herein described aspect(s) and preferred embodiments thereof.

1. A method for producing an octaketide derived aromatic compound of interest, wherein the method comprises the following steps:

(I): contacting in vivo in a recombinant host cell comprising a recombinantly introduced Type III polyketide synthase (PKS) gene encoding an octaketide synthase (OKS) and wherein the OKS is of a different genus than the host cell:

(i): suitable starter unit and extender units with the recombinantly introduced OKS capable of converting the starter and extender units into a non-reduced octaketide under suitable conditions wherein there in vivo is produced the non-reduced octaketide; and (II): converting in vivo within the recombinant host cell the non-reduced octaketide of step (I) into a $C_{14}$-$C_{34}$ aromatic aglycon compound of interest, wherein the aromatic aglycon compound of interest is not SEK4 and/or SEK4B; and (III): optionally, the recombinant host cell also comprises a glycosyltransferase gene encoding a glycosyltransferase and the in step (II) produced aromatic aglycon compound of interest is in vivo glycosylated by the glycosyltransferase to produce a $C_{14}$-$C_{34}$ aromatic glycoside compound of interest; and (IV): isolating the aromatic aglycon compound of interest of step (II) and/or isolating the aromatic glycoside compound of interest of step (III) to get a composition, wherein the composition comprises less than 1% w/w dry matter of recombinant host cell material.

2. The method according to claim 1, wherein the recombinant host cell is a plant cell, a filamentous fungal cell, a yeast cell or a prokaryotic cell.

3. The method according to claim 2, wherein the recombinant host cell is a plant cell.

4. The method according to claim 3, wherein the plant cell is a plant cell selected from the group consisting of: *Nicotiana* sp. (e.g. *Nicotiana benthamiana* cells); rhubarb, buckweed, *Hypericum* and *Aloe* sp.

5. The method according to claim 4, wherein the plant cell is *Nicotiana* sp.

6. The method according to claim 5, wherein the plant cell is *Nicotiana benthamiana*.

7. The method according to claim 2, wherein the recombinant host cell is a filamentous fungal cell.

8. The method according to claim 7, wherein the filamentous fungal cell is *Acremonium, Aspergillus, Fusarium, Humicola, Mucor, Myceliophthora, Neurospora, Penicillium, Thielavia, Tolypocladium*, or *Trichoderma*.

9. The method according to claim 8, wherein the filamentous fungal cell is an *Aspergillus* cell.

10. The method according to claim 9, wherein the *Aspergillus* cell is *Aspergillus niger, Aspergillus oryzae* or *Aspergillus nidulans*.

11. The method according to claim 10, wherein the *Aspergillus* cell is *Aspergillus nidulans*.

12. The method according to any of the preceding claims, wherein the Type III polyketide synthase (PKS) gene of step (I) is a PKS gene from a plant, a bacterium or a fungi.

13. The method of claim 12, wherein the Type III polyketide synthase (PKS) gene of step (I) is a PKS gene from a plant.

14. The method of claim 13, wherein the plant is a plant selected from the group consisting of: *Aloe* spp. (preferably *Aloe arborescens*), *Hypericum* spp. (preferably *Hypericum perforatum*), rhubarb, buckweed and *Hawortia* spp.

15. The method of claim 14, wherein the plant is a plant selected from the group consisting of: *Aloe* spp. and *Hypericum* spp.

16. The method of claim 15, wherein the plant is a plant selected from the group consisting of: *Aloe arborescens* and *Hypericum perforatum*.

17. The method of claim 13, wherein the octaketide synthase (OKS) in step (I) of claim 1 is a OKS comprising an amino acid sequence which has at least 70% (preferably at least 80%, more preferably at least 90% and even more preferably at least 98%) identity with amino acids 1 to 403 of SEQ ID NO:7.

18. The method of claim 13, wherein the octaketide synthase (OKS) in step (I) of claim 1 is a OKS comprising an amino acid sequence which has at least 70% (preferably at least 80%, more preferably at least 90% and even more preferably at least 98%) identity with amino acids 1 to 403 of SEQ ID NO:9.

19. The method of claim 13, wherein the octaketide synthase (OKS) in step (I) of claim 1 is a OKS comprising an amino acid sequence which has at least 70% (preferably at least 80%, more preferably at least 90% and even more preferably at least 98%) identity with amino acids 1 to 405 of SEQ ID NO:11.

20. The method of claim 13, wherein the octaketide synthase (OKS) in step (I) of claim 1 is a OKS comprising an amino acid sequence which has at least 70% (preferably at least 80%, more preferably at least 90% and even more preferably at least 98%) identity with amino acids 1 to 403 of SEQ ID NO:13.

21. The method of claim 13, wherein the octaketide synthase (OKS) in step (I) of claim 1 is a OKS comprising an amino acid sequence which has at least 70% (preferably at least 80%, more preferably at least 90% and even more preferably at least 98%) identity with amino acids 1 to 393 of SEQ ID NO:15.

22. The method according to any of the preceding claims, wherein the suitable starter unit is acetyl-CoA and/or malonyl-CoA.

23. The method according to any of the preceding claims, wherein the suitable extender units is malonyl-CoA.

24. The method according to any of the preceding claims, wherein the:
  recombinant host cell is a host cell selected from the group consisting of: *Aspergillus* (preferably *Aspergillus nidulans*) and *Nicotiana* sp. (preferably *Nicotiana benthamiana*); and
  the OKS of a different genus than the host cell is an OKS selected from the group consisting of: OKS from *Aloe* spp. (preferably *Aloe arborescens*) and *Hypericum* spp. (preferably *Hypericum perforatum*).

25. The method according to any of the preceding claims, wherein the aromatic aglycon compound of interest is a $C_{14}$-$C_{18}$ aromatic aglycon compound of interest.

26. The method according to claim 25, wherein the aromatic aglycon compound of interest is at least one compound selected from the group consisting of: anthraquinone compound and anthrone compound.

27. The method of claim 26, wherein the aromatic aglycon compound of interest is an anthraquinone and the anthraquinone is flavokermesic acid (FK) or kermesic acid (KA).

28. The method according to claim 25, wherein the aromatic aglycon compound of interest is a $C_{16}$ aromatic aglycon compound of interest.

29. The method according to claim 28, wherein the $C_{16}$ aromatic aglycon compound of interest is flavokermesic acid (FK) or kermesic acid (KA).

30. The method according to any of the preceding claims, wherein the conversion in vivo in step (II) of claim 1 of the non-reduced octaketide into a $C_{14}$-$C_{34}$ aromatic aglycon compound of interest is done via involvement of at least one aromatase/cyclase.

31. The method according to claim 30, wherein the conversion in vivo in step (II) of claim 1 of the non-reduced octaketide into a $C_{14}$-$C_{34}$ aromatic aglycon compound of interest is done via involvement of at least one in trans acting (independent of the PKS enzyme) aromatase/cyclase.

32. The method of claim 31,
  wherein the aromatase/cyclase is a aromatase/cyclase comprising an amino acid sequence which has at least 70% (preferably at least 80%, more preferably at least 90% and even more preferably at least 98%) identity with amino acids 1 to 169 of SEQ ID NO:17 (*Streptomyces* ZhuI); and/or
  wherein the aromatase/cyclase is a aromatase/cyclase comprising an amino acid sequence which has at least 70% (preferably at least 80%, more preferably at least 90% and even more preferably at least 98%) identity with amino acids 1 to 256 of SEQ ID NO:19 (*Streptomyces* ZhuJ).

33. The method according to any of the preceding claims, wherein step (III) is fulfilled (i.e. not optional)—i.e. wherein step (III) is: the recombinant host cell also comprises a glycosyltransferase gene encoding a glycosyltransferase and the in step (II) produced aromatic aglycon compound of interest is in vivo glycosylated by the glycosyltransferase to produce a $C_{14}$-$C_{34}$ aromatic glycoside compound of interest.

34. The method of claim 33, wherein the aromatic glycoside compound of interest is a $C_{14}$-$C_{18}$ aromatic glycoside compound of interest.

35. The method of claim 34, wherein the aromatic glycoside compound of interest is a $C_{16}$ aromatic glycoside compound of interest.

36. The method of claim 35, wherein the $C_{16}$ aromatic glycoside compound of interest is a flavokermesic acid glycoside or a kermesic acid glycoside.

37. The method of claim 36, wherein the $C_{16}$ aromatic glycoside compound of interest is a flavokermesic acid glycoside and the flavokermesic acid glycoside is DcII.

38. The method of claim 36, wherein the $C_{16}$ aromatic glycoside compound of interest is a kermesic acid glycoside and the kermesic acid glycoside is carminic acid (CA).

39. The method according to any of the claims 33 to 38, wherein the glycosyltransferase
(GT) of step (III) is a GT from *Dactylopius coccus*, a GT from *Aloe* plants, a GT from *Haworthia* plants, a GT from *Sorghum* or a GT from rice plant.

40. The method of claim 36, wherein the glycosyltransferase (GT) is a glycosyltransferase polypeptide capable of:
(I): conjugating nucleotide activated glucose to flavokermesic acid (FK); and/or
(II): conjugating nucleotide activated glucose to kermesic acid (KA).

41. The method according to any of the claims 33 to 40, wherein the glycosyltransferase is a glycosyltransferase polypeptide capable of:
(I): conjugating nucleotide activated glucose to flavokermesic acid (FK); and/or
(II): conjugating nucleotide activated glucose to kermesic acid (KA);
and wherein the glycosyltransferase polypeptide is at least one polypeptide selected from the group consisting of:
(a) a polypeptide comprising an amino acid sequence which has at least 70% identity with amino acids 1 to 515 of SEQ ID NO:2;
(b) a polypeptide comprising an amino acid sequence which has at least 70% identity with amino acids 1 to 468 of SEQ ID NO:2;
(c) a polypeptide which is encoded by a polynucleotide that hybridizes under at least medium stringency conditions with (i) nucleotides 1 to 1548 of SEQ ID NO:1 or (ii) a complementary strand of (i); and
(d) a fragment of amino acids 1 to 515 of SEQ ID NO:2, which has the glycosyltransferase activity as specified in (I) and/or (II).

42. The method according to any of the claims 33 to 40, wherein the glycosyltransferase is a glycosyltransferase comprising an amino acid sequence which has at least 70% (preferably at least 80%, more preferably at least 90% and even more preferably at least 98%) identity with amino acids 1 to 492 of SEQ ID NO:4.

43. The method according to any of the claims 33 to 40, wherein the glycosyltransferase is a glycosyltransferase comprising an amino acid sequence which has at least 70% (preferably at least 80%, more preferably at least 90% and even more preferably at least 98%) identity with amino acids 1 to 471 of SEQ ID NO:5.

44. The method according to any of the claims 33 to 43, wherein the isolated composition in step (IV) comprises aromatic glycoside compound of interest and wherein the aromatic glycoside compound of interest is flavokermesic acid glycoside (preferably DcII) and/or a kermesic acid glycoside (preferably carminic acid (CA)).

45. The method according to claim 44, wherein the aromatic glycoside compound of interest is flavokermesic acid glycoside and the flavokermesic acid glycoside is DcII.

46. The method according to claim 44, wherein the aromatic glycoside compound of interest is kermesic acid glycoside and the kermesic acid glycoside is carminic acid (CA).

47. The method according to any of the preceding claims, wherein the isolated composition in step (IV) of claim 1 is comprising at least 10% w/w dry matter of the aromatic compound of interest and wherein the composition comprises less than 0.5% w/w dry matter of recombinant host cell material.

48. The method according to any of the preceding claims, wherein there in step (IV) is obtained a composition comprising isolated aromatic aglycon compound of interest (e.g. flavokermesic acid (FK) or kermesic acid (KA)) and the method then comprise an extra step of:
(IVa): glycosylating the aromatic aglycon compound of interest to produce an aromatic glycoside compound of interest.

49. The method of claim 48, wherein the glycosylating the aromatic aglycon compound of interest is done by use of a glycosyltransferase capable of glycosylating the aglycon under suitable conditions wherein there is produced the aglycon glycoside.

50. The method of claim 49, wherein the aromatic aglycon compound of interest of the isolated composition of step (IV) is flavokermesic acid (FK) and/or kermesic acid (KA) and the method of the first aspect comprises an extra step of:
(IVa): contacting:
(a1): flavokermesic acid (FK) with a glycosyltransferase capable of glycosylating the flavokermesic acid under suitable conditions wherein there is produced the flavokermesic acid glycoside; and/or
(a2): kermesic acid (KA) with a glycosyltransferase capable of glycosylating the kermesic acid under suitable conditions wherein there is produced the kermesic acid glycoside.

51. The method of any of claims 48 to 50, wherein the flavokermesic acid glycoside is DcII.

52. The method of any of claims 48 to 50, wherein the kermesic acid glycoside is carminic acid (CA).

53. The method of any of the preceding claims, wherein the recombinant host cell in claim 1 is a growing recombinant host cell and step (I) and step (II) of claim 1 are:
(I): contacting in vivo in a growing recombinant host cell comprising a recombinantly introduced Type III polyketide synthase (PKS) gene encoding an octaketide synthase (OKS) and wherein the OKS is of a different genus than the host cell:
(i): suitable starter unit and extender units with the recombinantly introduced OKS capable of converting the starter and extender units into a non-reduced octaketide under suitable growth conditions wherein there in vivo is produced the non-reduced octaketide; and
(II): converting in vivo within the growing recombinant host cell the non-reduced octaketide of step (I) into a $C_{14}$-$C_{34}$ aromatic aglycon compound of interest, wherein the aromatic aglycon compound of interest is not SEK4 and/or SEK4B.

EXAMPLES

Relevant sequence information can be found in herein provided Sequence Listing document

Example 1—Cloning of D. Coccus GT and Test of its FK and KA Activity

Materials and Methods
Purification of DNA and mRNA

Fresh frozen *Dactylopius coccus* (were obtained from Lanzarote). Fresh frozen *Porphyrophora polonica* were obtained from Poland. The frozen insects were ground into powder under liquid nitrogen and DNA/RNA was purified: DNA was purified using DNeasy Blood & Tissue kit (Qiagen), according to the protocol of the supplier. RNA was purified using RNeasy mini kit (Qiagen) according to the protocol of the supplier. Eucaryote mRNA was made into cDNA using $RT^2$ Easy First Strand Kit (Qiagen) according to the protocol of the supplier using poly-dT priming of the revers transcriptase reaction.

Sequencing of DNA and RNA:

DNA and cDNA were sent for sequencing at BGI (Shenzen, China) for sequencing using 100 bp paired-end Illumina technology according to the protocol of Illumina at a coverage of approximately 60-100× and the output in fastq data format.

Analysis of DNA and RNA/cDNA Sequences:

The obtained fastq-sequences of DNA and RNA/cDNA were imported into Genomic Workbench version 5.4 (CLC-bio, Arhus, Denmark) and assembled using the de novo assembling algorithm into contigs. Output files were exported as FASTA format. RNA/cDNA FASTA files were then imported into IOGMA v. 10 (Genostar, Grenoble, France) and putitative genes were identified using the "hidden Markov-Matrix-based prokaryote gene-finder.

Putative genes were annotated using BLAST (basic local alignment sequence tool) against genbank (NCBI) using as well the nucleotide sequence as the translated protein sequence. The putative genes were also annotated by similarity comparison to PFAM databases of protein families.

Preparation of Protein Fractions from *D. Coccus*

Three grams of fresh *D. coccus* insects were homogenized in 120 mL of isolation buffer [350 mM sucrose, 20 mM Tricine (pH 7.9), 10 mM NaCl, 5 mM DTT, 1 mM PMSF) containing 0.3 g polyvinylpolypyrrolidone. The homogenate was filtered through a nylon cloth (22 μm mesh) and centrifuged for (10 min, 10,000×g at 4° C.). The supernatant was centrifuged (1 h, 105,000×g, at 4° C.), yielding a soluble and a membrane bound protein fraction. The soluble protein fraction was concentrated to 1 mL and buffer-exchanged with 20 mM Tricine (pH 7.9), 5 mM DTT by using Amicon ultrafugation-3K devices (Millipore). The membrane bound protein pellet was washed 3 times by resuspending the pellet in 60 mL of 20 mM Tricine (pH 7.9), 5 mM DTT using a marten paintbrush followed by re-centrifugation. The membrane bound protein pellet was finally resuspended in 1 mL 20 mM Tricine (pH 7.9), 5 mM DTT. The soluble protein fraction and the membrane bound protein fraction were analyzed for glycosylation activity.

Purification of a Flavokermesic Acid/Kermesic Acid-Specific GT Activity from *D. Coccus* Membrane Proteins A membrane bound protein fraction isolated from 3 g fresh *D. coccus* insects was solubilized by adding 1% (v/v) Triton x-100 (reduced form) and gently stirring for 1.5 h in the cold. The Triton x-100 treated solution was centrifuged (1 h, 105,000×g, at 4° C.) and the supernatant was isolated and applied to a column packed with 2 mL Q-sepharose Fast flow (Pharmacia). The column was washed in 4 mL of buffer A [20 mM Tricine (pH 7.9), 0.1% (v/v) Triton x-100 (reduced form), 50 mM NaCl] and proteins were eluted with 20 mM Tricine (pH 7.9), 0.1% (v/v) Triton x-100 (reduced form) using a discontinuous NaCl gradient from 100 mM-500 mM, (with 50 mM increments). 0.5-ml-fractions were collected, desalted, analyzed by SDS-PAGE and monitored for glucosylation activity using the described radiolabeled glucosylation enzyme assay. A fraction containing enriched flavokermesic acid/kermesic acid-specific GT activity was subjected to peptide mass fingerprinting analysis.

Enzyme Assays and Glucoside Product Detection

Glucosylation of flavokermesic acid and kermesic acid was performed in assay mixtures of 60 μL containing 20 mM Tricine (pH 7.9), 3.3 μm UDP[14C]glucose and 20 uL protein extract (membrane bound or soluble protein). Reactions were incubated for 0.5 h at 30° C. and terminated by adding 180 μL of methanol. Samples were centrifuged at 16,000×g for 5 min at 4° C. and supernatant was spotted on TLC plates (silica gel 60 F254 plates; Merck). Assay products were resolved in dichloromethane:methanol:formic acid (7:2:2, by volume). Radiolabeled products were visualized using a STORM 840 PhosphorImager (Molecular Dynamics).

Expression of Codon Optimized DcUGT2, DcUGT4 and DcUGT5 in *S. cerevisiae*

A synthetic codon optimized version of DcUGT2 and two other putative GT sequences from the *Dactylopius coccus* transcriptome termed DcUGT4 and DcUGT5 for yeast expression was purchased from GenScript with flanking gateway recombination attL sites. The synthetic fragments were used as PCR templates with specific primers to generate the corresponding C-terminal Strepli-tagged versions. The six gene constructs (tagged and non-tagged fragments) were cloned into the gateway destination plasmid pYES-DEST52 (Invitrogen) using LR clonasell enzyme mix. The six pYES-DEST52 plasmid constructs were transformed separately into the Invscl yeast strain (Invitrogen) and positive transformants were verified by PCR. Heterologous protein production was performed according to the instructions of the pYES-DEST52 gateway vector (Invitrogen). Production of heterologous Strepli-tagged protein was verified by western blotting using anti-Strep antibody. A membrane bound protein fraction was prepared from verified yeast transformants as described in (D. Pompon, B. Louerat, A. Bronine, P. Urban, Yeast expression of animal and plant P450s in optimized redox environments, Methods Enzymol. 272 (1996) 51-64) and screened for glucosylation activity towards flavokermesic acid/kermesic acid. The yeast optimized sequence is shown in SEQ ID NO: 3 herein.

LC-MS-MS

LC/MS was performed on an Agilent Q-TOF with the following HPLC system:

Column Kinetix 2.6p XB-C18 100A (100×4.60 mm, Phenomenex). Solvent A (900 ml deionized water, 100 ml methanol and 50 ml formic acid). Solvent B (700 ml methanol, 300 ml deionized water and 50 ml formic acid).

Flow 0.8 ml/min. 35° C.

Gradient elution. 0-1 min 100% A. Linear gradient to 83% A 3 min. linear gradient to 63% A 6 min, linear gradient to 45% A 9 min, linear gradient to 27% A 12 min, linear gradient to 10% A 15 min, linear gradient to 3% A 17 min, linear gradient to 2% A 19 min, linear gradient to 0% A 20 min, 0% A 22 min, linear gradient to 100% A 25 min.

Retention times were 7.6 min for carminic acid, 7.8 min for DC II, 13.7 min for flavokermesic acid and 13.9 min for kermesic acid.

Results:

The ability to glycosylate flavokermesic acid/kermesic acid using $C_{14}$-UDP-glucose as a substrate was detected in homogenized *D. coccus* insects. The activity was shown to be membrane bound and the activity was purified and the purified proteins were submitted to proteomics analysis. It was shown that the enzymatic activity was to come from a polypeptide with a sequence corresponding to our candidate gene DcUGT2.

As discussed above, the herein relevant glycosyltransferase enzyme of SEQ ID NO: 2 may herein be termed "DcUGT2".

The amino acid sequence of DcUGT2 shows less than 45% homology to any known glycosyl transferase.

Knowing that cloning the wildtype sequence into yeast had given no relevant enzyme activity, we redesigned the nucleotide sequence of DcUGT2 to a sequence coding for the same polypeptide but using nucleotide codons optimized for *S. cerevisiae*, a process called codon optimization (the *S. cerevisiae* optimized sequence is shown as SEQ ID No. 3 herein). Subsequently, the codon optimized sequence of DcUGT2 was cloned and expressed in yeast. The heterologous yeast strain contains a membrane bound enzyme activity capable of glucosylating kermesic acid and flavokermesic acid.

After obtaining peptide mass fingerprinting data from a *Dactylopius coccus* protein fraction enriched with GT activity towards flavokermesic acid/kermesic acid, we matched the peptide masses to the transcriptomic dataset and identified three putative UGTs (DcUGT2, DcUGT4 and DcUGT5).

Heterologous expression of the three candidates in yeast revealed that only one of these UGTs, namely DcUGT2 was responsible for the observed glucosylation activity towards flavokermesic acid/kermesic acid in the *D. coccus* protein fraction.

A viscozyme treatment of the generated C-14 radiolabelled glucoside, showed that it was resistant towards hydrolysis, further suggesting that the DcUGT2 is a C-GT, responsible for producing DCII and carminic acid.

A LC-MS-MS showed formation of products with the same retention time, spectrum, molecular mass and molecular degradation pattern as DcII and carminic acid respectively.

CONCLUSION

The result of this Example 1 demonstrated that it was not an easy task to isolate/clone the herein relevant glycosyltransferase enzyme of SEQ ID NO: 2, which may herein be termed "DcUGT2" or simply "DcUGT".

For instance, the identified gene sequences of the genome and transcriptome of *D. coccus* insects were analyzed for similarity to herein relevant public known C-glycosyltransferase sequences and the result was negative in the sense that none of the identified gene sequences of the genome/transcriptome showed herein significant similarity to publicly known herein relevant C-glycosyltransferase sequences.

However, even though the bioinformatic sequence similarity analysis could be said to indicate that the genome of *Dactylopius coccus* would not comprise a gene encoding a herein relevant glycosyltransferase—the present inventors continued to investigate the matter and the present inventors identified a *Dactylopius coccus* extract (including extracts of the endosymbionts present in *D. coccus*) with herein relevant GT activity and by a combination of herein relevant purification and testing steps the inventors were finally able to get a relatively pure fraction/composition wherefrom it was possible to obtain several partial amino acid sequences of possible GT enzyme candidates.

The present inventors tested the activity of the herein described isolated/cloned novel glycosyltransferase of SEQ ID NO: 2 (DcUGT2) and found that it was able to conjugate glucose to the aglycons flavokermesic acid (FK) and kermesic acid (KA)—see FIG. 1 herein.

Example 2 Testing KA GT Activity of Prior Art Known UrdGT2

As discussed above, the UrdGT2 is described in the article Baig et al (Angew Chem Int Ed Engl. 2006 Nov. 27; 45(46):7842-6).

As discussed above, this article describes that UrdGT2 is capable of glycosylating different aglycon molecules that may be considered structurally similar to the herein relevant Kermesic acid (KA) and Flavokermesic acid (FK) aglycons.

A codon optimized synthetic version of UrdGT2 for *E. coli* expression was cloned and recombinantly expressed in *E. coli*. A crude soluble protein extract containing the the recombinant UrdGT2 was obtained, i.e. an extract comprising the UrdGT2

The UrdGT2 GT activity was analyzed in vitro using either UDP-glucose or TDP-glucose as a sugar donor and FA/KA as aglycone substrates. No activity was detected towards these aglycons, i.e. no herein relevant GT activity was identified in relation to these aglycons.

However, it was confirmed that the recombinant UrdGT2 was active, as demonstrated by the in vitro formation of a C14-radiolabelled glucoside derived from the glucosylation of an unidentified compound in the crude *E. coli* extract.

Example 3 GT Activity in *Aloe* Plant and *Haworthia* Plant

Isolation and Test of GT Activity from *Aloe*
1) The plant was washed from soil particles and separated into: A) Root, B) Green leaf tissue and C) the gel material from the leaf
2) 5 g of tissue was frozen immediately in liquid nitrogen and ground in a cold mortar with a pestle to a fine powder.
3) 20 mL of cold extraction buffer [20 mM Tricine-HCl, 10 mM NaCl, 5 mM DTT, 1 mM PMSF, pH 7.9] containing a Complete protease inhibitor without EDTA (Roche), 0.1% (w/v) proteamine sulfate and 0.5 g of PVPP were added to the powder and vortexed.
4) The homogenate was gently stirred at 4° C. for 10 min and then centrifuged at 12,000×g at 4° C. for 5 min.
5) Supernatant was isolated and 1 mL of 2% (w/v) proteamine sulfate in 20 mM Tricine-HCl, pH 7.9 was added dropwise over 2 min at 4° C. under constant stirring.
6) The supernatant was filtered through 2 pieces of nylon mesh. The filtered supernatant was then centrifuged at at 12,000×g at 4° C. for 5 min.
7) The supernatant was isolated and ultracentrifuged at 110,000×g at 4° C. for 1 h.
8) The soluble protein fraction (supernatant) was isolated and buffer-exchanged 5 times with 20 mM Tricine-HCl, pH 7.9 containing 5 mM DTT using a Amicon Ultra centrifugal filter device-3K (Millipore)
9) 20 µL soluble protein extract was incubated in a total reaction volume of 60 µL containing UDP-glucose (1.25 mM final conc.) and either FK (50 µM final conc.), KA (50 µM final conc) or MeO-FK/EtO-FK (50 µM/50 µM final conc) for 2 h at 30° C., shaking at 650 rpm.
10) Enzyme reactions were terminated with 180 µL cold methanol and filtered through a 0.45 micron filter and subjected to HPLC-MS analysis.

TABLE 1

Glucosides formed in in vitro glucosylation assays using enzyme extracts from *Aloe*.

| Aloe | m/z [M − H]⁻ values | | | |
|---|---|---|---|---|
| Soluble protein | 475 m/z [M − H]⁻ FK-monoglc | 491 m/z [M − H]⁻ KA-monoglc | 489 m/z [M − H]⁻ MeOFK-monoglc | 503 m/z [M − H]⁻ EtOFK-monoglc |
| Leaf | 3.73 | 3.71 | 5.81 | 6.63 |
| Gel | | | | |
| Root | | 3.71 | | |

Crude soluble enzyme extracts of three *Aloe* tissues, green leaf material (Leaf), gel material from the leaf (Gel) and Root were tested for glucosylation activity towards flavokermesic acid (FK), kermesic acid (KA), methyl ester of flavokermesic acid (MeOFK) and ethyl ester of flavokermesic acid (EtOFK). Numbers correspond to retention times (min) after HPLC-MS separation of the novel glucosides formed in vitro (Table 1).

The m/z values 475 and 491 are the same m/z values as are obtained for DcII and CA, respectively, solubilized in similar solutions. Both m/z values are 162 (m/z value of glucose in a glucoside) higher than the m/z values of the FK and KA indicating that the glucose moiety from UDP-glucose in the reaction buffer has been transferred to the aglycone by a GT in the extract. The m/z [M-H] values 489 and 503 are also 162 higher than the m/z values obtained with MeOFK and EtOFK, respectively, indicating that a glucose unit has been added to both MeOFK and EtOFK by a GT present in the extract.

Isolation and Test of GT Activity from *Haworthia limifolia*

The procedure was as described for *Aloe* but plant tissue analyzed were following: A) Green leaf tissue, B) Gel material from the leaf, C) Base tissue (pink part between root and stem) and D) Root tissue.

Crude soluble enzyme extracts of four *Haworthia limifolia* tissues, green leaf material (Leaf), gel material from the leaf (Gel), pink tissue between root and stem (Base) and Root were tested for glucosylation activity towards flavokermesic acid (FK), kermesic acid (KA), methyl ester of flavokermesic acid (MeOFK) and ethyl ester of flavokermesic acid (EtOFK). Numbers correspond to retention times (min) after HPLC-MS separation of the novel glucosides formed in vitro (Table 2).

TABLE 2

Glucosides formed in in vitro glucosylation assays using enzyme extracts from *Haworthia limifolia*.

| Haworthia | m/z [M − H]⁻ values | | | |
|---|---|---|---|---|
| Soluble protein | 475 m/z [M − H]⁻ FK-monoglc | 491 m/z [M − H]⁻ KA-monoglc | 489 m/z [M − H]⁻ MeOFK-monoglc | 503 m/z [M − H]⁻ EtOFK-monoglc |
| Leaf | 3.73 | 3.71 | 5.81 | 6.63 |
| Gel | | | | |
| Base | 3.73 | 3.71 | 5.81 | 6.63 |
| Root | 3.73 | 3.71 | 5.81 | 6.63 |

The m/z values 475 and 491 are the same m/z values as are obtained for DcII and CA, respectively, solubilized in similar solutions. Both m/z values are 162 (m/z value of glucose in a glucoside) higher than the m/z values of the FK and KA indicating that the glucose moiety from UDP-glucose in the reaction buffer has been transferred to the aglycone by a GT in the extract. The m/z [M-H] values 489 and 503 are also 162 higher than the m/z values obtained with MeOFK and EtOFK, respectively, indicating that a glucose unit has been added to both MeOFK and EtOFK by a GT present in the extract.

CONCLUSION

The results of this example demonstrate that herein relevant glycosyltransferase (GT) enzymes can be identified in *Aloe* plants and *Haworthia* plants.

Said in other words, *Aloe* plants and *Haworthia* plants comprise a glycosyltransferase which is capable of glycosylating flavokermesic acid in order to produce flavokermesic acid glycoside; and/or capable of glycosylating kermesic acid in order to produce kermesic acid glycoside.

Example 4 GT Activity in *Sorghum* and Rice Plant

As known the art, *Sorghum* and rice plants comprise glycosyltransferases.

As known in the art, some of the *Sorghum* and rice glycosyltransferases may glycosylate low molecular weight aglycone compounds.

The in the art described glycosyltransferases from *Sorghum* and rice plants have significant less than 70% identity with amino acids 1 to 515 of SEQ ID NO:2 as disclosed herein.

It is not known in the art if glycosyltransferases of *Sorghum* and/or rice plants would be a herein relevant glycosyltransferase, i.e. a glycosyltransferase which is capable of glycosylating flavokermesic acid in order to produce flavokermesic acid glycosides; and/or capable of glycosylating kermesic acid in order to produce kermesic acid glycosides.

The known glycosyltransferases from *Sorghum* (*Sorghum bicolor*), SbUGT85B1, with Genbank ID number AF199453.1 (nucleotide seq.)/AAF17077.1 (polypeptide seq) and rice (*Oryza sativa*), OsCGT, with Genbank ID number FM179712.1 (nucleotide seq.)/CAQ77160.1 (polypeptide seq) were expressed in *E. coli* strain Xjb and crude *E. coli* proteins extracts were prepared and tested for glucosylation activity on the substrates kermesic acid and flavokermisic acid as described by Kannangara et al. (2011) and Augustin et al. (2012).

FIG. 2 in PCT/EP2014/078540 (PCT filing date 18 Dec. 2014) shows in LC-MS analyses of glucosylated products formed in assays containing crude lysate of *E. coli* strain Xjb expressing either SbUGT85B1 or OsCGT, UDP-glucose and flavokermesicc acid (FK) or kermesic acid (KA). As a negative control crude extract from the *E. coli* strain Xjb was used in the assays.

There were identified KA glycosides (491 m/z [M-H]–the m/z[M-H] value of CA) for both glycosyltransferases and FK glycosides (475 m/z [M-H] the m/z[M-H] value of DcII) for OsCGT.

CONCLUSION

The result of this example demonstrated that herein relevant glycosyltransferase (GT) enzymes can be identified in *Sorghum* and/or rice plants.

Said in other words, *Sorghum* and/or rice plants comprise a glycosyltransferase which is capable of glycosylating flavokermesic acid in order to produce flavokermesic acid glycoside; and/or capable of glycosylating kermesic acid in order to produce kermesic acid glycoside.

Example 5 Use of Endogenous GT Gene or GT Activity

As known in the art glycosyltransferases able to glycosylate low molecular weight are present in a lot of different organisms. A method to contact the glycosyltransferase of the cells of an organism with a low molecular weight compound is to introduce one or more genes directing the biosynthesis of the low molecular weight compound and thus enabling the cells to glycosylate the low molecular weight compound. The low molecular weight compound may be e.g. flavokermesic acid or kermersic acid or decorated versions of these molecules.

One or more genes directing the biosynthesis of flavokermesic acid or kermesic acid or decorated version of these molecules are introduced into a glycosyltransferase containing organism, e.g. the tobacco plant, *Nicotiana benthamiana*.

When the gene/genes is/are transiently expressed according to the methods described in (D'Aoust et al. (Methods Mol Biol 483 (2009): 41-50) in e.g. plant tissue the low molecular weight compound or compounds is/are produced. Cells stably expressing the gene/genes are produced and selected according to the methods described in Gelvin (Microbiol Mol Biol Rev 67(1) (2003): 16-37)).

In cells containing either stably expressed and/or transiently expressed gene/genes the low molecular weight compounds come into contact with the endogenous glycosyltransferases, resulting in the formation of one or more glycosides of flavokermesic acid, kermesic acid or decorated versions of these molecules.

The presence of the glycosides is demonstrated by the extraction and the analytical methods described in Example 3.

Samples are prepared for LC/MS by the method for extraction described by (Rauwald and Sigler (Phytochemical Analysis 5 (1994):266-270).

CONCLUSION

The results of this example demonstrate that endogenous glycosyltransferases present in the cells of a recombinant organism can be used to convert flavokermesic acid, kermesic acid or decorated versions of these molecules into glycosides when a gene/genes directing the biosynthesis of the aglycons are introduced into the organism.

Said in other words introduction of a gene or genes directing the biosynthesis of flavokermesic acid, kermesic acid, decorated versions of these molecules, or related low molecular weight compounds is a method to bring the low molecular weight compound in contact with glycosyltransferases and thus a method to produced glycosides of flavokermesic acid, kermesic acid or decorated version of these compounds.

Example 6: Stable Expression of Type III PKSs in *Aspergillus nidulans*

Materials and Methods
Media and Solutions

All solutions were prepared with Milli-Q $H_2O$ and sterilized at 121° C. for 20 min.

Trace Element Solution: For 1 L mix 0.4 g $CuSO_4.5H_2O$; 0.04 g $Na_2B_4O_7.10H_2O$; 0.8 g $FeSO_4.7H_2O$; 0.8 g $MnSO_4.2H_2O$; 0.8 g $Na_2MoO_4.2H_2O$; and 8.0 g $ZnSO_4.7H_2O$.

Mineral Mix (50×): For 1 L solution mix 26 g KCl; 26 g $MgSO_4.7H_2O$; and 76 g $KH_2PO_4$; and 50 ml Trace element solution.

20× Nitrate Salts Solution: For 1 L solution: dissolve 120 g $NaNO_3$, 10.4 g KCl, 10.4 g $MgSO_4.H_2O$, 30.4 g $KH_2PO_4$ in Milli-Q water.

Trace element solution (1 L stock solution): For 1 L solution: dissolve 0.4 g $CuSO_4$. $5H_2O$, 0.04 g $Na_2B_4O_7.10H_2O$, 0.8 g $FeSO_4.7H_2O$, 0.8 g $MnSO_4.2H_2O$, 0.8 g $Na_2MoO_4$. $2H_2O$, 8 g $ZnSO_4.7H_2O$, up to 1 L Milli-Q water.

Thiamine 1%: Final concentration 0.001%.

D-Glucose 20% (w/Vol): For 1 L solution 200 g D-glucose in Milli-Q water

*Aspergillus* Protoplastation Buffer (APB): Final concentration 1.1 M $MgSO_4$ and 10 mM Na-phosphate buffer. pH is adjusted with 2 N NaOH to 5.8.

*Aspergillus* Transformation Buffer (ATB): Final concentrations: 1.2 M Sorbitol; 50 mM $CaCl_2.2H_2O$; 20 mM Tris; and 0.6 M KCl. pH is adjusted with 2 N HCl to 7.2.

PCT: Final concentration: 50% w/vol PEG 8000 (4000, 6000 and other PEG can also be used); 50 mM $CaCl_2$); 20 mM Tris; and 0.6 M KCl. pH is adjusted with 2 N HCl to 7.5.

Minimal Media (MM): For 1 L of solution: 1 ml Trace elements; 50 ml nitrate salts (1M); 50 ml 20%-w/vol glucose; 1 mL Thiamine; 20 g Agar (So.Bi gel). For liquid MM Agar is not added.

Supplements to the Media: Supplements were added to the different media if necessary, based on the genotype of the *Aspergillus nidulans* strain, in the following amounts: Arginine 4 mM, uracile 10 mM and uridine 10 mM. For counter selection of the AfpyrG marker 5-fluororotic acid (5-FOA) is added to a concentration of 1.3 mg/mL.

Solid Transformation Media (TM): For 1 L of solution: 1 ml Trace elements; 50 ml nitrate salts (1M); Sucrose 171.15 g; 1 mL Thiamine; 20 g Agar (So.Bi gel). For liquid MM Agar is not added.

Transformation of *Aspergillus nidulans*

*Aspergillus nidulans* protoplasts were generated following a standard protocol of the prior art, shortly summarized here: *Aspergillus nidulans* macromedia are geminated overnight, and the resulting biomass was harvested by filtering through a Miracloth filter (Merck Millipore). The mycelium was re-suspended in 10 ml APB buffer containing 40 mg Glucanex/ml (Novozymes A/S). The mixture was incubated on a shaker at 37° C. with 150 rpm for 3 hours. APB was added to yield a total volume of 40 ml. An overlay of 5 ml 50% ATB and 50% MQ-water was applied and the tubes were centrifuged at 3000 RCF, 16° C., for 12 minutes resulting in a two-phase system with the protoplast in the interphase. The protoplasts were washed using 40 ml of ATB and centrifugation at 3000 RCF, 16° C., for 12 minutes. The resulting pellet was re-suspended in 1 ml ATB.

The resulting protoplasts were used for genetic transformation experiments in aliquots of 50 µl mixed with 1.5-5 µg DNA and 150 µL PCT. The transformation mixture was incubated for 10 minutes. The mixture was then added 250 µL ATB and transferred to a transformation plate with required supplements dispatched with a Drigalski spatula.

Following incubation for 4 days at 37° C., the resulting *Aspergillus nidulans* transformants were isolated and subcultured on individual agar plates with a suitable selection regime. Targeted integration of the expression cassette was analyzed by PCR using the original primers used for amplifying the gene to be expressed, followed by primer pairs with one primer annealing inside the insert and one in the surrounding genome. In the case of AfpyrG based strains, the selection marker was eliminated, following the transformation, by counter selection on 5-FOA containing plates and homologous recombination between short directional repeats surrounding the AfpyrG marker gene in the expression cassette. Following removal of the marker gene, the strain was again verified by diagnostic PCR. Removal of the selection marker gene allowed for a subsequent transformation round with a new target gene, using the same selection marker gene as used during the first transformation.

Construction of the *Aspergillus nidulans* Host Strains

The used *Aspergillus nidulans* strains are listed in Table 3 below and Table 4 summarizes the modified loci/genes. Targeted gene deletion (or replacement) was achieved by constructing gene targeting cassettes, consisting of a recyclable selection marker gene surrounded by two ap. 1500 bp sequences identical to the sequences surrounding the locus that should be replaced in the genome. The targeting construct for replacement of the wA and yA genes were constructed via the split-marker PCR-based method described in (Nielsen M. L., Albertsen L., Lettier G., Nielsen J. B., Mortensen M. H., 2006. Efficient PCR-based gene targeting with a recyclable marker for *Aspergillus nidulans*. Fungal Genetics and Biology, Vol. 43:54-64). First the wA gene was targeted for deletion and the required targeting sequences were amplified from genomic DNA using the primers: ANwA-dl-Up-F (5'-GGAAGAAGGTCGCATACCA-3'; SEQ ID NO:34) combined with ANwA-dl-Up-Rad (5'-gatccccgggaattgccatgGATCAGGAGAAGGAGAGT-CAAG-3'; SEQ ID NO:35) and ANwA-dl-Dw-Fad (5'-aattccagctgaccaccatgGGCGAAAAGGCAAAGGAGC-3'; SEQ ID NO:36) combined with ANwA-dl-Dw-R (5'-GCTA-GAAAAGGCAAGGGAGG-3'; SEQ ID NO:37). The two marker fragments were amplified by combining the M1 primer (5'-catggcaattcccggggatc-GCCG-GCAATTTCTTTTTTAGGTAGC-3'; SEQ ID NO:38) combined with the M2 primer (5'-CCAGAAGCAGTA-CACGGC-3'; SEQ ID NO:39) and the M3 primer (5'-GTTGTCTGCTTGCGCTTCTTC-3'; SEQ ID NO:40) with the M4 primer (5'-catggtggtcagctggaatTCCTCCGC-CATTTCTTATTCCC-3'; SEQ ID NO:41). Following PCR amplification of the gene targeting and marker DNA fragments the fragments were fused by PCR, as described in Nielsen et al. 2006, the DNA fragments were gel purified and transformed into the recipient *Aspergillus nidulans* strain NID1 (described in Nielsen J. B, Nielsen M. L., Mortensen U. H, 2008, Transient disruption of non-homologous end-joining facilitates targeted genome manipulations in the filamentous fungus *Aspergillus nidulans*. Fungal Genetics and Biology, Vol. 45:165-170). The marker in the resulting strain was eliminated by counter selection on 5-FOA plates to identify transformants where the AfpyrG marker gene had looped out spontaneously. Targeted deletion of the yA gene was conducted as described for the wA gene, but using the following two primer pairs for amplifying the targeting sequences: Del-yA-5'-F (5'-GTGGGTT-GAACCGCTTACTCAG-3'; SEQ ID NO:42) combined with Del-yA-5'-R (5'-gatccccgggaattgccatg-CCCGGAG-GAATCAAAATGACGC-3'; SEQ ID NO:43) and Del-yA-3'F (5'-aattccagctgaccaccatgGTTTGGGATTCTTAGGT-GAGCTC-3'; SEQ ID NO:44) combined with Del-yA-3'-R (5'-CCTCCCTGGCGTATACACAAAC-3'; SEQ ID NO:45). The resulting AfpyrG marker free strain is referred to as NID598 in the subsequent description.

Targeted deletion of the asperthecin PKS (aptA) was performed in the NID598 background, using the experimental strategy described for the yA and wA gene deletions. The two targeting DNA fragments were PCR amplified using the primer AnAptA-UP-F (5'-GCTCGAGCTTGCCAGCC-3'; SEQ ID NO:46) combined with AnAptA-UP-R (5'-gatc-cccgggaattgccatg-GCTGGTGTTGGGACACACG-3'; SEQ ID NO:47) and the AnAptA-Dw-F (5'-aattccagctgaccaccatg-GCTTGGAAATCAGTATAGCTTTCTG-3'; SEQ ID NO:48) combined with AnAptA-Dw-R (5'-GCTTGTG-GTCTGTCTGAATCG-3'; SEQ ID NO:49). The gel purified targeting construct was then transformed into the marker free NID598 strain, resulting in the strain NID930.

The Apt-cluster, mdp-cluster and stc-clusters were sequentially deleted in the NID598 background. For this, the required targeting constructs were constructed via directional Uracil-Specific Excision Reagent Cloning (USER) of the respective targeting fragments into the P1(P6) vector, as described in (Hansen B. G., Salomonsen B., Nielsen M. T., Nielsen J. B., Hansen N. B., Nielsen K. F., Regueira T. B., Nielsen J., Patil K. R., Mortensen U. H. 2011. Versatile enzyme expression and characterization system for *Aspergillus nidulans*, with the *Penicillium* brevicompactum polyketide synthase gene from the mycophenolic acid gene cluster as a test case. Appl Environ Microbiol. Vol. 77(9): 3044-51). For deletion of the Apt-cluster the targeting fragments were amplified with the primers ANAPTcluster-Dl-Up-FU (5'-GGGTTTAAdUGAGGAGCAGAGGATGCGG-3'; SEQ ID NO:90) combined with ANAPTcluster-Dl-Up-RU (5'-GGACTTAAdUGTAGTGGTGGTGCTGGTG-3'; SEQ ID NO:91) and ANAPTcluster-Dl-Dw-FU (5'-GGCAT-TAAdUCGCGTGGAATTTGGAAGAGAG-3'; SEQ ID NO:92) combined with ANAPTcluster-Dl-Dw-RU (5'-GGTCTTAAdUGTGCTCGGGGACGTGAAAG-3'; SEQ ID NO:93). The used primers each included a 2-deoxyuridin (dU) based to allow for the creation of 3' overhangs. The resulting PCR fragments were gel purified and directionally cloned by USER cloning into the PacI/Nt.BbvCI digested P1(P6) vector. The resulting plasmid was SwaI digested to liberate the targeting fragment, including the AfpyrG marker. The digested plasmid was transformed into the marker-free NID598 strain. The AfpyrG marker was subsequently removed by 5-FOA counter selection, as described for wA above, to prepare the strain for deletion of the mdp-cluster. Targeted deletion of the mdp and stc clusters were conducted as described for the apt cluster. For construction of the targeting sequence for the mdp-cluster was PCR amplified using the ANMDPcluster-Dl-Up-FU (5'-GGGTTTAAdUGGTCGTCTGTCAAGGAGTTG-3'; SEQ ID NO:94) primer combined with the ANMDPcluster-Dl-Up-RU (5'-GGACTTAAdUGCAGTGCTG-TATATGGGTCTTG-3'; SEQ ID NO:95) primer and the ANMDPcluster-Dl-Dw-FU (5'-GGCATTAAdUGAGTTT-GTGAGATGTTCAGGATGG-3'; SEQ ID NO:96) primer combined with the ANMDPcluster-Dl-Dw-RU (5'-GGTCT-TAAdUGAGGTGAAGGACACAGCG-3'; SEQ ID NO:97) primer. Moreover, the targeting sequence for the stc cluster were PCR amplified with the primers; ANSTCcluster-Dl-Up-FU (5'-GGGTTTAAdUCGCAGAGACTAGGACA-CAAGTG-3'; SEQ ID NO:98) combined with ANSTCcluster-Dl-Up-RU (5'-GGACTTAAdUGCGGCGATCTGTGGTAGAG-3'; SEQ ID NO:99) and ANSTCcluster-Dl-Dw-FU (5'-GGCAT-TAAdUGCCAGCATATTCAAACCCAGTC-3'; SEQ ID NO:100) combined with ANSTCcluster-Dl-Dw-RU (5'-GGTCTTAAdUCACACAACCAACCTCCGATC-3'; SEQ ID NO:101). The resulting strain with the deletion of the apt, mdp and stc clusters is referred to as NID_SMA.

TABLE 3

The different Aspergillus nidulans strains used in the study

| Strain name | Genotype |
| --- | --- |
| NID1 | nkuAΔ, argB2, pyrG89, veA1 |
| NID598 | nkuAΔ, argB2, pyrG89, veA1, wAΔ, yAΔ |
| NID930 | nkuAΔ, argB2, pyrG89, veA1, wAΔ, yAΔ, aptAΔ |
| NID_SMA | nkuAΔ, argB2, pyrG89, veA1, wAΔ, yAΔ, aptΔ, mdpΔ, stcΔ |

TABLE 4

The affected genes

| Gene names and accession numbers in the Aspergillus-genome-database: | |
| --- | --- |
| yA = AN6635 | Ascospore pigment biosynthesis (Laccase) |
| wA = AN8209 | Ascospore pigment biosynthesis (PKS) |
| aptA = AN6000 | Asperthecin PKS |
| apt = aptA (AN6000) to aptC (AN6002) | Asperthecin gene cluster |
| mdp = mdpL (AN10023) to mdpA (AN10021) | Monodictyphenone/emodin gene cluster |
| stc = stcW (AN7804) to stcA (AN7825) | Sterigmatocystin gene cluster |

Expression of Type III PKS in Aspergillus nidulans

Synthetic (de novo synthesized) codon optimized versions of HpPKS2, AaOKS were made for yeast expression, and sequences with the natural codon usage were purchased from Genscript. Codon optimized genes are denoted with a 'ScOpt' suffix, e.g. HpPKS2-ScOpt, while genes with the original codon usage from the natural host is denoted with an 'Orig' suffix, e.g. HpPKS2-Orig. The synthetic DNA fragments were used as PCR template for PCR reactions with specific primers (IDT) for the coding sequences of the genes including stop codons. The used primers contained 5' overhangs compatible with Uracil Specific Excision Reagent (USER™) cloning of the resulting PCR amplicons into expression vectors for targeted integration of the expression cassettes into one of seven possible sites in the Aspergillus nidulans genome. The plasmids features a fungal selection marker gene (Aspergillus fumigatus AfpyrG), a USER cloning site (AsiSI and Nb.btsI) and is flanked by two 1-1.5 kb Aspergillus nidulans DNA sequences (named Up and Down) to allow for integration into the Aspergillus nidulans genome by targeted homologous recombination (Hansen, B. G., Salomonsen, B., Nielsen, M. T., Nielsen, J. B., Hansen, N. B., Nielsen, K. F., . . . Mortensen, U. H. (2011)). Versatile enzyme expression and characterization system for Aspergillus nidulans, with the Penicillium brevicompactum polyketide synthase gene from the mycophenolic acid gene cluster as a test case. Applied and Environmental Microbiology, 77(9), 3044-3051). The PCR amplicons were amplified using PfuX7 DNA polymerase and the resulting DNA fragments were gel purified. The recipient vectors were prepared for USER™ cloning by digesting it with AsiSI and Nb.btsI overnight, followed by gel purification. The PCR amplicons were directionally cloned into the recipient vector by USER™ cloning, combined with transformation into E. coli. DH5a cells were thawed on ice, and the USER™ mix was added to 50 µL of cells (1×10$^8$ cfu/µg pUC19). The mixture is placed on ice for 10 minutes, and heat shocked for 90 seconds at 45° C. Transferred to ice again and incubated for 5 minutes. The cells are plated on a LB-plate with selective antibiotic and incubated at 37° C. over night. The colonies are verified by PCR and the true transformants are grown in liquid LB-media with selective antibiotic over night for plasmid purification (Taylor, R. G., Walker, D. C., & McInnes, R. R. (1993). E. coli host strains significantly affect the quality of small scale plasmid DNA preparations used for sequencing. Nucleic Acids Research, 21(7), 1677-8).

```
An_HpPKS2-ScOpt-F
5'-AGAGCGAdUATGGGTTCCTTAGACAACGGTTC;
SEQ ID NO: 102

An_HpPKS2-ScOpt-R
5'-TCTGCGAdUTCACAAAGGAACACTTCTCAAAACC;
SEQ ID NO: 103

An_AaOKS-ScOpt-F
5'-AGAGCGAdUATGAGTTCACTCTCCAACGCTTCC;
SEQ ID NO: 104

An_AaOKS-ScOpt-R
5'-TCTGCGAdUTCACATGAGAGGCAGGCTGTG;
SEQ ID NO: 105

An_HpPKS2-Orig-F
5'-AGAGCGAdUGGGTTCCCTTGACAATGGTT;
SEQ ID NO: 106

An_HpPKS2-Orig-R
5'-TCTGCGAdUTTAGAGAGGCACACTTCGGAGAAC;
SEQ ID NO: 107

An_AaOKS-Orig-F
5'-AGAGCGAdUATGAGTAGTTTATCAAATGCCAGTC;
SEQ ID NO: 108

An_AaOKS-Orig-R
5'-TCTGCGAdUTCACATCAATGGCAAGGAA;
SEQ ID NO: 109
```

The verified expression plasmids were digested with SwaI (with AfpyrG marker), to liberate the expression cassette flanked by the up and down targeting sequences. The cassette was introduced into *Aspergillus nidulans* protoplast as specified above.

The following expression plasmids and were constructed:

| | |
|---|---|
| pIS53(pyrG)::HpPKS2_ScOpt | HpPKS2_ScOpt in IS53 locus |
| pIS53(pyrG)::HpPKS2_Orig | HpPKS2_Orig in IS53 locus |
| pIS53(pyrG)::AaOKS_ScOpt | AaOKS_ScOpt in IS53 locus |
| pIS53(pyrG)::AaOKS_Orig | AaOKS_Orig in IS53 locus |

The expression cassettes of the individual plasmids were liberated by SwaI digestion (with AfpyrG marker) and subsequently transformed into *Aspergillus nidulans* protoplasts. Following construction of the individual strain the used AfpyrG markers were eliminated by 5-FOA counter selection.

Chemical Analysis of the Constructed *Aspergillus nidulans* Strains

To access the effects the introduced genes had on the metabolism of the constructed *Aspergillus nidulans* strains, the strain were grown on MM, with appropriate supplements, for 5 to 14 days at 37° C. Metabolites were extracted by micro-scale extraction procedure described by Smedsgaard (Smedsgaard, J. (1997). Micro-scale extraction procedure for standardized screening of fungal metabolite production in cultures. Journal of Chromatography A, 760(2), 264-270). Summarized: Ten 0.4-0.6 mm circular plugs were cut from the culturing plates using a 'cork borer' and placed in a 8 ml glass vial containing 2 ml of extraction solution made of methanol and 1% (v/v) formic acid. The tubes were ultrasonicated for 60 minutes in a water bath. The supernatant was transferred to a new vial and evaporated under a stream of nitrogen gas and heat (30° C.), and the resulting pellet was dissolved in 100 µl of HPLC grade methanol and 1% formic acid (Sigma-Aldrich) by incubating the solution for 20 minutes in an ultrasonic bath. The resulting extraction solution was then filtered through a PTFE 0.45 um, 15 mm Premium Syringe Filters (Agilent Technologies) into HPLC vials. The extracted metabolites were analyzed using Agilent 1200 HPLC coupled to a Bruker micrOTOF-Q II mass spectrometer equipped with an electrospray ionization source. Chromatographic separation was obtained on a Luna Cis (2) column (150 35×4.6 mm, 3 µm, 100 Å, Phenomenex) maintained at 40° C. The aqueous eluent (A) consisted of water/acetonitrile (95:5, v/v) and the organic eluent (B) consisted of water/acetonitrile (5:95, v/v); both acidified with 0.1% formic acid According to the purpose of the analysis, two different linear gradient elution profiles has been used: Method 1: 0 min, 0% B; 20 min, 100% B; 22 min 100% B; 24 min, 0% B. The flowrate was maintained at 0.8 mL/min and 7 min equilibration was used.

Method 2:

0 min, 0% B; 30 min, 100% B; 33 min 100% B; 35 min, 0% B. The flowrate was maintained at 0.5 mL/min and 10 min equilibration was used.

The samples were analyzed both in positive and negative ionization mode. The resulting dataset was analyzed using the following Software MassHunter (Agilent technologies). The resulting Base Peak Chromatograms (BPC) was inspected to identify changes in the metabolism of the fungus. While Extracted Ion Chromatograms (EIC) for masses fitting the expected intermediates in the biosynthetic pathway was generated to ease identification of the relevant peaks.

Alternatively, the production of metabolites was analyzed in liquid MM cultures. For this 500 mL sterile Erlenmeyer flasks with 100 ml of liquid minimal medium, with appropriate supplements, were inoculated with a solution of macroconidia from the strains to be analyzed. The flasks were incubated for 1-15 days at 37° C. in a shake incubator with 150 rpm. The mycelium was poured through Miracloth (Merck Millipore) and separated from culture media. The mycelium was fast frozen with liquid nitrogen. The media was sterile filtered through an FPE-214-250 JET BIOFIL®. The sterile media was then transferred to a 40 mL vial for chemical analysis.

Extraction

Fermentation broth (40 mL) was evaporated to dryness in vacuo and extracted with ethanol+10% formic (20 mL) acid by means of sonication (2 h) at 60° C. The solvent was decanted and dried in vacuo before being dissolved in 1.5 mL ethanol+10% formic acid using sonication. The supernatant was dried in a speedvac and dissolved in 180 µL 90% methanol+10% formic acid, centrifuged and analyzed by HPLC-MS/MS Results:

Analysis of the formed metabolites by UHPLC-HRMS of the strains comprising heterologous HpPKS2 or AaOKS showed that expression of the type III PKSs (HpPKS2 orAaOKS) resulted in the production of different compounds including the compounds SEK4, SEK4B and FK. Expression in the SMA cluster deletion strain resulted in a higher ratio of FK and SEK4/SEK4B.

CONCLUSION

Expression of plant type III PKS (HpPKS2 or AaOKS) resulted in the production of different compounds including the compounds SEK4, SEK4B, FK anthrone, Mutactin and FK in vivo in *Aspergillus nidulans*. Expression in the strain with deleted asperthecin, sterigmatocystin and monodictyphenone/emodin gene clusters had a positive impact on production of the metabolites.

Since there in this Example 6 were not inserted heterologous cyclases and/or aromatases into the *Aspergillus* strains and FK compound was identified—it indicates that *Aspergillus* strains may comprise homologous cyclases and/or aromatases capable of converting in vivo non-reduced octaketide into FK compound.

Example 7: Stable Expression of Type III PKSs and Cyclases and/or Aromatases in *Aspergillus nidulans*

Materials and Methods

Expression of Bacterial Cyclases and Aromatases in *Aspergillus nidulans*

Synthetic codon optimized version of ZhuI, ZhuJ for *Aspergillus*, *S. cerevisiae* and *E. coli* expression were purchased from Genscript. Similarly as described for the type III PKSs the cyclases and aromatases encoding genes were cloned into expression vectors targeting specific sites in the *Aspergillus* genome, different from the site used for expression of the Type III PKS (see Example 6). Said in other words, the ZhuI and ZhuJ genes were cloned into the *Aspergillus* strains of Example 5 that already comprised the heterologous type III PKS genes (HpPKS2, AaOKS).

Primers used for the construction process, where dU represents 2-deoxyuridin:

An_ZhuI_EcOpt-F
5'-AGATATACCAdUGCGTCATGTTGAACATACCGT
SEQ ID NO: 110

An_ZhuI_EcOpt-R
5'-ATGGCTGCdUTTATGCGGTAACTGTACCAACACCA
SEQ ID NO: 111

An_ZhuJ_EcOpt-F
5'-ATATACATAdUGAGCGGTCGTAAAACCTTT
SEQ ID NO: 112

An_ZhuJ_EcOpt-R
5'-ATATCCAATdUTTAATCCTCTTCTTCTTGTTC
SEQ ID NO: 113

An_ZhuI_ScOpt-F
5'-AGAGCGAdUGAGACACGTTGAACACA
SEQ ID NO: 114

An_ZhuI_ScOpt-R
5'-TCTGCGAdUTTATGCAGTTACGGTACCA
SEQ ID NO: 115

An_ZhuJ_ScOpt-F
5'-AGAGCGAUGTCCGGTAGAAAGACCTT
SEQ ID NO: 116

An_ZhuJ_ScOpt-R
5'-TCTGCGAUTTAATCTTCTTCTTCTTGTTCG
SEQ ID NO: 117

The PCR amplified coding sequences were cloned into vectors for targeted integration in the *Aspergillus nidulans* genome: ZhuI in IS80 and ZhuJ in IS82. The verified expression cassettes were transformed into *Aspergillus nidulans*, by sequential targeted integration of the individual expression cassette, as described in Example 6. The AfpyrG marker was eliminated following each transformation round to allow for a subsequent transformation round introducing an additional expression cassette.

Chemical analysis was performed as described in Example 6.

Results:

Analysis of the formed metabolites by UHPLC-HRMS showed that expression of ZhuI and ZhuJ did not significantly affect amount of produced metabolites (including the compounds SEK4, SEK4B and FK), i.e. the amounts produced by the strains of this Example 7 (comprising PKS (HpPKS2 or AaOKS)+ZhuI and ZhuJ) were similar to the amounts produced by the strains of Example 6 (comprising only PKS (HpPKS2 or AaOKS)).

CONCLUSION

The results showed that expression of ZhuI and ZhuJ optimized for expression in *E. coli* did not significantly affect the produced metabolites in *Aspergillus nidulans*.

Example 8: Heterologous Expression of Type III PKSs and *Dactylopius Coccus* C-Glycosyltransferase in *Aspergillus nidulans*

Materials and Methods

Construction of plasmids, genetic transformation of *Aspergillus nidulans* and chemical analysis was performed as described in Example 6.

Construction of Vectors for Expression of the *Dactylopius Coccus* C-Glycosyltransferase in *Aspergillus nidulans*

The DcUGT2 gene was cloned/inserted into PKS (AaOKS) *Aspergillus nidulans* strain of Example 6.

The full length DcUGT2 gene from *Dactylopius coccus* was codon optimized for expression in *Aspergillus nidulans* and purchased from GenScript as synthetic DNA. For PCR based amplification of the DcUGT2 coding sequence the following primers were used: DcUGT2_AnOpt-F: 5'-AGAGCGAdUATGGAGTTTCGCTTGCTTATCCT (SEQ ID NO:118) and DcUGT2_AnOpt-R: 5'-TCTGC-GAdUTTAATTCTTCTTCAACTTTTCCGACTTAG (SEQ ID NO:119). The resulting PCR amplicon was cloned into an *Aspergillus nidulans* expression vector as described in Example 6. The used expression vector targeted the IS52 site in the genome of *Aspergillus nidulans*.

Results:

Analysis of the formed metabolites the *Aspergillus nidulans* strains comprising heterologous AaOKS and DcUGT2 showed that expression of resulted in the production of different compounds including the compounds CA, DCII, KA. The compounds FK, SEK4 and SEK4b were also identified, and co-expression of the DcUGT2 gave a higher yield of the before mentioned compounds.

CONCLUSIONS

Co-expression of the heterologous PKS (AaOKS) and glycosyltransferase (DcUGT2) in *Aspergillus nidulans* resulted in production of CA, DCII, KA. The compounds FK, SEK4 and SEK4b were also identified, and co-expression of the DcUGT2 gave a higher yield of the before mentioned compounds.

Example 9: Expression of AaOKS in N, Benthamiana and In Vitro Activity Test

Expression of AaOKS in N, Benthamiana

AaOKS (Gene bank accession AY567707) (Abe I, Oguro S, Utsumi Y, Sano Y, Noguchi H (2005b). Engineered biosynthesis of plant polyketides: chain length control in an octaketide-producing plant type III polyketide synthase. J Am Chem Soc 127: 12709-12716.; Abe I, Utsumi Y, Oguro S, Morita H, Sano Y, Noguchi H (2005a). A plant type III polyketide synthase that produces pentaketide chromone. J Am Chem Soc 127:1362-1363) was synthesized by Genescript and amplified with primers containing a C-terminal his-tag and USER overhang for cloning into the USER-compatible pEAQ vector (Sainsbury F, Thuenemann E C, Lomonossoff G P (2009) pEAQ: versatile expression vectors for easy and quick transient expression of heterologous proteins in plants. Plant Biotechnol J 7: 682-693) with the USER-method (Nour-Eldin H H, Hansen B G, Nørholm MH, Jensen J K, Halkier B A (2006). Advancing uracil-excision based cloning towards an ideal technique for cloning PCR fragments. Nucleic Acids Res 34: e122.) to give the resulting plasmid pEAQ-AaOKS. The plasmid was propagated in *E. coli* TOP10 cells and verified by sequencing. The plasmid was transformed into *Agrobacterium tumefaciens* by electroporation and positive clones were selected on Luria-Bertani (LB) agar supplemented with rifampicin (12.5 µg/mL.), kanamycin (50 µg/mL), and ampicillin (25 µg/mL) followed by PCR to verify the presence of AaOKS. For expression, *A. tumefaciens* harboring pEAQ-AaOKS or pEAQ was cultured overnight in liquid LB supplemented with rifampicin (12.5 µg/mL.), kanamycin (50 µg/mL) and ampicillin (25 µg/mL). The cells were pelleted by centrifugation and resuspended in infiltration medium (10 mM MES, 100 µM acetosyringone, 10 mM $MgCl_2$) to a final $OD_{600}$: 0.5 and incubated at room temperature for 1 hr. *A. tumefaciens* was infiltrated into the leaves of 3-4 weeks old N. benthamiana plants by a needle-less syringe and the plants grew for a further 5 days in the green house.

Extraction of Soluble Protein from N, Benthamiana 300 mg of plant material was grinded in a cold mortar with pestle and the addition of 0.5 g PVPP and 10 mL cold extraction buffer (50 mM sodium phosphate, 400 mM sucrose, 4 mM DTT, pH 7.2 containing Complete proteinase inhibitor (Roche)). The homogenate was filtered through nylon mesh into cold centrifuge tubes and centrifuged at 10.000×g at 4° C. for 15 min. The supernatant was isolated and centrifuged at 100.000×g at 4° C. for 60 min. The soluble fraction (supernatant) was isolated. Production of his-tagged AaOKS was verified by western blotting using anti-his antibody. His-tagged AaOKS was purified from the soluble fraction using His Spin Trap columns (GE health care biosciences) according to the manufacturer's instructions.

Polyketide Synthase Assay

Crude soluble enzyme extract of N. benthamiana leaves and affinity purified his-AaOKS were tested for polyketide synthase activity. The standard assay contain 100 µl soluble protein or 20 µl affinity purified his-AaOKS in a total reaction volume of 250 µl containing 50 mM sodium phosphate, 500 mM sucrose, 1 mM DTT, 40 µM malonyl-CoA, 20 µM acetyl-coA, pH 7. The standard assay was supplemented with [2-$^{14}$C]malonyl-CoA (1.8 mCi/mmol) for TLC analysis or [$^{13}C_3$]-malonyl-CoA for structural analysis. The reactions were incubated at 30° C. for 90 min, terminated by the addition of 25 µl 20% HCl and extracted twice with 500 µl ethyl acetate, 1% (w/v) acetic acid. The organic phase was dried in vacuo and resuspended in 20 µl methanol, 1% (w/v) acetic acid and analyzed by TLC or LC-MS.

Results—In Vitro Enzyme Activity of AaOKS:

Crude enzyme extract from N. benthamiana expressing AaOKS were tested for octaketide synthase activity using malonyl-CoA as starter substrate. When $^{14}$C-malonyl-CoA was incubated with crude enzyme extract or affinity-purified AaOKS the substrate was metabolized, as observed by the appearance of radioactive band on thin layer chromatogram, whereas no products were observed when using crude enzyme extract from tobacco plants infiltrated with plasmid alone. For structural elucidation $^{13}$C-malonyl-coA was used as the substrate and the labelled products were identified by LC-MS as SEK4 and SEK4B. There was no difference in product formation when AaOKS was tagged with a C-terminal his-tag and this shows that the HIS-tag did not interfere with enzymatic activity. The results showed that AaOKS heterologously expressed in N. benthamiana has octaketide synthase activity and that the affinity purified enzyme in vitro produces the octaketide-derived shunt products SEK4 and SEK4B.

CONCLUSION

The results showed that AaOKS heterologously expressed in N. benthamiana has octaketide synthase activity and that the affinity purified enzyme in vitro produces the octaketide-derived shunt products SEK4 and SEK4B.

Example 10: Cloning Truncated Versions of DcUGT2 in S. cerevisiae and Test of their In Vitro Activity Towards F K and KA Materials and Methods
Expression Truncated DcUGT2 Gene Constructs in S. cerevisiae Truncated forms of DcUGT2 were generated lacking both the signal sequence and membrane anchor (ΔSP_DcUGT2ΔMD-Strep) or the membrane anchor (DcUGT2ΔMD-Strep) alone. The fragments encoding ΔSP_DcUGT2ΔMD-Strep and DcUGT2ΔMD-Strep were amplified separately from the pYES-DEST52-DcUGT2-Strep plasmid using specific PCR primers to incorporate a C-terminal StrepII-tag (see table below). Gateway recombination sites, attB1 and attB2, were introduced into the generated fragments in a following PCR using forward primer: 5'-ggggacaagtttgtacaaaaaagcaggct-3' (SEQ ID NO:88) and reverse primer: 5'-ggggaccactttgta-caagaaagctgggt-3' (SEQ ID NO:128). ΔSP_DcUGT2ΔMD-Strep and DcUGT2ΔMD-Strep flanked with attB sites were cloned into pDONR207 plasmid (Invitrogen) and transferred into destination plasmid, pYES-DEST52 (Invitrogen) by using the Gateway technology system. The two pYES-DEST52 plasmid constructs were transformed separately into the Invscl yeast strain (Invitrogen) and positive transformants were verified by PCR. Heterologous protein production was performed according to the instructions of the pYES-DEST52 gateway plasmid (Invitrogen). Production of heterologous StrepII-tagged protein was verified by western blotting using anti-Strep antibody. A membrane bound and a soluble protein fraction were prepared from verified yeast transformants as described in (Pompon, D., Louerat, B., Bronine, A., Urban, P. (1996). Yeast expression of animal and plant P450s in optimized redox environments. Methods Enzymol. 272:51-64) and screened for glucosylation activity towards flavokermesic acid/kermesic acid as described above.

Example 11: In Planta Production of Carminic Acid and DcII by Heterologous Expression of Genes Encoding PKS, Cyclase and Full Length DcUGT Enzymes in Nicotiana benthamiana Transient Expression of Gene Constructs in Nicotiana benthamiana Synthetic DNA fragments encoding ZhuI (Genbank accession: AAG30197) and ZhuJ (Genbank accession: AAG30196) codon optimized for N. benthamiana expression and AaOKS (Genbank accession: AY567707) were purchased from Genscript. All synthetic fragments and the herein described pYES-DEST52-DcUGT2-Strep plasmid were used as PCR templates with compatible deoxyuracil (dU)-containing primers (see Table 5 below) to generate constructs that were cloned into pEAQ-HT-USER by USER technology. The truncated DcUGT2 version, DcUGT2ΔMD-Strep, was transferred from the pDONR207 plasmid (Invitrogen) into destination plasmid, pEAQ-HT-DEST1 (Sainsbury, F., Saxena, P., Geisler, K., Osbourn, A., Lomonossoff, G. P. (2012). Using a Virus-Derived System to Manipulate Plant Natural Product Biosynthetic Pathways. Methods Enzymol. 517:185-202), using the Gateway technology system. All pEAQ-HT plasmid constructs were transformed into the Agrobacterium tumefaciens strain, AGL-1 and infiltrated into leafs of N. benthamiana plants as described in (Bach, S. S., Bassard, J. E., Andersen-Ranberg, J., Møldrup, M. E., Simonsen, H. T., Hamberger, B. (2014). High-Throughput Testing of Terpenoid Biosynthesis Candidate Genes Using Transient Expression in Nicotiana benthamiana. In M Rodriguez Concepcion, ed, Plant Isoprenoids, Methods in Molecular Biology, Vol. 1153. Humana Press, New York).

TABLE 5

Primer sequences for amplification of different gene constructs

| Gene fragments | | Primer sequence |
|---|---|---|
| AaOKS | Forward | 5'-GGCTTAA/dU/ATGAGTTCACTCTCCAACGCTTCCCATC-3' (SEQ ID NO: 120) |
| | Reverse | 5'-GGTTTAA/dU/TTACATGAGAGGCAGGCTGTGGAGAAGGATAGT-3' (SEQ ID NO: 121) |
| ZhuI | Forward | 5'-GGCTTAA/dU/ATGAGGCATGTCGAGCAT-3' (SEQ ID NO: 122) |
| | Reverse | 5'-GGTTTAA/dU/TTATGCCGTGACAGTTCCGACAC-3' (SEQ ID NO: 123) |
| ZhuJ | Forward | 5'-GGCTTAA/dU/ATGTCCGGACGTAAGACG-3' (SEQ ID NO: 124) |
| | Reverse | 5'-GGTTTAA/dU/TTAATCTTCCTCCTCCTGTTCAA-3' (SEQ ID NO: 125) |
| DcUGT2-Strep | Forward | 5'-GGCTTAA/dU/ATGGAATTCAGATTGTTGATATTGGCCT-3' (SEQ ID NO: 126) |
| | Reverse | 5'-GGTTTAA/dU/TTATTTTTCGAATTGTGGATGAGACCAAGCAGA-3' (SEQ ID NO: 127) |
| DcUGT2 ΔMD-Strep | Forward (attB1) | 5'-ggggacaagtttgtacaaaaaagcaggct-3' (SEQ ID NO: 88) |
| | Reverse | 5'-TTATTTTTCGAATTGTGGATGAGACCAAGCAGAGTGCAAAAAGGCACCTGCAGT-3' (SEQ ID NO: 89) |

Metabolite Extraction and LC-MS/MS Analysis

Metabolites were extracted from discs (0=3 cm) of agroinfiltrated *N. benthamiana* leaves. Leaf discs, excised with a cork borer, were flash frozen in liquid nitrogen. 0.5 ml of extraction buffer (85% (v/v) methanol, 0.1% (v/v) formic acid), equilibrated to 50° C., were added to each frozen leaf disc followed by incubation for 1 hour at 50° C., agitating at 600 rpm. The supernatant was isolated and passed through a MultiscreenHTs HV 0.45 µm filter plate (Merck Milipore). The filtered supernatant was subjected to LC-MS/MS analysis which was performed on an Agilent 1200 HPLC coupled to a Bruker micrOTOF-Q II mass spectrometer equipped with an electrospray ionization source. Chromatographic separation was obtained on a Luna Cis(2) column (150×4.6 mm, 3 µm, 100 Å, Phenomenex) maintained at 40° C. The aqueous eluent (A) consisted of water/acetonitrile (95:5, v/v) and the organic eluent (B) consisted of water/acetonitrile (5:95, v/v); both acidified with 0.1% formic acid. According to the purpose of the analysis, two different linear gradient elution profiles were used:

Method 1: 0 min, 0% B; 30 min, 100% B; 33 min 100% B; 35 min, 0% B. The flow rate was maintained at 0.5 mL/min and 10 min equilibration was used. Retention times were 15.5 min for dcII, 15.6 min for carminic acid (CA), 17.1 min for flavokermesic-O-Glc 2 (FK-O-Glc 2), 17.2 min for SEK4, 17.7 min for SEK4B, 22.7 min for flavokermesic acid (FK) and 22.7 min for kermesic acid (KA).

Method 2: 0 min, 10% B; 25 min, 20% B; 27 min 100% B; 35 min, 100% B; 36 min, 10% B. The flow rate was maintained at 0.5 mL/min and 10 min equilibration was used. Retention times were 16.1 min for flavokermesic-O-Glc 1 (FK-O-Glc 1), 17.0 min for dcII, 18.2 min for carminic acid (CA), 24.1 min for SEK4, 25.5 min for flavokermesic-O-Glc 2 (FK-O-Glc 2), 26.8 min for SEK4B, 35.5 min for flavokermesic acid (FK) and 36.0 min for kermesic acid (KA).

O-glucosides were identified with viscozyme L-treatment and by the neutral loss of 162 Da in the MS/MS spectrum.

Results:

The AaOKS of *Aloe arborescens* has previously been characterized to be an octaketide synthase belonging to the type III PKS enzyme class. To investigate the possibility of using such a type III PKS enzyme to generate the octaketide precursor required for carminic acid production, the AaOKS gene was transiently expressed in *N. benthamiana*. The AaOKS gene, when compared to empty plasmid control, results in formation of SEK4 and SEK4B after agroinfiltration in to leaves of *N. benthamiana*. This demonstrates that AaOKS can function as an active octaketide synthase in vivo in *N. benthamiana*. Furthermore since no flavokermesic acid (FK) anthrone or FK could be observed when AaOKS is agroinfiltrated alone, *N. benthamiana* may lack endogenous enzymes to further metabolize SEK4 and SEK4B into these compounds. Thus the cyclase genes, ZhuI and ZhuJ, were co-agroinfiltrated with AaOKS. ZhuI and ZhuJ originate from the R1128 antibiotic biosynthetic pathway and have previously been combined in vivo with the actinorhodin minimal PKS in *Streptomyces coelicolor* to produce FK (Tang, Y., Lee, T. S., Khosla, C. (2004). Engineered biosynthesis of regioselectively modified aromatic polyketides using bimodular polyketide synthases. PLOS Biol. 2(2): E31). In *N. benthamiana*, when ZhuJ is co-agroinfiltrated with AaOKS, accumulation of FK and flavokermesic acid-O-glucoside, FK-O-Glc 2 is observed and this is not the case when AaOKS is co-agroinfiltrated with ZhuI. The production of FK-O-Glc 2 suggests that one or several endogenous *N. benthamiana* UGT(s) are capable of efficiently using FK as substrate. Additionally, the co-agroinfiltration of ZhuI with AaOKS reduces the production of SEK4B by promoting the formation of SEK4 which is in accordance with the previous finding that ZhuI directs the initial C7-C12 cyclization (rather than the C10-C15 cyclization which results in SEK4B formation) of the linear octaketide (Ames, B. D., Lee, M. Y., Moody, C., Zhang, W., Tang, Y., Tsai, S. C. (2011). Structural and biochemical characterization of ZhuI aromatase/cyclase from the R1128 polyketide pathway. Biochemistry. 39: 8392-8406). This initial $C_7$-$C_{12}$ cyclization is also required for the biosynthesis of the anthraquinone backbone of FK/CA and when ZhuI is co-agroinfiltrated with AaOKS and ZhuJ, the total pool of FK and flavokermesic acid-O-glucoside is indeed markedly increased as compared to when it is absent.

In planta production of DCII and CA was detected when full length DcUGT2_Strep was co-expressed with AaOKS, ZhuI and ZhuJ in N. benthamiana. The production of CA is only found in trace amounts when compared to levels of DCII. This CA production is likely due to an unspecific endogenous monooxygenase activity in N. benthamiana that either is capable of hydroxylating FK to kermesic acid (KA) or DCII to CA. However, it is noteworthy that KA is not detectable in any of the agroinfiltration studies, indicating that this compound is either produced at levels below our detection limit or it may be highly toxic for N. benthamiana and therefore rapidly metabolized into unknown products.

CONCLUSIONS

The results of this Example demonstrated:

(i): The AaOKS gene from *Aloe arborescens* was transiently expressed in N. benthamiana and in vivo this resulted in formation of SEK4 and SEK4B, which demonstrated that AaOKS can function as an active octaketide synthase in vivo in N. benthamiana;

(ii): Since no flavokermesic acid (FK) anthrone or FK could be observed when AaOKS was agroinfiltrated alone, N. benthamiana may lack endogenous enzymes to further metabolize SEK4 and SEK4B into these compounds.

(iii): The cyclase genes ZhuI and ZhuJ, from *Streptomyces* sp. R1128, were co-agroinfiltrated with AaOKS and when ZhuJ was co-agroinfiltrated with AaOKS, accumulation of FK and flavokermesic acid-O-glucoside, FK-O-Glc 2 was observed. When ZhuI was co-agroinfiltrated with AaOKS and ZhuJ, the total pool of FK and flavokermesic acid-O-glucoside was indeed markedly increased as compared to when it is absent. Accordingly, heterologous expression of *Streptomyces* sp cyclase genes resulted in in vivo the production of different compounds including FK;

(iv): In vivo production of DCII and CA was detected when full-length DcUGT2 Strep was co-expressed with AaOKS, ZhuI and ZhuJ in N. benthamiana.

Example 12: Heterologous Expression of a Truncated Version of DcUGT2 and Test of its in Planta Activity in N. Benthamiana To investigate whether the DcUGT2 protein, could be solubilized and still retain glucosylation activity towards KA and FK, the membrane anchor was deleted. DcUGT2 is predicted via bioinformatics to be located to the ER with the C-terminal anchored in the ER membrane and the N-terminal active site facing the lumen. Therefore it was speculated whether the protein might be N-glycosylated and, if so this posttranslational modification might be required for the activity of the DcUGT2 enzyme. An N-glycosylation bioinformatics prediction analysis was carried out, identifying 3 putative N-glycosylation sites. To investigate whether glycosylation and the ER targeting play a role for the activity of the DcUGT2 enzyme, a truncated DcUGT2 form was generated where the signal peptide was intact but the membrane anchor deleted (DcUGT2ΔMD-Strep). This DcUGT2ΔMD-Strep protein is active in vivo and produced DCII when co-expressed with AaOKS and ZhuJ in N. benthamiana. The production of DCII was lower in these plants compared to the DCII levels in plants co-agroinfiltrated with the DcUGT2. This could imply that although the DcUGT2ΔMD-Strep protein is active, the level of the enzyme activity may be compromised by the deletion of the membrane anchor. The fact that DcUGT2ΔMD-Strep still possesses some glucosylation activity towards FK and/or KA indicates further that N-glycosylation and (or) ER-targeting of the protein might be crucial for the activity of the enzyme. Additionally it should be pointed out that the full-length DcUGT2 appears to compete efficiently with the N. benthamiana FK O-glucosylation activity, thereby significantly reducing the pool of flavokermesic acid-O-Glc (FK-O-Glc 1 and 2) and this is not observed for the truncated DcUGT2ΔMD-Strep version.

CONCLUSIONS

The results of this Example demonstrated that DcUGT2ΔMD-Strep (lacking the membrane anchor—amino acids 1 to 468 of SEQ ID NO:2) was active in vivo in N. benthamiana plant. The activity of DcUGT2ΔMD-Strep (lacking the membrane anchor) was less than full-length DcUGT2 enzyme—however, the fact that it was active may indicate that it could be particular useful for heterologous production in e.g. prokaryotic organisms.

REFERENCES

1: U.S. Pat. No. 5,424,421 (European Colour, published 1995)
2: WO2006/056585A1 (Chr. Hansen A/S)
3: Stathopoulou et al (Analytica Chimica Acta 804 (2013) 264-272)
4: Zagrobelny et al (Cyanogenic glucosides and plant-insect interactions; Phytochemistry. 2004 February; 65(3):293-306)
5: Geuder et al (Journal of Chemical Ecology, Vol. 23, No. 5, 1997)
6: Genta et al, (Potential role for gut microbiota in cell wall digestion and glucoside detoxification in *Tenebrio molitor* larvae), Journal of Insect Physiology 52 (2006) 593-601
7: WO2004/111254A1 (Poalis A/S)
8: Gutmann et al (Pure Appl. Chem, 2013 Jul. 9)
9: Baig et al (Angew Chem Int Ed Engl. 2006 Nov. 27; 45(46):7842-6)
10: Radominska-Pandya A, Bratton S M, Redinbo M R, Miley M J. Drug Metab Rev. 2010 February; 42(1):133-44)
11: Plant Physiology, November 2008, Vol. 148, pp. 1295-1308
12: Esben Halkjaer Hansen et al. Phytochemistry 70(4): 473-482
13: Tang, Y., Lee, T. S., and Khosla, C. (2004) Engineered biosynthesis of regioselectively modified aromatic polyketides using bimodular polyketide synthases. PLoS Biol. 2, e31
14. Mizuuchi Y, Shi S P, Wanibuchi K, Kojima A, Morita H, Noguchi H, Abe I. Novel type III polyketide synthases from *Aloe arborescens*. FEBS J. 2009 April; 276(8):2391-2401.
15. Karppinen K, Hokkanen J, Mattila S, Neubauer P, Hohtola A. Octaketide-producing type III polyketide synthase from *Hypericum perforatum* is expressed in dark glands accumulating hypericins. FEBS J. 2008 September; 275(17):4329-4342.
16. Dayu Yu, Fuchao Xu, Jia Zeng, Jixun Zhan. Type III Polyketide Synthases in Natural Product Biosynthesis. IUBMB Life, 64(4): 285-295, April 2012
17. Supriya Jadhav, Prasad Phapale, Hirekodathakallu V. Thulasiram, Sujata Bhargava. Polyketide synthesis in tobacco plants transformed with a *Plumbago zeylanica* type III hexaketide synthase. Phytochemistry 98 (2014) 92-100.

The invention claimed is:

1. A method for producing an octaketide derived aromatic compound, wherein the method comprises:
   (I): contacting in vivo in a recombinant host cell comprising a recombinantly introduced Type III polyketide synthase (PKS) gene encoding an octaketide synthase (OKS), wherein the OKS is of a different genus than the host cell:
      (i): a starter unit and an extender unit with said OKS such that the starter and extender units convert into a non-reduced octaketide;
   (II): converting in vivo within the recombinant host cell the non-reduced octaketide of step (I) into a $C_{14}$-$C_{34}$ aromatic aglycon compound via at least one in trans acting aromatase/cyclase, wherein the aromatic aglycon compound is not SEK4 and/or SEK4B;
   (III): the recombinant host cell further comprises a glycosyltransferase gene encoding a glycosyltransferase having at least 90% sequence identity to SEQ ID NO: 2 or amino acids 1 to 468 of SEQ ID NO:2, which glycosylates the aromatic aglycon compound produced in step (II) into a $C_{14}$-$C_{34}$ aromatic glycoside compound; and
   (IV): isolating the aromatic glycoside compound of step (III) so as to get a composition, wherein the composition comprises less than 1% w/w dry matter of recombinant host cell material, and wherein the recombinant host cell is a plant cell or a filamentous fungal cell.

2. The method of claim 1, wherein the recombinant host cell is a growing recombinant host cell and step (I) and step (II) comprise:
   (I): contacting in vivo in a growing recombinant host cell comprising a recombinantly introduced Type III polyketide synthase (PKS) gene encoding an octaketide synthase (OKS), wherein the OKS is of a different genus than the host cell:
      (i): a starter unit and an extender unit with said OKS such that the starter and extender units convert into a non-reduced octaketide; and
   (II): converting in vivo within the growing recombinant host cell the non-reduced octaketide of step (I) into a $C_{14}$-$C_{34}$ aromatic aglycon compound, wherein the aromatic aglycon compound is not SEK4 and/or SEK4B.

3. The method according to claim 1, wherein the plant cell is *Nicotiana* sp.

4. The method according to claim 1, wherein the plant cell is an *Aspergillus* cell.

5. The method according to claim 1, wherein the Type III polyketide synthase (PKS) gene of step (I) is a PKS gene from a plant and wherein the plant is a plant selected from the group consisting of: *Aloe* spp. and *Hypericum* spp.

6. The method of claim 5, wherein the octaketide synthase (OKS) in step (I) is a OKS comprising an amino acid sequence, which has at least 70% sequence identity with amino acids 1 to 403 of SEQ ID NO:7 (AaOKS).

7. The method of claim 5, wherein the octaketide synthase (OKS) in step (I) is a OKS comprising an amino acid sequence, which has at least 70% identity with amino acids 1 to 393 of SEQ ID NO:15 (HpPKS2).

8. The method according to claim 1, wherein the starter unit is acetyl-CoA and/or malonyl-CoA.

9. The method according to claim 1, wherein the:
   recombinant host cell is a host cell selected from the group consisting of: *Aspergillus* and *Nicotiana* sp.; and
   the OKS of a different genus than the host cell is an OKS selected from the group consisting of: OKS from *Aloe* spp.) and *Hypericum* spp.

10. The method according to claim 1, wherein the aromatic aglycon compound is a $C_{16}$ aromatic aglycon compound.

11. The method according to claim 10, wherein the $C_{16}$ aromatic aglycon compound is flavokermesic acid (FK) or kermesic acid (KA).

12. The method of claim 1, wherein the aromatase/cyclase is a aromatase/cyclase comprising an amino acid sequence, which has at least 70% sequence identity with amino acids 1 to 169 of SEQ ID NO:17 (*Streptomyces* ZhuI); and/or wherein the aromatase/cyclase is a aromatase/cyclase comprising an amino acid sequence, which has at least 70% sequence identity with amino acids 1 to 256 of SEQ ID NO:19 (*Streptomyces* ZhuJ).

13. The method of claim 1, wherein the aromatic glycoside compound of interest is a $C_{16}$ aromatic glycoside compound and wherein the $C_{16}$ aromatic glycoside compound is a flavokermesic acid glycoside or a kermesic acid glycoside.

14. The method of claim 13, wherein the $C_{16}$ aromatic glycoside compound is a flavokermesic acid glycoside and the flavokermesic acid glycoside is DcII.

15. The method of claim 13, wherein the $C_{16}$ aromatic glycoside compound is a kermesic acid glycoside and the kermesic acid glycoside is carminic acid (CA).

* * * * *

SEQUENCE LISTING

<160> NUMBER OF SEQ ID NOS: 128

<210> SEQ ID NO 1
<211> LENGTH: 1548
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(1548)

<400> SEQUENCE: 1

```
atg gaa ttt cgt tta cta atc ctg gct ctt ttt tct gta ctt atg agt      48
Met Glu Phe Arg Leu Leu Ile Leu Ala Leu Phe Ser Val Leu Met Ser
 1               5                  10                  15 act tca aac gga gca gaa att tta gct ctt ttc cct att cac ggt atc      96
Thr Ser Asn Gly Ala Glu Ile Leu Ala Leu Phe Pro Ile His Gly Ile
             20                  25                  30 agt aat tat aat gtt gct gaa gca ctg ctg aag acc tta gct aac cgg     144
Ser Asn Tyr Asn Val Ala Glu Ala Leu Leu Lys Thr Leu Ala Asn Arg
         35                  40                  45 ggt cat aat gtt aca gtt gtc aca tct ttt cct caa aaa aaa cct gta     192
Gly His Asn Val Thr Val Val Thr Ser Phe Pro Gln Lys Lys Pro Val
     50                  55                  60 cct aat ttg tac gaa att gac gta tct gga gct aaa ggc ttg gct act     240
Pro Asn Leu Tyr Glu Ile Asp Val Ser Gly Ala Lys Gly Leu Ala Thr
 65                  70                  75                  80 aat tca ata cat ttt gaa aga tta caa acg att att caa gat gta aaa     288
Asn Ser Ile His Phe Glu Arg Leu Gln Thr Ile Ile Gln Asp Val Lys
                 85                  90                  95 tcg aac ttt aag aac atg gta cga ctt agc aga aca tac tgt gag att     336
Ser Asn Phe Lys Asn Met Val Arg Leu Ser Arg Thr Tyr Cys Glu Ile
            100                 105                 110 atg ttt tct gat ccg agg gtt ttg aac att cga gac aag aaa ttc gat     384
Met Phe Ser Asp Pro Arg Val Leu Asn Ile Arg Asp Lys Lys Phe Asp
        115                 120                 125 ctc gta ata aac gcc gta ttt ggc agt gac tgc gat gcc gga ttc gca     432
Leu Val Ile Asn Ala Val Phe Gly Ser Asp Cys Asp Ala Gly Phe Ala
    130                 135                 140 tgg aaa agt caa gct cca ttg att tca att ctc aat gct aga cat act     480
Trp Lys Ser Gln Ala Pro Leu Ile Ser Ile Leu Asn Ala Arg His Thr
145                 150                 155                 160 cct tgg gcc cta cac aga atg gga aat cca tca aat cca gcg tat atg     528
Pro Trp Ala Leu His Arg Met Gly Asn Pro Ser Asn Pro Ala Tyr Met
                165                 170                 175 cct gtc att cat tct aga ttt cct gta aaa atg aat ttc ttc caa aga     576
Pro Val Ile His Ser Arg Phe Pro Val Lys Met Asn Phe Phe Gln Arg
            180                 185                 190 atg ata aat acg ggt tgg cat ttg tat ttt ctg tac atg tac ttt tat     624
Met Ile Asn Thr Gly Trp His Leu Tyr Phe Leu Tyr Met Tyr Phe Tyr
        195                 200                 205 tat ggt aat gga gaa gat gcc aac aaa atg gcg aga aaa ttt ttt ggc     672
Tyr Gly Asn Gly Glu Asp Ala Asn Lys Met Ala Arg Lys Phe Phe Gly
    210                 215                 220 aac gac atg ccc gac ata aat gaa atg gtt ttt aat aca tct tta tta     720
Asn Asp Met Pro Asp Ile Asn Glu Met Val Phe Asn Thr Ser Leu Leu
225                 230                 235                 240 ttc gta aat act cac ttt tcg gtt gat atg cca tat cct ttg gtt cca     768
Phe Val Asn Thr His Phe Ser Val Asp Met Pro Tyr Pro Leu Val Pro
                245                 250                 255
```

```
aac tgc att gaa ata gga gga ata cat gta aaa gag cca caa cca ctg      816
Asn Cys Ile Glu Ile Gly Gly Ile His Val Lys Glu Pro Gln Pro Leu
        260                 265                 270 cct ttg gaa ata caa aaa ttc atg gac gaa gca gaa cat ggg gtc att      864
Pro Leu Glu Ile Gln Lys Phe Met Asp Glu Ala Glu His Gly Val Ile
    275                 280                 285 ttc ttc acg cta gga tca atg gtg cgt act tcc acg ttt cca aat caa      912
Phe Phe Thr Leu Gly Ser Met Val Arg Thr Ser Thr Phe Pro Asn Gln
290                 295                 300 act att caa gca ttt aag gaa gct ttt gcc gaa tta cct caa aga gtc      960
Thr Ile Gln Ala Phe Lys Glu Ala Phe Ala Glu Leu Pro Gln Arg Val
305                 310                 315                 320 tta tgg aag ttt gag aat gaa aat gag gat atg cca tca aat gta ctc     1008
Leu Trp Lys Phe Glu Asn Glu Asn Glu Asp Met Pro Ser Asn Val Leu
            325                 330                 335 ata agg aaa tgg ttt cca caa aat gat ata ttc ggt cat aag aat atc     1056
Ile Arg Lys Trp Phe Pro Gln Asn Asp Ile Phe Gly His Lys Asn Ile
        340                 345                 350 aaa gca ttc att agt cac ggt gga aat tct gga gct ctg gag gct gtt     1104
Lys Ala Phe Ile Ser His Gly Gly Asn Ser Gly Ala Leu Glu Ala Val
    355                 360                 365 cat ttc gga gta ccg ata att gga att cct tta ttc tac gat cag tac     1152
His Phe Gly Val Pro Ile Ile Gly Ile Pro Leu Phe Tyr Asp Gln Tyr
370                 375                 380 agg aat att ttg agt ttc gtt aaa gaa ggt gtt gcc gtt ctt ttg gat     1200
Arg Asn Ile Leu Ser Phe Val Lys Glu Gly Val Ala Val Leu Leu Asp
385                 390                 395                 400 gtg aat gat ctg acg aaa gat aat att tta tct tct gtc agg act gtt     1248
Val Asn Asp Leu Thr Lys Asp Asn Ile Leu Ser Ser Val Arg Thr Val
            405                 410                 415 gtt aat gat aag agt tac tca gaa cgt atg aaa gca ttg tca caa cta     1296
Val Asn Asp Lys Ser Tyr Ser Glu Arg Met Lys Ala Leu Ser Gln Leu
        420                 425                 430 ttc cga gat cga cca atg agt cct ctt gac aca gct gtt tac tgg aca     1344
Phe Arg Asp Arg Pro Met Ser Pro Leu Asp Thr Ala Val Tyr Trp Thr
    435                 440                 445 gaa tat gtc atc cgc cat aga gga gcc cat cac ctc aag acc gct ggc     1392
Glu Tyr Val Ile Arg His Arg Gly Ala His His Leu Lys Thr Ala Gly
450                 455                 460 gca ttt ttg cat tgg tat cag tat tta ctt ttg gac gtt att acc ttc     1440
Ala Phe Leu His Trp Tyr Gln Tyr Leu Leu Leu Asp Val Ile Thr Phe
465                 470                 475                 480 tta tta gtc aca ttc tgc gct ttt tgt ttt att gtg aaa tat ata tgt     1488
Leu Leu Val Thr Phe Cys Ala Phe Cys Phe Ile Val Lys Tyr Ile Cys
            485                 490                 495 aaa gct ctc att cat cat tat tgg agc agt tcg aaa tct gaa aag ttg     1536
Lys Ala Leu Ile His His Tyr Trp Ser Ser Ser Lys Ser Glu Lys Leu
        500                 505                 510 aaa aaa aat taa                                                     1548
Lys Lys Asn
        515

<210> SEQ ID NO 2
<211> LENGTH: 515
<212> TYPE: PRT
<213> ORGANISM: Artificial Sequence
<220> FEATURE:
<223> OTHER INFORMATION: Synthetic Construct

<400> SEQUENCE: 2

Met Glu Phe Arg Leu Leu Ile Leu Ala Leu Phe Ser Val Leu Met Ser
```

-continued

```
1               5                   10                  15
Thr Ser Asn Gly Ala Glu Ile Leu Ala Leu Phe Pro Ile His Gly Ile
                20                  25                  30
Ser Asn Tyr Asn Val Ala Glu Ala Leu Leu Lys Thr Leu Ala Asn Arg
                35                  40                  45
Gly His Asn Val Thr Val Val Thr Ser Phe Pro Gln Lys Lys Pro Val
                50                  55                  60
Pro Asn Leu Tyr Glu Ile Asp Val Ser Gly Ala Lys Gly Leu Ala Thr
 65                 70                  75                  80
Asn Ser Ile His Phe Glu Arg Leu Gln Thr Ile Ile Gln Asp Val Lys
                85                  90                  95
Ser Asn Phe Lys Asn Met Val Arg Leu Ser Arg Thr Tyr Cys Glu Ile
                100                 105                 110
Met Phe Ser Asp Pro Arg Val Leu Asn Ile Arg Asp Lys Lys Phe Asp
                115                 120                 125
Leu Val Ile Asn Ala Val Phe Gly Ser Asp Cys Asp Ala Gly Phe Ala
                130                 135                 140
Trp Lys Ser Gln Ala Pro Leu Ile Ser Ile Leu Asn Ala Arg His Thr
145                 150                 155                 160
Pro Trp Ala Leu His Arg Met Gly Asn Pro Ser Asn Pro Ala Tyr Met
                165                 170                 175
Pro Val Ile His Ser Arg Phe Pro Val Lys Met Asn Phe Phe Gln Arg
                180                 185                 190
Met Ile Asn Thr Gly Trp His Leu Tyr Phe Leu Tyr Met Tyr Phe Tyr
                195                 200                 205
Tyr Gly Asn Gly Glu Asp Ala Asn Lys Met Ala Arg Lys Phe Phe Gly
210                 215                 220
Asn Asp Met Pro Asp Ile Asn Glu Met Val Phe Asn Thr Ser Leu Leu
225                 230                 235                 240
Phe Val Asn Thr His Phe Ser Val Asp Met Pro Tyr Pro Leu Val Pro
                245                 250                 255
Asn Cys Ile Glu Ile Gly Gly Ile His Val Lys Glu Pro Gln Pro Leu
                260                 265                 270
Pro Leu Glu Ile Gln Lys Phe Met Asp Glu Ala Glu His Gly Val Ile
                275                 280                 285
Phe Phe Thr Leu Gly Ser Met Val Arg Thr Ser Thr Phe Pro Asn Gln
                290                 295                 300
Thr Ile Gln Ala Phe Lys Glu Ala Phe Ala Glu Leu Pro Gln Arg Val
305                 310                 315                 320
Leu Trp Lys Phe Glu Asn Glu Asn Glu Asp Met Pro Ser Asn Val Leu
                325                 330                 335
Ile Arg Lys Trp Phe Pro Gln Asn Asp Ile Phe Gly His Lys Asn Ile
                340                 345                 350
Lys Ala Phe Ile Ser His Gly Gly Asn Ser Gly Ala Leu Glu Ala Val
                355                 360                 365
His Phe Gly Val Pro Ile Ile Gly Ile Pro Leu Phe Tyr Asp Gln Tyr
                370                 375                 380
Arg Asn Ile Leu Ser Phe Val Lys Glu Gly Val Ala Val Leu Leu Asp
385                 390                 395                 400
Val Asn Asp Leu Thr Lys Asp Asn Ile Leu Ser Ser Val Arg Thr Val
                405                 410                 415
Val Asn Asp Lys Ser Tyr Ser Glu Arg Met Lys Ala Leu Ser Gln Leu
                420                 425                 430
```

```
Phe Arg Asp Arg Pro Met Ser Pro Leu Asp Thr Ala Val Tyr Trp Thr
        435                 440                 445

Glu Tyr Val Ile Arg His Arg Gly Ala His His Leu Lys Thr Ala Gly
    450                 455                 460

Ala Phe Leu His Trp Tyr Gln Tyr Leu Leu Leu Asp Val Ile Thr Phe
465                 470                 475                 480

Leu Leu Val Thr Phe Cys Ala Phe Cys Phe Ile Val Lys Tyr Ile Cys
                485                 490                 495

Lys Ala Leu Ile His His Tyr Trp Ser Ser Ser Lys Ser Glu Lys Leu
            500                 505                 510

Lys Lys Asn
        515

<210> SEQ ID NO 3
<211> LENGTH: 1548
<212> TYPE: DNA
<213> ORGANISM: Artificial Sequence
<220> FEATURE:
<223> OTHER INFORMATION: Yeast Optimized Sequence

<400> SEQUENCE: 3
atggaattca gattgttgat attggccttg ttctccgtat tgatgtctac ctctaatggt      60
gccgaaatct tggctttatt ccctattcat ggtatatcta actacaacgt agctgaagca     120
ttgttgaaga ctttggctaa cagaggtcac aacgttaccg ttgtaacttc atttccacaa     180
aagaaaccag ttcctaattt gtacgaaatt gatgtatcag gtgcaaaggg tttagccaca     240
aactccatcc atttcgaaag attgcaaacc atcatccaag atgtcaagag taacttcaag     300
aacatggtta gattgtctag aacatactgt gaaatcatgt tctcagaccc aagagttttg     360
aacatcagag ataaaaagtt tgacttggtt ataaacgccg tattcggttc agattgcgac     420
gctggttttg catggaaaag tcaagctcct ttaatatcta tcttgaatgc agacatacaa     480
ccatgggctt tgcacagaat gggtaatcct tccaacccag catatatgcc tgtaatccat     540
agtagattcc cagtcaagat gaatttcttt caaagaatga taaacaccgg ttggcactta     600 tacttttgt acatgtactt ctactacggt aatggtgaag atgctaacaa aatggcaaga     660 aagttttcg gtaatgatat gcctgacata aacgaaatgg ttttttaacac ctccttgttg     720 ttcgtaaaca ctcatttcag tgtcgatatg ccatacccct tagtcccaaa ctgtatcgaa     780
atcggtggta ccatgttaag gaaccacaa cctttgccat ggaaatcca aaagtttatg     840 gatgaagcag aacatggtgt aatcttttc accttgggta gtatggtcag aacttctaca     900
ttccctaatc aaactattca agcctttaaa gaagccttcg ctgaattacc acaaagagtt     960
ttgtggaagt tcgaaaacga aaacgaagat atgccttcca acgttttgat cagaaagtgg    1020
ttcccacaaa acgacatctt cggtcataag aacatcaagg ctttcatttc acacggtggt    1080
aattccggtg cctggaagc tgtccatttc ggtgttccta tcataggtat cccattgttt    1140
tatgatcaat acagaaacat cttgtctttc gttaagaag gtgtagctgt cttgttggat    1200
gtaaacgact taactaagga taacatcttg tcttcagtta gaacagtcgt taacgacaag    1260
tcatactccg aagaatgaa ggcattgtct caattgttta gagataggac tatgtcacca    1320
ttagacacag ctgtttattg gaccgaatac gtaattagac atagaggtgc acatcactta    1380
aaaactgcag gtgcctttt gcactggtat caatacttgt tgttggatgt catcactttt    1440
ttgttggtta cattctgtgc attctgcttc atcgttaagt acatctgcaa ggccttaatc    1500
```
catcactact ggtccagttc taaatctgaa aagttgaaaa agaattaa        1548

<210> SEQ ID NO 4
<211> LENGTH: 492
<212> TYPE: PRT
<213> ORGANISM: Artificial Sequence
<220> FEATURE:
<223> OTHER INFORMATION: Synthetic DNA

<400> SEQUENCE: 4

```
Met Gly Ser Asn Ala Pro Pro Pro Thr Pro His Val Val Leu Val
1               5                   10                  15

Pro Phe Pro Gly Gln Gly His Val Ala Pro Leu Met Gln Leu Ala Arg
            20                  25                  30

Leu Leu His Ala Arg Gly Ala Arg Val Thr Phe Val Tyr Thr Gln Tyr
        35                  40                  45

Asn Tyr Arg Arg Leu Leu Arg Ala Lys Gly Glu Ala Ala Val Arg Pro
    50                  55                  60

Pro Ala Thr Ser Ser Ala Arg Phe Arg Ile Glu Val Ile Asp Asp Gly
65                  70                  75                  80

Leu Ser Leu Ser Val Pro Gln Asn Asp Val Gly Gly Leu Val Asp Ser
                85                  90                  95

Leu Arg Lys Asn Cys Leu His Pro Phe Arg Ala Leu Leu Arg Arg Leu
            100                 105                 110

Gly Gln Glu Val Glu Gly Gln Asp Ala Pro Pro Val Thr Cys Val Val
        115                 120                 125

Gly Asp Val Val Met Thr Phe Ala Ala Ala Ala Arg Glu Ala Gly
130                 135                 140

Ile Pro Glu Val Gln Phe Phe Thr Ala Ser Ala Cys Gly Leu Leu Gly
145                 150                 155                 160

Tyr Leu His Tyr Gly Glu Leu Val Glu Arg Gly Leu Val Pro Phe Arg
                165                 170                 175

Asp Ala Ser Leu Leu Ala Asp Asp Tyr Leu Asp Thr Pro Leu Glu
            180                 185                 190

Trp Val Pro Gly Met Ser His Met Arg Leu Arg Asp Met Pro Thr Phe
        195                 200                 205

Cys Arg Thr Thr Asp Pro Asp Asp Val Met Val Ser Ala Thr Leu Gln
    210                 215                 220

Gln Met Glu Ser Ala Ala Gly Ser Lys Ala Leu Ile Leu Asn Thr Leu
225                 230                 235                 240

Tyr Glu Leu Glu Lys Asp Val Val Asp Ala Leu Ala Ala Phe Phe Pro
                245                 250                 255

Pro Ile Tyr Thr Val Gly Pro Leu Ala Glu Val Ile Ala Ser Ser Asp
            260                 265                 270

Ser Ala Ser Ala Gly Leu Ala Ala Met Asp Ile Ser Ile Trp Gln Glu
        275                 280                 285

Asp Thr Arg Cys Leu Ser Trp Leu Asp Gly Lys Pro Ala Gly Ser Val
    290                 295                 300

Val Tyr Val Asn Phe Gly Ser Met Ala Val Met Thr Ala Ala Gln Ala
305                 310                 315                 320

Arg Glu Phe Ala Leu Gly Leu Ala Ser Cys Gly Ser Pro Phe Leu Trp
                325                 330                 335

Val Lys Arg Pro Asp Val Val Glu Gly Glu Val Leu Leu Pro Glu
            340                 345                 350

Ala Leu Leu Asp Glu Val Ala Arg Gly Arg Gly Leu Val Val Pro Trp
```

-continued

```
                355                 360                 365
Cys Pro Gln Ala Ala Val Leu Lys His Ala Ala Val Gly Leu Phe Val
370                 375                 380

Ser His Cys Gly Trp Asn Ser Leu Leu Glu Ala Thr Ala Ala Gly Gln
385                 390                 395                 400

Pro Val Leu Ala Trp Pro Cys His Gly Glu Gln Thr Thr Asn Cys Arg
                405                 410                 415

Gln Leu Cys Glu Val Trp Gly Asn Gly Ala Gln Leu Pro Arg Glu Val
            420                 425                 430

Glu Ser Gly Ala Val Ala Arg Leu Val Arg Glu Met Met Val Gly Asp
        435                 440                 445

Leu Gly Lys Glu Lys Arg Ala Lys Ala Glu Trp Lys Ala Ala
    450                 455                 460

Glu Ala Ala Arg Lys Gly Gly Ala Ser Trp Arg Asn Val Glu Arg
465                 470                 475                 480

Val Val Asn Asp Leu Leu Leu Val Gly Gly Lys Gln
                485                 490

<210> SEQ ID NO 5
<211> LENGTH: 471
<212> TYPE: PRT
<213> ORGANISM: Artificial Sequence
<220> FEATURE:
<223> OTHER INFORMATION: Synthetic DNA

<400> SEQUENCE: 5

Met Pro Ser Ser Gly Asp Ala Ala Gly Arg Arg Pro His Val Val Leu
1               5                   10                  15

Ile Pro Ser Ala Gly Met Gly His Leu Val Pro Phe Gly Arg Leu Ala
                20                  25                  30

Val Ala Leu Ser Ser Gly His Gly Cys Asp Val Ser Leu Val Thr Val
            35                  40                  45

Leu Pro Thr Val Ser Thr Ala Glu Ser Lys His Leu Asp Ala Leu Phe
        50                  55                  60

Asp Ala Phe Pro Ala Val Arg Arg Leu Asp Phe Glu Leu Ala Pro Phe
65                  70                  75                  80

Asp Ala Ser Glu Phe Pro Gly Ala Asp Pro Phe Phe Leu Arg Phe Glu
                85                  90                  95

Ala Met Arg Arg Ser Ala Pro Leu Leu Gly Pro Leu Leu Thr Gly Ala
                100                 105                 110

Gly Ala Ser Ala Leu Ala Thr Asp Ile Ala Leu Thr Ser Val Val Ile
            115                 120                 125

Pro Val Ala Lys Glu Gln Gly Leu Pro Cys His Ile Leu Phe Thr Ala
        130                 135                 140

Ser Ala Ala Met Leu Ser Leu Cys Ala Tyr Phe Pro Thr Tyr Leu Asp
145                 150                 155                 160

Ala Asn Ala Gly Gly Gly Gly Val Gly Asp Val Asp Ile Pro Gly
                165                 170                 175

Val Tyr Arg Ile Pro Lys Ala Ser Ile Pro Gln Ala Leu His Asp Pro
            180                 185                 190

Asn His Leu Phe Thr Arg Gln Phe Val Ala Asn Gly Arg Ser Leu Thr
        195                 200                 205

Ser Ala Ala Gly Ile Leu Val Asn Thr Phe Asp Ala Leu Glu Pro Glu
    210                 215                 220

Ala Val Ala Ala Leu Gln Gln Gly Lys Val Ala Ser Gly Phe Pro Pro
```

```
            225                 230                 235                 240
        Val Phe Ala Val Gly Pro Leu Pro Ala Ser Asn Gln Ala Lys Asp
                        245                 250                 255

Pro Gln Ala Asn Tyr Met Glu Trp Leu Asp Ala Gln Pro Ala Arg Ser
                        260                 265                 270

Val Val Tyr Val Ser Phe Gly Ser Arg Lys Ala Ile Ser Arg Glu Gln
                    275                 280                 285

Leu Arg Glu Leu Ala Ala Gly Leu Glu Gly Ser Gly His Arg Phe Leu
                290                 295                 300

Trp Val Val Lys Ser Thr Val Val Asp Arg Asp Asp Ala Ala Glu Leu
        305                 310                 315                 320

Gly Glu Leu Leu Asp Glu Gly Phe Leu Glu Arg Val Glu Lys Arg Gly
                        325                 330                 335

Leu Val Thr Lys Ala Trp Val Asp Gln Glu Glu Val Leu Lys His Glu
                    340                 345                 350

Ser Val Ala Leu Phe Val Ser His Cys Gly Trp Asn Ser Val Thr Glu
                355                 360                 365

Ala Ala Ala Ser Gly Val Pro Val Leu Ala Leu Pro Arg Phe Gly Asp
            370                 375                 380

Gln Arg Val Asn Ser Gly Val Val Ala Arg Ala Gly Leu Gly Val Trp
        385                 390                 395                 400

Ala Asp Thr Trp Ser Trp Glu Gly Glu Ala Gly Val Ile Gly Ala Glu
                        405                 410                 415

Glu Ile Ser Glu Lys Val Lys Ala Ala Met Ala Asp Glu Ala Leu Arg
                    420                 425                 430

Met Lys Ala Ala Ser Leu Ala Glu Ala Ala Lys Ala Val Ala Gly
                435                 440                 445

Gly Gly Ser Ser His Arg Cys Leu Ala Glu Phe Ala Arg Leu Cys Gln
            450                 455                 460

Gly Gly Thr Cys Arg Thr Asn
        465                 470

<210> SEQ ID NO 6
<211> LENGTH: 1212
<212> TYPE: DNA
<213> ORGANISM: Artificial Sequence
<220> FEATURE:
<223> OTHER INFORMATION: Synthetic DNA

<400> SEQUENCE: 6
atgagttcac tctccaacgc ttcccatctg atggaggatg tgcagggcat ccggaaggcc      60
cagagagccg atggcacggc accgtcatg gccatcggaa cagctcaccc tcctcatatc     120
tttcctcagg acacctacgc tgacttctac ttccgcgcca ccaacagcga gcacaaggtc     180
gagctcaaga gaagttcga tcgcatctgc aaaaagacaa tgataggcaa cgctacttc     240 aactacgacg aggagttctt gaagaaatat cccaatatca cttcattcga tgagcccagc     300
ctcaacgacc gccaggacat tgtgtccct ggggtgccag ccctgggagc cgaagcagct     360
gtgaaagcca tcgcggaatg gggacgcccc aagtctgaga ttactcatct cgtgttctgc     420
acctcctgcg gtgtcgacat gcccagcgcc gacttccagt cgccaagct ccttggcctc     480 cgcaccaatg tcaacaagta ctgcgtctac atgcaaggat gctatgctgg tggcaccgtc     540
atgcggtatg ccaaggatct ggccgagaac aaccgtggtg ctcgtgtttt ggtggtgtgt     600
gcggagctca ccataatcgg gcttcgaggc cctaatgagt cccatctcga caacgccatc     660
```

```
ggaaattctc ttttcggaga tggagctgcc gcgttgatcg tcgggtcgga ccccatcatc    720
ggtgtcgaga agcccatgtt cgagatcgtg tgtgccaagc aaactgtgat cccaaacagc    780
gaagacgtta tccatctcca catgagagag gcaggtctga tgttctacat gagcaaggac    840
agtcccgaga ccatctccaa taacgtagag gcttgcctcg ttgatgtgtt caagtctgtg    900
gggatgactc ctcccgagga ctggaactct ctcttctgga tccctcaccc cggtggtcgc    960
gccatccttg atcaagttga ggccaagctg aagcttcgtc ctgagaagtt ccgtgcgact   1020
cgaaccgtgc tctgggattg cggtaacatg gtcagtgcgt gtgtgctcta catattggat   1080
gagatgagaa gaaatccgc tgatgaagga ctagagacct acggagaggg actagagtgg    1140
ggtgtcttgc ttggatttgg accagggatg accgttgaaa ctatccttct ccacagcctg   1200
cctctcatgt ga                                                       1212
```

<210> SEQ ID NO 7
<211> LENGTH: 403
<212> TYPE: PRT
<213> ORGANISM: Artificial Sequence
<220> FEATURE:
<223> OTHER INFORMATION: Synthetic DNA

<400> SEQUENCE: 7

```
Met Ser Ser Leu Ser Asn Ala Ser His Leu Met Glu Asp Val Gln Gly
1               5                   10                  15

Ile Arg Lys Ala Gln Arg Ala Asp Gly Thr Ala Thr Val Met Ala Ile
            20                  25                  30

Gly Thr Ala His Pro Pro His Ile Phe Pro Gln Asp Thr Tyr Ala Asp
        35                  40                  45

Phe Tyr Phe Arg Ala Thr Asn Ser Glu His Lys Val Glu Leu Lys Lys
    50                  55                  60

Lys Phe Asp Arg Ile Cys Lys Lys Thr Met Ile Gly Lys Arg Tyr Phe
65                  70                  75                  80

Asn Tyr Asp Glu Glu Phe Leu Lys Lys Tyr Pro Asn Ile Thr Ser Phe
                85                  90                  95

Asp Glu Pro Ser Leu Asn Asp Arg Gln Asp Ile Cys Val Pro Gly Val
            100                 105                 110

Pro Ala Leu Gly Ala Glu Ala Ala Val Lys Ala Ile Ala Glu Trp Gly
        115                 120                 125

Arg Pro Lys Ser Glu Ile Thr His Leu Val Phe Cys Thr Ser Cys Gly
    130                 135                 140

Val Asp Met Pro Ser Ala Asp Phe Gln Cys Ala Lys Leu Leu Gly Leu
145                 150                 155                 160

Arg Thr Asn Val Asn Lys Tyr Cys Val Tyr Met Gln Gly Cys Tyr Ala
                165                 170                 175

Gly Gly Thr Val Met Arg Tyr Ala Lys Asp Leu Ala Glu Asn Asn Arg
            180                 185                 190

Gly Ala Arg Val Leu Val Val Cys Ala Glu Leu Thr Ile Ile Gly Leu
        195                 200                 205

Arg Gly Pro Asn Glu Ser His Leu Asp Asn Ala Ile Gly Asn Ser Leu
    210                 215                 220

Phe Gly Asp Gly Ala Ala Ala Leu Ile Val Gly Ser Asp Pro Ile Ile
225                 230                 235                 240

Gly Val Glu Lys Pro Met Phe Glu Ile Val Cys Ala Lys Gln Thr Val
                245                 250                 255

Ile Pro Asn Ser Glu Asp Val Ile His Leu His Met Arg Glu Ala Gly
```

```
                    260                 265                 270
Leu Met Phe Tyr Met Ser Lys Asp Ser Pro Glu Thr Ile Ser Asn Asn
            275                 280                 285

Val Glu Ala Cys Leu Val Asp Val Phe Lys Ser Val Gly Met Thr Pro
        290                 295                 300

Pro Glu Asp Trp Asn Ser Leu Phe Trp Ile Pro His Pro Gly Gly Arg
305                 310                 315                 320

Ala Ile Leu Asp Gln Val Glu Ala Lys Leu Lys Leu Arg Pro Glu Lys
                325                 330                 335

Phe Arg Ala Thr Arg Thr Val Leu Trp Asp Cys Gly Asn Met Val Ser
            340                 345                 350

Ala Cys Val Leu Tyr Ile Leu Asp Glu Met Arg Arg Lys Ser Ala Asp
        355                 360                 365

Glu Gly Leu Glu Thr Tyr Gly Glu Gly Leu Glu Trp Gly Val Leu Leu
    370                 375                 380

Gly Phe Gly Pro Gly Met Thr Val Glu Thr Ile Leu Leu His Ser Leu
385                 390                 395                 400

Pro Leu Met
```

<210> SEQ ID NO 8
<211> LENGTH: 1212
<212> TYPE: DNA
<213> ORGANISM: Artificial Sequence
<220> FEATURE:
<223> OTHER INFORMATION: Synthetic DNA

<400> SEQUENCE: 8

```
atgggttcac tctccaacta ctcgccagtg atggaggatg tgcaggccat ccgaaaggcc      60
caaaaagcag atggaaccgc aacagtgatg gccatcggaa cagctcaccc tcctcatatc     120
tttcctcagg acacctacgc cgacttctac ttccgcgcca ccaacagcga gcacaaagtc     180
gagctcaaga gaaattcga tcgtatctgc aaaaagacaa tgataggcaa cgctacttc      240
aattacgatg aggagttcct caagaagtat cccaacatta cctcattcga cgagcccagc     300
ctcaacgacc gccaggatat ttgcgtccct ggggtgccgg ccctgggagc cgaagcagct     360
gtcaaagcca tcgctgaatg ggacgtccaa agtctgaga tcactcatct cgtcttctgc     420
acctcctgcg tgtcgacat gcctagcgcc gacttccagt cgccaagct cctcggcctc      480
cgcaccaatg tcaacaagta ttgcgtctac atgcagggat gctatgctgg cggcacagtc     540
atgcggtacg ccaaggatct cgccgagaac aaccgtggtg ctcgtgttct agtggtgtgc     600
gccgagctca ccatcatcgg gcttcgcgga ccaaatgagt cccatctcga caacgccatc     660
ggcaactccc ttttcggaga cggagctgct cgctgatcg tcgggtcaga ccccatcatt      720
ggtgtcgaga ggcctatgtt cgagatcgtg tgcgcaaagc agaccgtgat cccaaacagt     780
gaagatgtta ccatctcca catgagggag gcgggtctaa tgttctacat gagcaaggac     840
agccccgaga ccatctccaa caatgtagag gcatgccttg tcgatgtgtt caagtcggtg     900
ggatgactc ctcccgagga ctggaactct ctcttctgga tccctcaccc cggcggtcga     960
gctatcctcg accaggttga ggccaggctt aagcttcgtc cgagaagtt cggcgcgact    1020
cgaactgtgc tctgggattg cggaaacatg gtgagcgcgt gttctcta catttttggat    1080
gagatgagaa gaaatctcgt tgccgacgga ctagcaacct acggagaggg gctggagtgg    1140
ggtgtcttgc ttggtttcgg accagggatg accgttgaaa ctatccttct ccacagcctg   1200
ccccctgtgt aa                                                       1212
```

<210> SEQ ID NO 9
<211> LENGTH: 403
<212> TYPE: PRT
<213> ORGANISM: Artificial Sequence
<220> FEATURE:
<223> OTHER INFORMATION: Synthetic DNA

<400> SEQUENCE: 9

Met Gly Ser Leu Ser Asn Tyr Ser Pro Val Met Glu Asp Val Gln Ala
1               5                   10                  15

Ile Arg Lys Ala Gln Lys Ala Asp Gly Thr Ala Thr Val Met Ala Ile
            20                  25                  30

Gly Thr Ala His Pro Pro His Ile Phe Pro Gln Asp Thr Tyr Ala Asp
        35                  40                  45

Phe Tyr Phe Arg Ala Thr Asn Ser Glu His Lys Val Glu Leu Lys Lys
    50                  55                  60

Lys Phe Asp Arg Ile Cys Lys Lys Thr Met Ile Gly Lys Arg Tyr Phe
65                  70                  75                  80

Asn Tyr Asp Glu Glu Phe Leu Lys Lys Tyr Pro Asn Ile Thr Ser Phe
                85                  90                  95

Asp Glu Pro Ser Leu Asn Asp Arg Gln Asp Ile Cys Val Pro Gly Val
            100                 105                 110

Pro Ala Leu Gly Ala Glu Ala Ala Val Lys Ala Ile Ala Glu Trp Gly
        115                 120                 125

Arg Pro Lys Ser Glu Ile Thr His Leu Val Phe Cys Thr Ser Cys Gly
    130                 135                 140

Val Asp Met Pro Ser Ala Asp Phe Gln Cys Ala Lys Leu Leu Gly Leu
145                 150                 155                 160

Arg Thr Asn Val Asn Lys Tyr Cys Val Tyr Met Gln Gly Cys Tyr Ala
                165                 170                 175

Gly Gly Thr Val Met Arg Tyr Ala Lys Asp Leu Ala Glu Asn Asn Arg
            180                 185                 190

Gly Ala Arg Val Leu Val Val Cys Ala Glu Leu Thr Ile Ile Gly Leu
        195                 200                 205

Arg Gly Pro Asn Glu Ser His Leu Asp Asn Ala Ile Gly Asn Ser Leu
    210                 215                 220

Phe Gly Asp Gly Ala Ala Ala Leu Ile Val Gly Ser Asp Pro Ile Ile
225                 230                 235                 240

Gly Val Glu Arg Pro Met Phe Glu Ile Val Cys Ala Lys Gln Thr Val
                245                 250                 255

Ile Pro Asn Ser Glu Asp Val Ile His Leu His Met Arg Glu Ala Gly
            260                 265                 270

Leu Met Phe Tyr Met Ser Lys Asp Ser Pro Glu Thr Ile Ser Asn Asn
        275                 280                 285

Val Glu Ala Cys Leu Val Asp Val Phe Lys Ser Val Gly Met Thr Pro
    290                 295                 300

Pro Glu Asp Trp Asn Ser Leu Phe Trp Ile Pro His Pro Gly Gly Arg
305                 310                 315                 320

Ala Ile Leu Asp Gln Val Glu Ala Arg Leu Lys Leu Arg Pro Glu Lys
                325                 330                 335

Phe Gly Ala Thr Arg Thr Val Leu Trp Asp Cys Gly Asn Met Val Ser
            340                 345                 350

Ala Cys Val Leu Tyr Ile Leu Asp Glu Met Arg Arg Lys Ser Val Ala
        355                 360                 365

Asp Gly Leu Ala Thr Tyr Gly Glu Gly Leu Glu Trp Gly Val Leu Leu
            370                 375                 380

Gly Phe Gly Pro Gly Met Thr Val Glu Thr Ile Leu Leu His Ser Leu
385                 390                 395                 400

Pro Pro Val

<210> SEQ ID NO 10
<211> LENGTH: 1218
<212> TYPE: DNA
<213> ORGANISM: Artificial Sequence
<220> FEATURE:
<223> OTHER INFORMATION: Synthetic DNA

<400> SEQUENCE: 10

| | | |
|---|---|---|
| atgggttcga tcgccgagtc ttcaccactg atgagtaggg agaatgtgga gggcatcaga | 60 |
| aaagcgcaga gagctgaggg aaccgcaact gtgatggcca tcggaactgc tcaccctccc | 120 |
| catatctttc ctcaggacac ctacgcagac ttctacttcc gcgccaccaa cagcgagcac | 180 |
| aaagttgagc tcaagaagaa gttcgaccga atctgcaaaa agacaatgat tggcaaacgc | 240 |
| tacttcaact acgacgagga gttcctcaag aagtacccaa acatcacatc cttcgacgag | 300 |
| cccagcctga acgaccgcca ggacatctgc gtccccggag tccccgcctt gggtaaggag | 360 |
| gccgctctca aagccatcga ggaatggggg caacctctgt ccaagatcac ccatctcgtc | 420 |
| ttctgcacct cctgcgcgt cgacatgccc agcgccgatt ccagctcgc caagctcctc | 480 |
| ggactcaaca ccaacgtcaa caagtactgc gtctacatgc agggctgcta cgccggcggc | 540 |
| accgtcctcc gctacgccaa ggacctcgcc gagaacaacc gcggctcccg cgtcctcgtc | 600 |
| gtctgcgccg agctcaccat catcggcctc cgcggcccaa cgagtccca cctcgacaac | 660 |
| gccatcggga actccctctt cggcgacggg gccgccgcgc tcatcgtggg cgccgatcct | 720 |
| attgttggca tagagaagcc catcttcgag atcgtctgcg caaagcagac cgtcatcccc | 780 |
| gacagcgagg acgtcatcca cctccacctc cgcgaggccg gcctcatgtt ctacatgagc | 840 |
| aaggacagcc ccgagaccat ctccaacaac gtcgagggct gcctcgtcga catcttcaag | 900 |
| tccgtcggca tgaccccgcc cgccgactgg aactccctct ctggatccc ccaccccggc | 960 |
| ggccgagcca tcctcgacga ggtcgaggcc aggctcaagc tccgcccgga aagtttaga | 1020 |
| gcaaccaggc acgtgctctg ggagtacggg aacatggtca cgcatgcgt tctctacata | 1080 |
| ctggacgaga tgaggaacaa gtccgcagcc gacggattgg ggacctacgg agaaggactc | 1140 |
| gaatggggcg tcttgctcgg tttcggaccc ggaatgaccg tcgagaccat cctcctccac | 1200 |
| agcctgcctc ctgtctaa | 1218 |

<210> SEQ ID NO 11
<211> LENGTH: 405
<212> TYPE: PRT
<213> ORGANISM: Artificial Sequence
<220> FEATURE:
<223> OTHER INFORMATION: Synthetic DNA

<400> SEQUENCE: 11

Met Gly Ser Ile Ala Glu Ser Ser Pro Leu Met Ser Arg Glu Asn Val
1               5                   10                  15

Glu Gly Ile Arg Lys Ala Gln Arg Ala Glu Gly Thr Ala Thr Val Met
            20                  25                  30

Ala Ile Gly Thr Ala His Pro Pro His Ile Phe Pro Gln Asp Thr Tyr
        35                  40                  45

Ala Asp Phe Tyr Phe Arg Ala Thr Asn Ser Glu His Lys Val Glu Leu
 50                  55                  60

Lys Lys Lys Phe Asp Arg Ile Cys Lys Lys Thr Met Ile Gly Lys Arg
 65                  70                  75                  80

Tyr Phe Asn Tyr Asp Glu Glu Phe Leu Lys Lys Tyr Pro Asn Ile Thr
                 85                  90                  95

Ser Phe Asp Glu Pro Ser Leu Asn Asp Arg Gln Asp Ile Cys Val Pro
                100                 105                 110

Gly Val Pro Ala Leu Gly Lys Glu Ala Ala Leu Lys Ala Ile Glu Glu
            115                 120                 125

Trp Gly Gln Pro Leu Ser Lys Ile Thr His Leu Val Phe Cys Thr Ser
130                 135                 140

Cys Gly Val Asp Met Pro Ser Ala Asp Phe Gln Leu Ala Lys Leu Leu
145                 150                 155                 160

Gly Leu Asn Thr Asn Val Asn Lys Tyr Cys Val Tyr Met Gln Gly Cys
                165                 170                 175

Tyr Ala Gly Gly Thr Val Leu Arg Tyr Ala Lys Asp Leu Ala Glu Asn
            180                 185                 190

Asn Arg Gly Ser Arg Val Leu Val Val Cys Ala Glu Leu Thr Ile Ile
        195                 200                 205

Gly Leu Arg Gly Pro Asn Glu Ser His Leu Asp Asn Ala Ile Gly Asn
210                 215                 220

Ser Leu Phe Gly Asp Gly Ala Ala Ala Leu Ile Val Gly Ala Asp Pro
225                 230                 235                 240

Ile Val Gly Ile Glu Lys Pro Ile Phe Glu Ile Val Cys Ala Lys Gln
                245                 250                 255

Thr Val Ile Pro Asp Ser Glu Asp Val Ile His Leu His Leu Arg Glu
            260                 265                 270

Ala Gly Leu Met Phe Tyr Met Ser Lys Asp Ser Pro Glu Thr Ile Ser
        275                 280                 285

Asn Asn Val Glu Gly Cys Leu Val Asp Ile Phe Lys Ser Val Gly Met
290                 295                 300

Thr Pro Pro Ala Asp Trp Asn Ser Leu Phe Trp Ile Pro His Pro Gly
305                 310                 315                 320

Gly Arg Ala Ile Leu Asp Glu Val Glu Ala Arg Leu Lys Leu Arg Pro
                325                 330                 335

Glu Lys Phe Arg Ala Thr Arg His Val Leu Trp Glu Tyr Gly Asn Met
            340                 345                 350

Val Ser Ala Cys Val Leu Tyr Ile Leu Asp Glu Met Arg Asn Lys Ser
        355                 360                 365

Ala Ala Asp Gly Leu Gly Thr Tyr Gly Glu Gly Leu Glu Trp Gly Val
370                 375                 380

Leu Leu Gly Phe Gly Pro Gly Met Thr Val Glu Thr Ile Leu Leu His
385                 390                 395                 400

Ser Leu Pro Pro Val
            405

<210> SEQ ID NO 12
<211> LENGTH: 1212
<212> TYPE: DNA
<213> ORGANISM: Artificial Sequence
<220> FEATURE:
<223> OTHER INFORMATION: Synthetic DNA

<400> SEQUENCE: 12

```
atgggtagtt tatctgactc cactccattg atgaaggatg tccaaggtat tagaaaagca      60
caaaaagccg acggtacagc aacagttatg gccattggta ccgctcatcc acctcacata     120
atctctcaag attcatacgc agacttctac ttcagagtta caaactcaga acataaggtc     180
gaattaaaaa agaaattcga tagaatctgt aagaaaacca tgataggcaa agatacttc     240
aacttcgatg aagaattctt gaagaaatac ccaaacataa catccttcga caaacctagt     300
ttaaacgata gacatgacat ttgcatacca ggtgttcctg ctttgggtgc agaagctgca     360
gtcaaggcaa tagaagaatg gggtagacca aagtccgaaa taacacactt ggtattttgt     420
acctccggtg gtgttgatat gcctagtgct gacttccaat gcgcaaagtt gttaggtttg     480
agaaccaacg tcaacaagta ctgtatctac atgcaaggtt gctacgctgg tggtactgtt     540
atgagatacg caaagatttt ggccgaaaat aacagaggtg ccagagtatt aatggtttgt     600
gctgaattga ctatcattgg tttaagaggt ccaaatgatt ctcatataga caatgccatc     660
ggtaactcat gtttggtgat ggtgccgct gcattaattg tcggttcaga cccaataatc     720
ggtgtagaaa agcctatgtt cgaaattgtc tgtgctaaac aaactgtaat acctaattcc     780
gaagaagtta tccatttgca cttgagagaa agtggtttga tgttctacat gactaaggat     840
tctgccgcta caatatcaaa aacatcgaa gcttgcttgg ttgatgtctt taaatctgtt     900
ggtatgacac cacctgaaga ctggaattca ttgttctgga tcccacatcc tggtggtaga     960
gcaattttag atcaagttga agccaagttg aaattaagac cagaaaagtt ttccgctact    1020
agaacagtat tatgggatta tggtaacatg atcagtgcat gtgttttgta catcttggat    1080
gaaatgagaa gaaagtctgc agccgaaggt ttggaaacat acggtgaagg tttagaatgg    1140
ggtgttttgt taggtttcgg tcctggtatg accatcgaaa ctatttttgtt acactctttg    1200
ccacctgttt aa                                                         1212
```

<210> SEQ ID NO 13
<211> LENGTH: 403
<212> TYPE: PRT
<213> ORGANISM: Artificial Sequence
<220> FEATURE:
<223> OTHER INFORMATION: Synthetic DNA

<400> SEQUENCE: 13

```
Met Gly Ser Leu Ser Asp Ser Thr Pro Leu Met Lys Asp Val Gln Gly
1               5                   10                  15

Ile Arg Lys Ala Gln Lys Ala Asp Gly Thr Ala Thr Val Met Ala Ile
            20                  25                  30

Gly Thr Ala His Pro Pro His Ile Ile Ser Gln Asp Ser Tyr Ala Asp
        35                  40                  45

Phe Tyr Phe Arg Val Thr Asn Ser Glu His Lys Val Glu Leu Lys Lys
    50                  55                  60

Lys Phe Asp Arg Ile Cys Lys Lys Thr Met Ile Gly Lys Arg Tyr Phe
65                  70                  75                  80

Asn Phe Asp Glu Glu Phe Leu Lys Lys Tyr Pro Asn Ile Thr Ser Phe
                85                  90                  95

Asp Lys Pro Ser Leu Asn Asp Arg His Asp Ile Cys Ile Pro Gly Val
            100                 105                 110

Pro Ala Leu Gly Ala Glu Ala Ala Val Lys Ala Ile Glu Glu Trp Gly
        115                 120                 125

Arg Pro Lys Ser Glu Ile Thr His Leu Val Phe Cys Thr Ser Gly Gly
    130                 135                 140
```

Val Asp Met Pro Ser Ala Asp Phe Gln Cys Ala Lys Leu Leu Gly Leu
145                 150                 155                 160

Arg Thr Asn Val Asn Lys Tyr Cys Ile Tyr Met Gln Gly Cys Tyr Ala
                165                 170                 175

Gly Gly Thr Val Met Arg Tyr Ala Lys Asp Leu Ala Glu Asn Asn Arg
            180                 185                 190

Gly Ala Arg Val Leu Met Val Cys Ala Glu Leu Thr Ile Ile Gly Leu
        195                 200                 205

Arg Gly Pro Asn Asp Ser His Ile Asp Asn Ala Ile Gly Asn Ser Leu
    210                 215                 220

Phe Gly Asp Gly Ala Ala Leu Ile Val Gly Ser Asp Pro Ile Ile
225                 230                 235                 240

Gly Val Glu Lys Pro Met Phe Glu Ile Val Cys Ala Lys Gln Thr Val
                245                 250                 255

Ile Pro Asn Ser Glu Glu Val Ile His Leu His Leu Arg Glu Ser Gly
                260                 265                 270

Leu Met Phe Tyr Met Thr Lys Asp Ser Ala Ala Thr Ile Ser Asn Asn
            275                 280                 285

Ile Glu Ala Cys Leu Val Asp Val Phe Lys Ser Val Gly Met Thr Pro
290                 295                 300

Pro Glu Asp Trp Asn Ser Leu Phe Trp Ile Pro His Pro Gly Gly Arg
305                 310                 315                 320

Ala Ile Leu Asp Gln Val Glu Ala Lys Leu Lys Leu Arg Pro Glu Lys
                325                 330                 335

Phe Ser Ala Thr Arg Thr Val Leu Trp Asp Tyr Gly Asn Met Ile Ser
            340                 345                 350

Ala Cys Val Leu Tyr Ile Leu Asp Glu Met Arg Arg Lys Ser Ala Ala
        355                 360                 365

Glu Gly Leu Glu Thr Tyr Gly Glu Gly Leu Trp Gly Val Leu Leu
    370                 375                 380

Gly Phe Gly Pro Gly Met Thr Ile Glu Thr Ile Leu Leu His Ser Leu
385                 390                 395                 400

Pro Pro Val

<210> SEQ ID NO 14
<211> LENGTH: 1182
<212> TYPE: DNA
<213> ORGANISM: Artificial Sequence
<220> FEATURE:
<223> OTHER INFORMATION: Synthetic DNA

<400> SEQUENCE: 14
atgggttccc ttgacaatgg ttcagctaga attaacaacc agaaatctaa tgggttggct    60
tcaattttgg ccattggaac tgcacttccg ccgatttgca ttaagcaaga tgactatcct   120
gattactact tccgagtcac caaaagcgac acaagacgc aactgaaaga gaagtttcgt    180
cgcatctgtg aaaagtcagg agtgacaaaa cgatacacag tactaaccga agacatgatc   240
aaggagaacg agaacataat aacctacaag gctccgtcac tggatgctcg ccaagcgatc   300
ctacacaagg agacacccaa gctcgccata gaagcagcct tgaagaccat caagaatgg    360 ggccaacccg tctctaagat cacccacctg ttcttttgct cctcctctgg cggctgctat   420
cttccgagct ccgattttca gatcgctaag gcactcggcc tcgagccgac cgtccagagg   480
tccatggtgt tcctcatgg atgctatgct gccagttctg gcctgcgttt ggccaaggac   540

```
attgcagaga acaacaaaga tgcacgcgtg ctggtggtgt gctgcgagtt gatggtgtcg    600
agcttccatg caccatcgga ggacgcgatc ggaatgctaa taggtcatgc catcttcggc    660
gatggagcgg cctgcgcaat tgtaggagca gacccggggc ctacggagcg cccaatattc    720
gagctagtga agggcggaca ggtgatcgtc ccagacacgg aagactgtct ggagggtgg     780 gtgatggaga tgggatggat ctacgatctc aacaagcgcc ttcctcaagc cctagccgac    840
aacatcctcg gagccctaga tgacaccctg aggctgacag gtaaaaggga tgacctcaat    900
ggccttttct acgtgctcca cccgggtggg cgggccatca tcgacctgct tgaggagaag    960
cttgagctaa caaaggacaa gctcgagagt agccgtcgtg tgctcagcaa ctatggcaac   1020
atgtggggcc ctgcgctagt gttcacgctc gacgagatga ggaggaagtc aaaggaggac   1080
aacgccacca ccactggtgg cgggtccgag ctcggcctga tgatggcgtt tggacctggc   1140
ctcaccaccg agatcatggt tctccgaagt gtgcctctct aa                      1182
```

<210> SEQ ID NO 15
<211> LENGTH: 393
<212> TYPE: PRT
<213> ORGANISM: Artificial Sequence
<220> FEATURE:
<223> OTHER INFORMATION: Synthetic DNA

<400> SEQUENCE: 15

```
Met Gly Ser Leu Asp Asn Gly Ser Ala Arg Ile Asn Asn Gln Lys Ser
1               5                   10                  15

Asn Gly Leu Ala Ser Ile Leu Ala Ile Gly Thr Ala Leu Pro Pro Ile
            20                  25                  30

Cys Ile Lys Gln Asp Asp Tyr Pro Asp Tyr Tyr Phe Arg Val Thr Lys
        35                  40                  45

Ser Asp His Lys Thr Gln Leu Lys Glu Lys Phe Arg Arg Ile Cys Glu
    50                  55                  60

Lys Ser Gly Val Thr Lys Arg Tyr Thr Val Leu Thr Glu Asp Met Ile
65                  70                  75                  80

Lys Glu Asn Glu Asn Ile Ile Thr Tyr Lys Ala Pro Ser Leu Asp Ala
                85                  90                  95

Arg Gln Ala Ile Leu His Lys Glu Thr Pro Lys Leu Ala Ile Glu Ala
            100                 105                 110

Ala Leu Lys Thr Ile Gln Glu Trp Gly Gln Pro Val Ser Lys Ile Thr
        115                 120                 125

His Leu Phe Phe Cys Ser Ser Ser Gly Gly Cys Tyr Leu Pro Ser Ser
    130                 135                 140

Asp Phe Gln Ile Ala Lys Ala Leu Gly Leu Glu Pro Thr Val Gln Arg
145                 150                 155                 160

Ser Met Val Phe Pro His Gly Cys Tyr Ala Ala Ser Ser Gly Leu Arg
                165                 170                 175

Leu Ala Lys Asp Ile Ala Glu Asn Asn Lys Asp Ala Arg Val Leu Val
            180                 185                 190

Val Cys Cys Glu Leu Met Val Ser Ser Phe His Ala Pro Ser Glu Asp
        195                 200                 205

Ala Ile Gly Met Leu Ile Gly His Ala Ile Phe Gly Asp Gly Ala Ala
    210                 215                 220

Cys Ala Ile Val Gly Ala Asp Pro Gly Pro Thr Glu Arg Pro Ile Phe
225                 230                 235                 240

Glu Leu Val Lys Gly Gly Gln Val Ile Val Pro Asp Thr Glu Asp Cys
                245                 250                 255
```

Leu Gly Gly Trp Val Met Glu Met Gly Trp Ile Tyr Asp Leu Asn Lys
                260                 265                 270

Arg Leu Pro Gln Ala Leu Ala Asp Asn Ile Leu Gly Ala Leu Asp Asp
            275                 280                 285

Thr Leu Arg Leu Thr Gly Lys Arg Asp Asp Leu Asn Gly Leu Phe Tyr
        290                 295                 300

Val Leu His Pro Gly Gly Arg Ala Ile Ile Asp Leu Leu Glu Glu Lys
305                 310                 315                 320

Leu Glu Leu Thr Lys Asp Lys Leu Glu Ser Ser Arg Arg Val Leu Ser
                325                 330                 335

Asn Tyr Gly Asn Met Trp Gly Pro Ala Leu Val Phe Thr Leu Asp Glu
            340                 345                 350

Met Arg Arg Lys Ser Lys Glu Asp Asn Ala Thr Thr Thr Gly Gly Gly
        355                 360                 365

Ser Glu Leu Gly Leu Met Met Ala Phe Gly Pro Gly Leu Thr Thr Glu
370                 375                 380

Ile Met Val Leu Arg Ser Val Pro Leu
385                 390

<210> SEQ ID NO 16
<211> LENGTH: 510
<212> TYPE: DNA
<213> ORGANISM: Artificial Sequence
<220> FEATURE:
<223> OTHER INFORMATION: Synthetic DNA

<400> SEQUENCE: 16
atgagacacg ttgaacacac agttaccgtt gccgctccag cagatttggt ttgggaagtt      60
ttagccgatg tattaggtta cgcagatata ttcccaccta cagaaaaggt tgaaatcttg     120
gaagaaggtc aaggttacca agttgtaaga ttgcatgtag atgtcgccgg tgaaattaat     180
acttggacat ctagaagaga tttggaccca gctagaagag ttatcgcata cagacaatta     240
gaaacagcac ctattgtagg tcatatgtct ggtgaatgga gagcctttac cttggatgct     300
gaaagaaaca aattggtctt aacccacgac ttcgttacta gagctgcagg tgacgacggt     360
ttggttgctg gtaaattaac tccagatgaa gcaagagaaa tgttagaagc cgtcgttgaa     420
agaaaattcc gtagcagactt gaacgccgtc ttaggtgaag ctgaaagaag agttagagcc     480
gctggtggtg ttggtaccgt aactgcataa                                     510

<210> SEQ ID NO 17
<211> LENGTH: 169
<212> TYPE: PRT
<213> ORGANISM: Artificial Sequence
<220> FEATURE:
<223> OTHER INFORMATION: Synthetic DNA

<400> SEQUENCE: 17

Met Arg His Val Glu His Thr Val Thr Val Ala Ala Pro Ala Asp Leu
1               5                  10                  15

Val Trp Glu Val Leu Ala Asp Val Leu Gly Tyr Ala Asp Ile Phe Pro
            20                  25                  30

Pro Thr Glu Lys Val Glu Ile Leu Glu Glu Gly Gln Gly Tyr Gln Val
        35                  40                  45

Val Arg Leu His Val Asp Val Ala Gly Glu Ile Asn Thr Trp Thr Ser
    50                  55                  60

Arg Arg Asp Leu Asp Pro Ala Arg Arg Val Ile Ala Tyr Arg Gln Leu

```
                 65                  70                  75                  80
Glu Thr Ala Pro Ile Val Gly His Met Ser Gly Glu Trp Arg Ala Phe
                         85                  90                  95
Thr Leu Asp Ala Glu Arg Thr Gln Leu Val Leu Thr His Asp Phe Val
                    100                 105                 110
Thr Arg Ala Ala Gly Asp Asp Gly Leu Val Ala Gly Lys Leu Thr Pro
                    115                 120                 125
Asp Glu Ala Arg Glu Met Leu Glu Ala Val Val Glu Arg Asn Ser Val
                130                 135                 140
Ala Asp Leu Asn Ala Val Leu Gly Glu Ala Glu Arg Arg Val Arg Ala
145                 150                 155                 160
Ala Gly Gly Val Gly Thr Val Thr Ala
                165

<210> SEQ ID NO 18
<211> LENGTH: 771
<212> TYPE: DNA
<213> ORGANISM: Artificial Sequence
<220> FEATURE:
<223> OTHER INFORMATION: Synthetic DNA

<400> SEQUENCE: 18
atgtccggta gaaagacctt tttagatttg tcatttgcca ccagagatac accatccgaa     60
gccactccag tcgttgttga tttgttggat catgtcactg gtgccacagt tttgggttta    120
tccccagaag attttcctga cggtatggca atcagtaacg aaaccgttac tttgactaca    180
catacaggta cccacatgga tgctccatta cattatggtc ctttgtctgg tggtgtacca    240
gcaaaatcaa tcgaccaagt cccattagaa tggtgttacg gtcctggtgt tagattggat    300
gttagacacg taccagctgg tgacggtatc actgtagacc atttgaatgc tgcattggat    360
gccgctgaac acgacttggc tcctggtgac attgttatgt tatggacagg tgctgatgca    420
ttgtggggta ctagagaata tttgtctaca tttccaggtt tgaccggtaa aggtactcaa    480
ttcttagttg aagcaggtgt caaggttatt ggtatagacg cctgggggttt ggatagacca    540
atggcagcca tgattgaaga atatagaaga accggtgaca aggtgcatt atggcctgcc    600
catgtttatg gtagaacaag agaatacttg caattggaaa agttgaacaa cttaggtgct    660
ttgccaggtg caactggtta cgacatatca tgctttcctg tagccgtcgc tggtacaggt    720
gccggttgga ccagagttgt agctgttttc gaacaagaag aagaagatta a             771

<210> SEQ ID NO 19
<211> LENGTH: 256
<212> TYPE: PRT
<213> ORGANISM: Artificial Sequence
<220> FEATURE:
<223> OTHER INFORMATION: Synthetic DNA

<400> SEQUENCE: 19

Met Ser Gly Arg Lys Thr Phe Leu Asp Leu Ser Phe Ala Thr Arg Asp
1               5                   10                  15
Thr Pro Ser Glu Ala Thr Pro Val Val Val Asp Leu Leu Asp His Val
                20                  25                  30
Thr Gly Ala Thr Val Leu Gly Leu Ser Pro Glu Asp Phe Pro Asp Gly
            35                  40                  45
Met Ala Ile Ser Asn Glu Thr Val Thr Leu Thr Thr His Thr Gly Thr
        50                  55                  60
His Met Asp Ala Pro Leu His Tyr Gly Pro Leu Ser Gly Gly Val Pro
```

```
                65                  70                  75                  80
Ala Lys Ser Ile Asp Gln Val Pro Leu Glu Trp Cys Tyr Gly Pro Gly
                    85                  90                  95

Val Arg Leu Asp Val Arg His Val Pro Ala Gly Asp Gly Ile Thr Val
                100                 105                 110

Asp His Leu Asn Ala Ala Leu Asp Ala Ala Glu His Asp Leu Ala Pro
                115                 120                 125

Gly Asp Ile Val Met Leu Trp Thr Gly Ala Asp Ala Leu Trp Gly Thr
130                 135                 140

Arg Glu Tyr Leu Ser Thr Phe Pro Gly Leu Thr Gly Lys Gly Thr Gln
145                 150                 155                 160

Phe Leu Val Glu Ala Gly Val Lys Val Ile Gly Ile Asp Ala Trp Gly
                165                 170                 175

Leu Asp Arg Pro Met Ala Ala Met Ile Glu Glu Tyr Arg Arg Thr Gly
                180                 185                 190

Asp Lys Gly Ala Leu Trp Pro Ala His Val Tyr Gly Arg Thr Arg Glu
                195                 200                 205

Tyr Leu Gln Leu Glu Lys Leu Asn Asn Leu Gly Ala Leu Pro Gly Ala
210                 215                 220

Thr Gly Tyr Asp Ile Ser Cys Phe Pro Val Ala Val Ala Gly Thr Gly
225                 230                 235                 240

Ala Gly Trp Thr Arg Val Val Ala Val Phe Glu Gln Glu Glu Glu Asp
                245                 250                 255
```

<210> SEQ ID NO 20
<211> LENGTH: 1212
<212> TYPE: DNA
<213> ORGANISM: Artificial Sequence
<220> FEATURE:
<223> OTHER INFORMATION: Synthetic DNA

<400> SEQUENCE: 20

```
atgagtagtt tatcaaatgc cagtcactta atggaagatg ttcaaggtat cagaaaagcc      60
caaagagccg acggtacagc cacagtcatg gctatcggta ccgcacatcc acctcacatt     120
tttccacaag atacatatgc tgactttac ttcagagcaa ccaattccga acataaggtt      180
gaattgaaaa agaaattcga tagaatctgt aagaaaacaa tgatcggcaa gagatacttc     240
aactacgacg aagaattctt aaagaaatac ccaaacatca cctccttcga tgaacctagt     300
ttgaacgata gacaagacat tgcgtccca ggtgtacctg cattaggtgc gaagctgca      360
gttaaggcca ttgctgaatg gggtagacca aaatctgaaa tacccactt ggttttctgt      420
acttcttgcg gtgtcgatat gccttcagca gacttccaat gtgccaagtt gttgggtttg     480
agaactaacg taaacaagta ctgtgtttac atgcaaggtt gctatgctgg tggtacagtt     540
atgagatacg ccaaagattt agctgaaaat aacagaggtg ccagagtctt ggttgtctgt     600
gctgaattga ctattatagg tttaagaggt ccaaatgaat cccatttgga taatgcaatc     660
ggtaacagtt atttggtga cggtgccgct gcattgattg taggttctga tccaatcatt     720
ggtgttgaaa agcctatgtt cgaaattgtc tgtgctaagc aaacagtaat cccaaactca     780
gaagacgtta tccatttgca catgagagaa gcaggtttaa tgttttacat gtctaaggat     840
tcacctgaaa ccatttcaaa taacgtcgaa gcttgcttgg tagacgtttt taaatctgtt     900
ggtatgactc cacctgaaga ttggaattca ttattctgga taccacatcc tggtggtaga     960
gcaatcttgg atcaagttga agccaagttg aaattaagac ctgaaaagtt cagagctact    1020
```

```
agaacagttt tatgggattg tggtaacatg gtttccgcat gcgtcttgta catattggat   1080
gaaatgagaa gaaagagtgc cgacgaaggt ttggaaacat acggtgaagg tttagaatgg   1140
ggtgttttgt taggttttgg tcctggtatg actgtagaaa ctatcttatt gcattccttg   1200
ccattgatgt ga                                                      1212

<210> SEQ ID NO 21
<211> LENGTH: 1212
<212> TYPE: DNA
<213> ORGANISM: Artificial Sequence
<220> FEATURE:
<223> OTHER INFORMATION: Synthetic DNA

<400> SEQUENCE: 21
atgggttcat tatcaaacta ttcacctgtt atggaagatg ttcaagcaat cagaaaggct     60
caaaaagcag atggtaccgc tactgttatg gctatcggta ctgcacatcc acctcacatt    120
tttccacaag atacttatgc cgactttac ttcagagcta caaactccga acataaggtt    180
gaattgaaaa agaaattcga tagaatctgt aagaaaacta tgatcggcaa gagatacttc    240
aactacgacg aagaattctt aaagaaatac ccaaacatca catccttcga tgaacctagt    300
ttgaacgata gacaagacat ctgcgtccca ggtgtacctg cattaggtgc cgaagctgca    360
gttaaggcca ttgctgaatg gggtagacca aaatctgaaa taacacactt ggttttctgt    420
acctcttgcg tgtcgatat gccttcagct gacttccaat gtgcaaagtt gttgggtttg    480
agaaccaacg taaacaagta ctgtgtttac atgcaaggtt gctatgcagg tggtactgta    540
atgagatacg ccaaggattt agctgaaaat aacagaggtg caagagtttt ggttgtctgt    600
gccgaattga ccattatagg tttaagaggt ccaaatgaat cccatttgga taatgctatc    660
ggtaacagtt tatttggtga cggtgccgct gcattgattg taggttctga tccaatcatt    720
ggtgttgaaa gacctatgtt cgaaattgtc tgtgcaaagc aaacagtaat cccaaactca    780
gaagacgtta tccatttgca catgagagaa gctggtttaa tgttttacat gtctaaggat    840
tcacctgaaa caatctcaaa aacgttgaa gcttgcttgg tagacgtttt taaatctgtc    900
ggtatgaccc cacctgaaga ttggaattca ttattctgga taccacatcc tggtggtaga    960
gctatcttgg atcaagtcga agcaagattg aagttaagac cagaaaaatt tggtgccact   1020
agaacagttt tatgggattg tggtaacatg gtttccgctt gcgtcttgta catattggat   1080
gaaatgagaa gaaagagtgt tgcagacggt ttggccacat acggtgaagg tttagaatgg   1140
ggtgtcttgt taggtttcgg tcctggtatg accgtagaaa ctattttgtt acactcttta   1200
ccacctgttt aa                                                      1212

<210> SEQ ID NO 22
<211> LENGTH: 1218
<212> TYPE: DNA
<213> ORGANISM: Artificial Sequence
<220> FEATURE:
<223> OTHER INFORMATION: Synthetic DNA

<400> SEQUENCE: 22
atgggtagta tcgccgaaag tagtccattg atgtccagag aaaacgtcga aggtataaga     60
aaggcacaaa gagccgaagg tacagccacc gttatggcaa taggtactgc ccatccacct    120
cacatctttc cacaagatac ttatgcagac ttttacttca gagccacaaa ctcagaacat    180
aaggttgaat aaaaagaa attcgataga atttgtaaga aaactatgat cggcaagaga    240
tacttcaact acgacgaaga attcttaaag aaatacccaa acatcacatc cttcgatgaa    300
```

```
cctagtttga atgatagaca agacatttgc gtaccaggtg ttcctgcctt gggcaaggaa    360
gctgcattaa aagctatcga agaatggggt caaccattgt ccaagattac acacttagta    420
ttttgtacct cttgcggtgt tgatatgcct tcagccgact tccaattggc taagttgttg    480
ggtttgaaca ccaacgttaa caagtactgt gtctacatgc aaggttgcta tgcaggtggt    540
actgttttga gatacgctaa agatttagca gaaaataaca gaggttctag agtcttggtt    600
gtctgtgccg aattgactat tataggttta agaggtccaa atgaatccca tttggataac    660
gctattggta acagtttgtt tggtgacggt gccgctgcat tgatagtcgg tgctgatcca    720
atcgtaggta ttgaaaagcc tatattcgaa atcgtttgtg caaaacaaac agtcatccca    780
gattctgaag acgttattca tttgcacttg agagaagcag gtttgatgtt ctacatgtct    840
aaggattcac ctgaaacaat ctcaaacaac gtagaaggtt gcttggttga catctttaaa    900
tctgttggta tgaccccacc tgctgattgg aattcattat tctggattcc acatcctggt    960
ggtagagcta tattggatga agttgaagca agattgaagt tgagaccaga aaagttcaga   1020
gcaaccagac acgttttatg ggaatatggt aacatggtct ccgcctgtgt attgtacata   1080
ttggatgaaa tgagaaacaa aagtgccgct gacggtttgg gtacatacgg tgaaggttta   1140
gaatggggtg tcttgttagg tttcggtcct ggtatgactg tagaaacaat attgttgcat   1200
tctttgccac ctgttttaa                                                1218

<210> SEQ ID NO 23
<211> LENGTH: 1180
<212> TYPE: DNA
<213> ORGANISM: Artificial Sequence
<220> FEATURE:
<223> OTHER INFORMATION: Synthetic DNA

<400> SEQUENCE: 23
gggttcctta gacaacggtt ccgccagaat caacaatcaa aagtccaacg gtttagcatc      60
aatcttagca atcggtacag ccttgccacc tatatgtatc aagcaagatg actacccaga    120
ttactacttc agagttacaa agtcagacca taagacccaa ttgaaggaaa agttcagaag    180
aatatgcgaa aaatccggtg ttacaaagag atacactgtc ttgacagaag atatgatcaa    240
ggaaaacgaa aacataatca cctacaaggc cccaagtttta gatgcaagac aagccatttt    300
gcataaagaa actcctaagt tagcaattga agctgcattg aaaacaatac aagaatgggg    360
tcaaccagtt tctaagatca cacacttatt tttctgttct tcatccggtg ttgctatttt    420
gcctagttct gatttccaaa tagctaaggc attgggttta gaaccaactg tccaaagatc    480
aatggtattc cctcacggtt gttacgccgc ttcatccggt ttgagattgg ctaaggatat    540
cgcagaaaac aacaaggacg ctagagtatt agttgtctgt tgcgaattga tggtttcttc    600
ttttcatgca ccatccgaag atgccattgg catgttaata ggtcacgcta tcttcggtga    660
tggtgcagcc tgtgccattg ttggtgctga cccaggtcct accgaaagac caatctttga    720
attagtcaaa ggtggtcaag taattgttcc tgatactgaa gactgcttgg gtggttgggt    780
tatggaaatg ggttggatct acgatttgaa taagagattg ccacaagcct tggctgacaa    840
catcttgggt gctttagatg acaccttgag attaactggc aagagagatg acttgaatgg    900
tttgttttat gttttgcatc ctggtggtag agcaatcatc gatttgttgg aagaaaagtt    960
ggaattgaca aaggataagt tagaatcatc cagaagagtc ttgtcaaatt acggtaacat   1020
gtggggtcct gctttagtat tcactttgga tgaaatgaga agaaagagta aggaagacaa   1080
```

```
cgcaactaca accggtggtg gttctgaatt gggtttaatg atggcttttg gtccaggttt    1140
gactaccgaa ataatggttt tgagaagtgt tcctttgtga                          1180

<210> SEQ ID NO 24
<211> LENGTH: 510
<212> TYPE: DNA
<213> ORGANISM: Artificial Sequence
<220> FEATURE:
<223> OTHER INFORMATION: Synthetic DNA

<400> SEQUENCE: 24
atgaggcatg tcgagcatac ggtaactgta gctgcacctg ctgatttggt gtgggaagtt      60
cttgctgatg tgctgggcta tgctgacatt ttccctccga ctgaaaaggt tgaaatcctt     120
gaagaaggac agggttatca agtagttaga ctccacgtag atgttgcagg tgagatcaat     180
acatggacgt ccagacgtga tttggatcct gcaagaagag tgatagctta taggcagtta     240
gaaacagctc caattgttgg gcatatgtct ggcgagtgga gcttttac acttgatgca       300 gaacggactc aacttgtttt aacacatgac ttcgtgacta gagcagcagg tgatgacggg     360
cttgttgccg gtaagcttac cccagatgag gccagagaaa tgctcgaggc cgtagtggag     420
aggaactcag ttgctgattt gaacgctgtc ttgggcgaag ccgagcgtcg ggttcgagca     480
gctgggggtg tcggaactgt cacggcatga                                     510

<210> SEQ ID NO 25
<211> LENGTH: 510
<212> TYPE: DNA
<213> ORGANISM: Artificial Sequence
<220> FEATURE:
<223> OTHER INFORMATION: Synthetic DNA

<400> SEQUENCE: 25
atgcgtcacg tcgaacacac cgtcaccgta gcggccccgg ccgacctggt ctgggaggtg      60
ctggccgatg tgctcggcta cgccgacatc ttccccgccga ccgagaaggt cgagatcctc    120
gaggagggtc agggctacca ggtcgtccgc ctgcacgtgg acgtcgccgg cgagatcaac     180
acctggacct cgcgccgcga cctggacccg gcccgccgcg tcatcgccta ccggcagttg     240
gagacggccc cgatcgtcgg gcacatgagc ggcgagtggc gcgccttcac gctggacgcc     300
gagcgcaccc aactggtgct cacccacgac ttcgtgacgc gcgcggccgg cgacgacggc     360
ctggtggccg gcaagctcac ccccgacgag gcgcgcgaga tgctggaggc ggtcgtcgag     420
cgcaacagcg tcgccgacct gaacgcggtg ctcggcgagg ccgagcgtcg ggtgcgcgcg     480
gccggcggcg tcgggacggt gaccgcgtga                                     510

<210> SEQ ID NO 26
<211> LENGTH: 771
<212> TYPE: DNA
<213> ORGANISM: Artificial Sequence
<220> FEATURE:
<223> OTHER INFORMATION: Synthetic DNA

<400> SEQUENCE: 26
atgtccggac gtaagacgtt tttggatttg tctttcgcaa ccagggatac accatcagaa      60
gctacacctg tggtggtcga ccttcttgat catgttactg gagcaaccgt tctaggtctc     120
tcaccagagg actttcctga tggcatggcc atttctaacg agaccgttac attaacgact     180
cacactggga ctcatatgga cgcacctcta cactatggtc ctctatcagg cggggtgcct     240
gctaagagta ttgatcaagt tcctcttgaa tggtgttatg gccctggagt gagacttgat     300
```

```
gtcaggcatg tgcccgcagg ggatggcata actgttgatc atttgaacgc cgctttggat      360
gctgcagagc acgatcttgc accaggcgat attgtgatgc tttggactgg ggcagatgct      420
ctgtggggta caagagaata tttatcaact tttcctggtc tcactggtaa ggggactcaa      480
tttcttgtgg aagcaggagt taaagtgatt ggaatagatg cttggggttt ggataggcca      540
atggcagcca tgatcgaaga atatcggagg actggtgata agggtgcact ctggccggca      600
catgtatacg gcagaacgcg agaatatcta caacttgaaa agcttaataa cctcggagct      660
ctcccgggcg caaccggtta cgatatatca tgttttccag tggccgttgc cggaactggc      720
gcaggctgga ctcgtgtagt cgcagttttt gaacaggagg aggaagattg a              771
```

<210> SEQ ID NO 27
<211> LENGTH: 771
<212> TYPE: DNA
<213> ORGANISM: Artificial Sequence
<220> FEATURE:
<223> OTHER INFORMATION: Synthetic DNA

<400> SEQUENCE: 27

```
gtgagcggcc gcaagacgtt cctcgacctg agcttcgcga cccgggacac ccccagcgag       60
gccaccccgg tcgtcgtcga cctgctcgac cacgtgaccg gcgcgacggt gctcgggctg      120
agccccgagg acttccccga cggcatggcc atctcgaacg agacggtcac cctcaccacg      180
cacaccggca cgcacatgga cgcgccgctg cactacggcc cgctcagcgg cggcgtgccg      240
gccaagtcga tcgaccaggt cccgctcgag tggtgctacg gcccgggcgt gcgcctggac      300
gtgcggcacg tgccggccgg cgacggcatc accgtcgacc acctcaacgc cgcgctcgac      360
gccgccgagc acgacctggc gcccggcgac atcgtcatgt tgtggaccgg cgcggacgcc      420
ctgtggggca cccgcgagta cctgtccacc ttccccggac tgaccggcaa gggaacgcag      480
ttcctggtcg aggcgggcgt gaaggtgatc ggcatcgacg cgtggggcct ggaccggccg      540
atggccgcga tgatcgagga gtaccggcgt accggcgaca agggcgcctt gtggccggcg      600
cacgtctacg gcgcaccccg cgaataccct cagttggaga agctcaacaa cctgggcgcg      660
ctgcccggcg ccaccggata cgacatcagt tgcttcccgg tcgccgtcgc gggcaccggt      720
gcgggctgga cccgggtggt cgccgtgttc gagcaggaag aggaggacta g              771
```

<210> SEQ ID NO 28
<211> LENGTH: 1578
<212> TYPE: DNA
<213> ORGANISM: Artificial Sequence
<220> FEATURE:
<223> OTHER INFORMATION: Synthetic DNA

<400> SEQUENCE: 28

```
atggaattca gattgttgat attggccttg ttctccgtat tgatgtctac ctctaatggt       60
gccgaaatct tggctttatt ccctattcat ggtatatcta actacaacgt agctgaagca      120 tgttgaaga ctttggctaa cagaggtcac aacgttaccg ttgtaacttc atttccacaa      180
aagaaaccag ttcctaattt gtacgaaatt gatgtatcag gtgcaaaggg tttagccaca      240
aactccatcc atttcgaaag attgcaaacc atcatccaag atgtcaagag taacttcaag      300
aacatggtta gattgtctag aacatactgt gaaatcatgt tctcagaccc aagagttttg      360
aacatcagag ataaaaagtt tgacttggtt ataaacgccg tattcggttc agattgcgac      420
gctggttttg catggaaaag tcaagctcct ttaatatcta tcttgaatgc cagacataca      480
```

```
ccatgggctt tgcacagaat gggtaatcct tccaacccag catatatgcc tgtaatccat    540
agtagattcc cagtcaagat gaatttcttt caaagaatga taaacaccgg ttggcactta    600
tacttttttgt acatgtactt ctactacggt aatggtgaag atgctaacaa aatggcaaga    660
aagtttttcg gtaatgatat gcctgacata aacgaaatgg ttttttaacac ctccttgttg   720
ttcgtaaaca ctcatttcag tgtcgatatg ccatacccctt tagtcccaaa ctgtatcgaa    780
atcggtggta tccatgttaa ggaaccacaa cctttgccat ggaaatcca aaagtttatg     840
gatgaagcag aacatggtgt aatctttttc accttgggta gtatggtcag aacttctaca    900
ttccctaatc aaactattca agcctttaaa gaagccttcg ctgaattacc acaaagagtt    960
ttgtggaagt tcgaaaacga aacgaagat atgccttcca acgttttgat cagaaagtgg    1020
ttcccacaaa acgacatctt cggtcataag aacatcaagg ctttcatttc acacggtggt   1080
aattccggtg ccttggaagc tgtccatttc ggtgttccta tcataggtat cccattgttt   1140
tatgatcaat acagaaacat cttgtctttc gttaaagaag gtgtagctgt cttgttggat   1200
gtaaacgact taactaagga taacatcttg tcttcagtta gaacagtcgt taacgacaag   1260
tcatactccg aaagaatgaa ggcattgtct caattgttta gagataggacc tatgtcacca   1320
ttagacacag ctgtttattg gaccgaatac gtaattagac atagaggtgc acatcactta   1380
aaaactgcag gtgccttttt gcactggtat caatacttgt tgttggatgt catcacattt   1440
ttgttggtta cattctgtgc attctgcttc atcgttaagt acatctgcaa ggccttaatc   1500
catcactact ggtccagttc taaatctgaa aagttgaaaa agaattctgc ttggtctcat   1560
ccacaattcg aaaaataa                                                1578

<210> SEQ ID NO 29
<211> LENGTH: 525
<212> TYPE: PRT
<213> ORGANISM: Artificial Sequence
<220> FEATURE:
<223> OTHER INFORMATION: Synthetic DNA

<400> SEQUENCE: 29

Met Glu Phe Arg Leu Leu Ile Leu Ala Leu Phe Ser Val Leu Met Ser
1               5                   10                  15

Thr Ser Asn Gly Ala Glu Ile Leu Ala Leu Phe Pro Ile His Gly Ile
            20                  25                  30

Ser Asn Tyr Asn Val Ala Glu Ala Leu Leu Lys Thr Leu Ala Asn Arg
        35                  40                  45

Gly His Asn Val Thr Val Thr Ser Phe Pro Gln Lys Lys Pro Val
    50                  55                  60

Pro Asn Leu Tyr Glu Ile Asp Val Ser Gly Ala Lys Gly Leu Ala Thr
65                  70                  75                  80

Asn Ser Ile His Phe Glu Arg Leu Gln Thr Ile Ile Gln Asp Val Lys
                85                  90                  95

Ser Asn Phe Lys Asn Met Val Arg Leu Ser Arg Thr Tyr Cys Glu Ile
            100                 105                 110

Met Phe Ser Asp Pro Arg Val Leu Asn Ile Arg Asp Lys Lys Phe Asp
        115                 120                 125

Leu Val Ile Asn Ala Val Phe Gly Ser Asp Cys Asp Ala Gly Phe Ala
    130                 135                 140

Trp Lys Ser Gln Ala Pro Leu Ile Ser Ile Leu Asn Ala Arg His Thr
145                 150                 155                 160

Pro Trp Ala Leu His Arg Met Gly Asn Pro Ser Asn Pro Ala Tyr Met
```

```
                165                 170                 175
        Pro Val Ile His Ser Arg Phe Pro Val Lys Met Asn Phe Gln Arg
                    180                 185                 190

Met Ile Asn Thr Gly Trp His Leu Tyr Phe Leu Tyr Met Tyr Phe Tyr
                    195                 200                 205

Tyr Gly Asn Gly Glu Asp Ala Asn Lys Met Ala Arg Lys Phe Phe Gly
                    210                 215                 220

Asn Asp Met Pro Asp Ile Asn Glu Met Val Phe Asn Thr Ser Leu Leu
        225                 230                 235                 240

Phe Val Asn Thr His Phe Ser Val Asp Met Pro Tyr Pro Leu Val Pro
                        245                 250                 255

Asn Cys Ile Glu Ile Gly Gly Ile His Val Lys Glu Pro Gln Pro Leu
                        260                 265                 270

Pro Leu Glu Ile Gln Lys Phe Met Asp Glu Ala Glu His Gly Val Ile
                        275                 280                 285

Phe Phe Thr Leu Gly Ser Met Val Arg Thr Ser Thr Phe Pro Asn Gln
                    290                 295                 300

Thr Ile Gln Ala Phe Lys Glu Ala Phe Ala Glu Leu Pro Gln Arg Val
        305                 310                 315                 320

Leu Trp Lys Phe Glu Asn Glu Asn Glu Asp Met Pro Ser Asn Val Leu
                        325                 330                 335

Ile Arg Lys Trp Phe Pro Gln Asn Asp Ile Phe Gly His Lys Asn Ile
                        340                 345                 350

Lys Ala Phe Ile Ser His Gly Gly Asn Ser Gly Ala Leu Glu Ala Val
                    355                 360                 365

His Phe Gly Val Pro Ile Ile Gly Ile Pro Leu Phe Tyr Asp Gln Tyr
                370                 375                 380

Arg Asn Ile Leu Ser Phe Val Lys Glu Gly Val Ala Val Leu Leu Asp
        385                 390                 395                 400

Val Asn Asp Leu Thr Lys Asp Asn Ile Leu Ser Ser Val Arg Thr Val
                        405                 410                 415

Val Asn Asp Lys Ser Tyr Ser Glu Arg Met Lys Ala Leu Ser Gln Leu
                    420                 425                 430

Phe Arg Asp Arg Pro Met Ser Pro Leu Asp Thr Ala Val Tyr Trp Thr
                    435                 440                 445

Glu Tyr Val Ile Arg His Arg Gly Ala His Leu Lys Thr Ala Gly
                450                 455                 460

Ala Phe Leu His Trp Tyr Gln Tyr Leu Leu Leu Asp Val Ile Thr Phe
                    465                 470                 475                 480

Leu Leu Val Thr Phe Cys Ala Phe Cys Phe Ile Val Lys Tyr Ile Cys
                        485                 490                 495

Lys Ala Leu Ile His His Tyr Trp Ser Ser Ser Lys Ser Glu Lys Leu
                        500                 505                 510

Lys Lys Asn Ser Ala Trp Ser His Pro Gln Phe Glu Lys
                    515                 520                 525

<210> SEQ ID NO 30
<211> LENGTH: 1437
<212> TYPE: DNA
<213> ORGANISM: Artificial Sequence
<220> FEATURE:
<223> OTHER INFORMATION: Synthetic DNA

<400> SEQUENCE: 30
atggaattca gattgttgat attggccttg ttctccgtat tgatgtctac ctctaatggt    60
```

```
gccgaaatct tggctttatt ccctattcat ggtatatcta actacaacgt agctgaagca    120
ttgttgaaga ctttggctaa cagaggtcac aacgttaccg ttgtaacttc atttccacaa    180
aagaaaccag ttcctaattt gtacgaaatt gatgtatcag gtgcaagggg tttagccaca    240
aactccatcc atttcgaaag attgcaaacc atcatccaag atgtcaagag taacttcaag    300
aacatggtta gattgtctag aacatactgt gaaatcatgt tctcagaccc aagagttttg    360
aacatcagag ataaaaagtt tgacttggtt ataaacgccg tattcggttc agattgcgac    420
gctggttttg catggaaaag tcaagctcct ttaatatcta tcttgaatgc agacatacca    480
ccatgggctt gcacagaatg ggtaatcctt ccaacccag catatatgcc tgtaatccat    540
agtagattcc cagtcaagat gaatttcttt caaagaatga taaacaccgg ttggcactta    600
tactttttgt acatgtactt ctactacggt aatggtgaag atgctaacaa atggcaaga    660 aagttttccg gtaatgatat gcctgacata aacgaaatgg ttttttaacac ctccttgttg    720 ttcgtaaaca ctcatttcag tgtcgatatg ccatacccttt agtcccaaa ctgtatcgaa    780 atcggtggta tccatgttaa ggaaccacaa cctttgccat ggaaatcca aagtttatg    840 gatgaagcag aacatggtgt aatcttttc accttgggta gtatggtcag aacttctaca    900
ttccctaatc aaactattca agcctttaaa gaagccttcg ctgaattacc acaaagagtt    960
ttgtggaagt tcgaaaacga aaacgaagat atgccttcca acgttttgat cagaaagtgg   1020
ttcccacaaa acgacatctt cggtcataag aacatcaagg ctttcatttc acacggtggt   1080
aattccggtg ccttggaagc tgtccatttc ggtgttccta tcataggtat cccattgttt   1140
tatgatcaat acagaaacat cttgtctttc gttaagaag gtgtagctgt cttgttggat   1200
gtaaacgact taactaagga taacatcttg tcttcagtta aacagtcgt taacgacaag   1260 tcatactccg aaagaatgaa ggcattgtct caattgttta gagatagacc tatgtcacca   1320
ttagacacag ctgtttattg gaccgaatac gtaattagac atagaggtgc acatcactta   1380
aaaactgcag gtgcctttttt gcactctgct tggtctcatc cacaattcga aaaataa     1437

<210> SEQ ID NO 31
<211> LENGTH: 478
<212> TYPE: PRT
<213> ORGANISM: Artificial Sequence
<220> FEATURE:
<223> OTHER INFORMATION: Synthetic DNA

<400> SEQUENCE: 31

Met Glu Phe Arg Leu Leu Ile Leu Ala Leu Phe Ser Val Leu Met Ser
1               5                   10                  15

Thr Ser Asn Gly Ala Glu Ile Leu Ala Leu Phe Pro Ile His Gly Ile
            20                  25                  30

Ser Asn Tyr Asn Val Ala Glu Ala Leu Leu Lys Thr Leu Ala Asn Arg
        35                  40                  45

Gly His Asn Val Thr Val Thr Ser Phe Pro Gln Lys Lys Pro Val
    50                  55                  60

Pro Asn Leu Tyr Glu Ile Asp Val Ser Gly Ala Lys Gly Leu Ala Thr
65                  70                  75                  80

Asn Ser Ile His Phe Glu Arg Leu Gln Thr Ile Gln Asp Val Lys
                85                  90                  95

Ser Asn Phe Lys Asn Met Val Arg Leu Ser Arg Thr Tyr Cys Glu Ile
            100                 105                 110

Met Phe Ser Asp Pro Arg Val Leu Asn Ile Arg Asp Lys Lys Phe Asp
```

```
            115                 120                 125
Leu Val Ile Asn Ala Val Phe Gly Ser Asp Cys Asp Ala Gly Phe Ala
    130                 135                 140
Trp Lys Ser Gln Ala Pro Leu Ile Ser Ile Leu Asn Ala Arg His Thr
145                 150                 155                 160
Pro Trp Ala Leu His Arg Met Gly Asn Pro Ser Asn Pro Ala Tyr Met
                165                 170                 175
Pro Val Ile His Ser Arg Phe Pro Val Lys Met Asn Phe Phe Gln Arg
                180                 185                 190
Met Ile Asn Thr Gly Trp His Leu Tyr Phe Leu Tyr Met Tyr Phe Tyr
                195                 200                 205
Tyr Gly Asn Gly Glu Asp Ala Asn Lys Met Ala Arg Lys Phe Phe Gly
    210                 215                 220
Asn Asp Met Pro Asp Ile Asn Glu Met Val Phe Asn Thr Ser Leu Leu
225                 230                 235                 240
Phe Val Asn Thr His Phe Ser Val Asp Met Pro Tyr Pro Leu Val Pro
                245                 250                 255
Asn Cys Ile Glu Ile Gly Gly Ile His Val Lys Glu Pro Gln Pro Leu
                260                 265                 270
Pro Leu Glu Ile Gln Lys Phe Met Asp Glu Ala Glu His Gly Val Ile
                275                 280                 285
Phe Phe Thr Leu Gly Ser Met Val Arg Thr Ser Thr Phe Pro Asn Gln
    290                 295                 300
Thr Ile Gln Ala Phe Lys Glu Ala Phe Ala Glu Leu Pro Gln Arg Val
305                 310                 315                 320
Leu Trp Lys Phe Glu Asn Glu Asn Glu Asp Met Pro Ser Asn Val Leu
                325                 330                 335
Ile Arg Lys Trp Phe Pro Gln Asn Asp Ile Phe Gly His Lys Asn Ile
                340                 345                 350
Lys Ala Phe Ile Ser His Gly Gly Asn Ser Gly Ala Leu Glu Ala Val
                355                 360                 365
His Phe Gly Val Pro Ile Ile Gly Ile Pro Leu Phe Tyr Asp Gln Tyr
    370                 375                 380
Arg Asn Ile Leu Ser Phe Val Lys Glu Gly Val Ala Val Leu Leu Asp
385                 390                 395                 400
Val Asn Asp Leu Thr Lys Asp Asn Ile Leu Ser Ser Val Arg Thr Val
                405                 410                 415
Val Asn Asp Lys Ser Tyr Ser Glu Arg Met Lys Ala Leu Ser Gln Leu
                420                 425                 430
Phe Arg Asp Arg Pro Met Ser Pro Leu Asp Thr Ala Val Tyr Trp Thr
                435                 440                 445
Glu Tyr Val Ile Arg His Arg Gly Ala His Leu Lys Thr Ala Gly
    450                 455                 460
Ala Phe Leu His Ser Ala Trp Ser His Pro Gln Phe Glu Lys
465                 470                 475

<210> SEQ ID NO 32
<211> LENGTH: 1380
<212> TYPE: DNA
<213> ORGANISM: Artificial Sequence
<220> FEATURE:
<223> OTHER INFORMATION: Synthetic DNA

<400> SEQUENCE: 32
atggccgaaa tcttggcttt attccctatt catggtatat ctaactacaa cgtagctgaa        60
```

-continued

```
gcattgttga agactttggc taacagaggt cacaacgtta ccgttgtaac ttcatttcca      120
caaaagaaac cagttcctaa tttgtacgaa attgatgtat caggtgcaaa gggtttagcc      180
acaaactcca tccatttcga aagattgcaa accatcatcc aagatgtcaa gagtaacttc      240
aagaacatgg ttagattgtc tagaacatac tgtgaaatca tgttctcaga cccaagagtt      300
ttgaacatca gagataaaaa gtttgacttg gttataaacg ccgtattcgg ttcagattgc      360
gacgctggtt ttgcatggaa aagtcaagct cctttaatat ctatcttgaa tgccagacat      420
acaccatggg ctttgcacag aatgggtaat ccttccaacc cagcatatat gcctgtaatc      480
catagtagat tcccagtcaa gatgaatttc tttcaaagaa tgataaacac cggttggcac      540
ttatactttt tgtacatgta cttctactac ggtaatggtg aagatgctaa caaaatggca      600
agaaagtttt tcggtaatga tatgcctgac ataaacgaaa tggtttttaa cacctccttg      660
ttgttcgtaa acactcattt cagtgtcgat atgccatacc ctttagtccc aaactgtatc      720
gaaatcggtg gtatccatgt taaggaacca caacctttgc cattggaaat ccaaaagttt      780
atggatgaag cagaacatgg tgtaatcttt ttcaccttgg gtagtatggt cagaacttct      840
acattcccta atcaaactat tcaagccttt aaagaagcct tcgctgaatt accacaaaga      900
gttttgtgga agttcgaaaa cgaaaacgaa gatatgcctt ccaacgtttt gatcagaaag      960
tggttcccac aaaacgacat cttcggtcat aagaacatca aggctttcat ttcacacggt     1020
ggtaattccg gtgccttgga agctgtccat ttcggtgttc ctatcatagg tatcccattg     1080
ttttatgatc aatacagaaa catcttgtct ttcgttaaag aaggtgtagc tgtcttgttg     1140
gatgtaaacg acttaactaa ggataacatc ttgtcttcag ttagaacagt cgttaacgac     1200
aagtcatact ccgaaagaat gaaggcattg tctcaattgt ttagagatag acctatgtca     1260
ccattagaca cagctgtttta ttggaccgaa tacgtaatta gacatagagg tgcacatcac     1320
ttaaaaactg caggtgcctt tttgcactct gcttggtctc atccacaatt cgaaaaataa     1380
```

<210> SEQ ID NO 33
<211> LENGTH: 459
<212> TYPE: PRT
<213> ORGANISM: Artificial Sequence
<220> FEATURE:
<223> OTHER INFORMATION: Synthetic DNA

<400> SEQUENCE: 33

```
Met Ala Glu Ile Leu Ala Leu Phe Pro Ile His Gly Ile Ser Asn Tyr
1               5                   10                  15

Asn Val Ala Glu Ala Leu Leu Lys Thr Leu Ala Asn Arg Gly His Asn
            20                  25                  30

Val Thr Val Thr Ser Phe Pro Gln Lys Lys Pro Val Pro Asn Leu
        35                  40                  45

Tyr Glu Ile Asp Val Ser Gly Ala Lys Gly Leu Ala Thr Asn Ser Ile
    50                  55                  60

His Phe Glu Arg Leu Gln Thr Ile Ile Gln Asp Val Lys Ser Asn Phe
65                  70                  75                  80

Lys Asn Met Val Arg Leu Ser Arg Thr Tyr Cys Glu Ile Met Phe Ser
                85                  90                  95

Asp Pro Arg Val Leu Asn Ile Arg Asp Lys Lys Phe Asp Leu Val Ile
            100                 105                 110

Asn Ala Val Phe Gly Ser Asp Cys Asp Ala Gly Phe Ala Trp Lys Ser
        115                 120                 125
```

Gln Ala Pro Leu Ile Ser Ile Leu Asn Ala Arg His Thr Pro Trp Ala
130                 135                 140

Leu His Arg Met Gly Asn Pro Ser Asn Pro Ala Tyr Met Pro Val Ile
145                 150                 155                 160

His Ser Arg Phe Pro Val Lys Met Asn Phe Phe Gln Arg Met Ile Asn
                165                 170                 175

Thr Gly Trp His Leu Tyr Phe Leu Tyr Met Tyr Phe Tyr Tyr Gly Asn
                180                 185                 190

Gly Glu Asp Ala Asn Lys Met Ala Arg Lys Phe Phe Gly Asn Asp Met
                195                 200                 205

Pro Asp Ile Asn Glu Met Val Phe Asn Thr Ser Leu Leu Phe Val Asn
210                 215                 220

Thr His Phe Ser Val Asp Met Pro Tyr Pro Leu Val Pro Asn Cys Ile
225                 230                 235                 240

Glu Ile Gly Gly Ile His Val Lys Glu Pro Gln Pro Leu Pro Leu Glu
                245                 250                 255

Ile Gln Lys Phe Met Asp Glu Ala Glu His Gly Val Ile Phe Phe Thr
                260                 265                 270

Leu Gly Ser Met Val Arg Thr Ser Thr Phe Pro Asn Gln Thr Ile Gln
                275                 280                 285

Ala Phe Lys Glu Ala Phe Ala Glu Leu Pro Gln Arg Val Leu Trp Lys
290                 295                 300

Phe Glu Asn Glu Asn Glu Asp Met Pro Ser Asn Val Leu Ile Arg Lys
305                 310                 315                 320

Trp Phe Pro Gln Asn Asp Ile Phe Gly His Lys Asn Ile Lys Ala Phe
                325                 330                 335

Ile Ser His Gly Gly Asn Ser Gly Ala Leu Glu Ala Val His Phe Gly
                340                 345                 350

Val Pro Ile Ile Gly Ile Pro Leu Phe Tyr Asp Gln Tyr Arg Asn Ile
                355                 360                 365

Leu Ser Phe Val Lys Glu Gly Val Ala Val Leu Leu Asp Val Asn Asp
                370                 375                 380

Leu Thr Lys Asp Asn Ile Leu Ser Ser Val Arg Thr Val Val Asn Asp
385                 390                 395                 400

Lys Ser Tyr Ser Glu Arg Met Lys Ala Leu Ser Gln Leu Phe Arg Asp
                405                 410                 415

Arg Pro Met Ser Pro Leu Asp Thr Ala Val Tyr Trp Thr Glu Tyr Val
                420                 425                 430

Ile Arg His Arg Gly Ala His His Leu Lys Thr Ala Gly Ala Phe Leu
                435                 440                 445

His Ser Ala Trp Ser His Pro Gln Phe Glu Lys
450                 455

<210> SEQ ID NO 34
<211> LENGTH: 19
<212> TYPE: DNA
<213> ORGANISM: Artificial Sequence
<220> FEATURE:
<223> OTHER INFORMATION: Synthetic DNA

<400> SEQUENCE: 34
ggaagaaggt cgcatacca                                              19

<210> SEQ ID NO 35
<211> LENGTH: 42
<212> TYPE: DNA

<210> SEQ ID NO 35
<211> LENGTH: 42
<212> TYPE: DNA
<213> ORGANISM: Artificial Sequence
<220> FEATURE:
<223> OTHER INFORMATION: Synthetic DNA

<400> SEQUENCE: 35
gatccccggg aattgccatg gatcaggaga aggagagtca ag            42

<210> SEQ ID NO 36
<211> LENGTH: 39
<212> TYPE: DNA
<213> ORGANISM: Artificial Sequence
<220> FEATURE:
<223> OTHER INFORMATION: Synthetic DNA

<400> SEQUENCE: 36
aattccagct gaccaccatg ggcgaaaagg caaaggagc               39

<210> SEQ ID NO 37
<211> LENGTH: 20
<212> TYPE: DNA
<213> ORGANISM: Artificial Sequence
<220> FEATURE:
<223> OTHER INFORMATION: Synthetic DNA

<400> SEQUENCE: 37
gctagaaaag gcaagggagg                                    20

<210> SEQ ID NO 38
<211> LENGTH: 43
<212> TYPE: DNA
<213> ORGANISM: Artificial Sequence
<220> FEATURE:
<223> OTHER INFORMATION: Synthetic DNA

<400> SEQUENCE: 38
catggcaatt cccggggatc gccggcaatt cttttaggt agc           43

<210> SEQ ID NO 39
<211> LENGTH: 18
<212> TYPE: DNA
<213> ORGANISM: Artificial Sequence
<220> FEATURE:
<223> OTHER INFORMATION: Synthetic DNA

<400> SEQUENCE: 39
ccagaagcag tacacggc                                      18

<210> SEQ ID NO 40
<211> LENGTH: 21
<212> TYPE: DNA
<213> ORGANISM: Artificial Sequence
<220> FEATURE:
<223> OTHER INFORMATION: Synthetic DNA

<400> SEQUENCE: 40
gttgtctgct tgcgcttctt c                                  21

<210> SEQ ID NO 41
<211> LENGTH: 41
<212> TYPE: DNA
<213> ORGANISM: Artificial Sequence
<220> FEATURE:
<223> OTHER INFORMATION: Synthetic DNA

<400> SEQUENCE: 41
catggtggtc agctggaatt cctccgccat ttcttattcc c            41

<210> SEQ ID NO 42
<211> LENGTH: 22
<212> TYPE: DNA
<213> ORGANISM: Artificial Sequence
<220> FEATURE:
<223> OTHER INFORMATION: Synthetic DNA

<400> SEQUENCE: 42
gtgggttgaa ccgcttactc ag                                              22

<210> SEQ ID NO 43
<211> LENGTH: 42
<212> TYPE: DNA
<213> ORGANISM: Artificial Sequence
<220> FEATURE:
<223> OTHER INFORMATION: Synthetic DNA

<400> SEQUENCE: 43
gatccccggg aattgccatg cccggaggaa tcaaaatgac gc                        42

<210> SEQ ID NO 44
<211> LENGTH: 43
<212> TYPE: DNA
<213> ORGANISM: Artificial Sequence
<220> FEATURE:
<223> OTHER INFORMATION: Synthetic DNA

<400> SEQUENCE: 44
aattccagct gaccaccatg gtttgggatt cttaggtgag ctc                       43

<210> SEQ ID NO 45
<211> LENGTH: 22
<212> TYPE: DNA
<213> ORGANISM: Artificial Sequence
<220> FEATURE:
<223> OTHER INFORMATION: Synthetic DNA

<400> SEQUENCE: 45
cctccctggc gtatacacaa ac                                              22

<210> SEQ ID NO 46
<211> LENGTH: 17
<212> TYPE: DNA
<213> ORGANISM: Artificial Sequence
<220> FEATURE:
<223> OTHER INFORMATION: Synthetic DNA

<400> SEQUENCE: 46
gctcgagctt gccagcc                                                    17

<210> SEQ ID NO 47
<211> LENGTH: 39
<212> TYPE: DNA
<213> ORGANISM: Artificial Sequence
<220> FEATURE:
<223> OTHER INFORMATION: Synthetic DNA

<400> SEQUENCE: 47
gatccccggg aattgccatg gctggtgttg ggacacacg                            39

<210> SEQ ID NO 48
<211> LENGTH: 45
<212> TYPE: DNA
<213> ORGANISM: Artificial Sequence
<220> FEATURE:

<223> OTHER INFORMATION: Synthetic DNA

<400> SEQUENCE: 48
aattccagct gaccaccatg gcttggaaat cagtatagct ttctg    45

<210> SEQ ID NO 49
<211> LENGTH: 21
<212> TYPE: DNA
<213> ORGANISM: Artificial Sequence
<220> FEATURE:
<223> OTHER INFORMATION: Synthetic DNA

<400> SEQUENCE: 49
gcttgtggtc tgtctgaatc g    21

<210> SEQ ID NO 50
<211> LENGTH: 27
<212> TYPE: DNA
<213> ORGANISM: Artificial Sequence
<220> FEATURE:
<223> OTHER INFORMATION: Synthetic DNA

<400> SEQUENCE: 50
gggtttaatg aggagcagag gatgcgg    27

<210> SEQ ID NO 51
<211> LENGTH: 27
<212> TYPE: DNA
<213> ORGANISM: Artificial Sequence
<220> FEATURE:
<223> OTHER INFORMATION: Synthetic DNA

<400> SEQUENCE: 51
ggacttaatg tagtggtggt gctggtg    27

<210> SEQ ID NO 52
<211> LENGTH: 30
<212> TYPE: DNA
<213> ORGANISM: Artificial Sequence
<220> FEATURE:
<223> OTHER INFORMATION: Synthetic DNA

<400> SEQUENCE: 52
ggcattaatc gcgtggaatt tggaagagag    30

<210> SEQ ID NO 53
<211> LENGTH: 28
<212> TYPE: DNA
<213> ORGANISM: Artificial Sequence
<220> FEATURE:
<223> OTHER INFORMATION: Synthetic DNA

<400> SEQUENCE: 53
ggtcttaatg tgctcgggga cgtgaaag    28

<210> SEQ ID NO 54
<211> LENGTH: 29
<212> TYPE: DNA
<213> ORGANISM: Artificial Sequence
<220> FEATURE:
<223> OTHER INFORMATION: Synthetic DNA

<400> SEQUENCE: 54
gggtttaatg gtcgtctgtc aaggagttg    29

<210> SEQ ID NO 55
<211> LENGTH: 31
<212> TYPE: DNA
<213> ORGANISM: Artificial Sequence
<220> FEATURE:
<223> OTHER INFORMATION: Synthetic DNA

<400> SEQUENCE: 55
ggacttaatg cagtgctgta tatgggtctt g                           31

<210> SEQ ID NO 56
<211> LENGTH: 33
<212> TYPE: DNA
<213> ORGANISM: Artificial Sequence
<220> FEATURE:
<223> OTHER INFORMATION: Synthetic DNA

<400> SEQUENCE: 56
ggcattaatg agtttgtgag atgttcagga tgg                         33

<210> SEQ ID NO 57
<211> LENGTH: 27
<212> TYPE: DNA
<213> ORGANISM: Artificial Sequence
<220> FEATURE:
<223> OTHER INFORMATION: Synthetic DNA

<400> SEQUENCE: 57
ggtcttaatg aggtgaagga cacagcg                                27

<210> SEQ ID NO 58
<211> LENGTH: 31
<212> TYPE: DNA
<213> ORGANISM: Artificial Sequence
<220> FEATURE:
<223> OTHER INFORMATION: Synthetic DNA

<400> SEQUENCE: 58
gggtttaatc gcagagacta ggacacaagt g                           31

<210> SEQ ID NO 59
<211> LENGTH: 28
<212> TYPE: DNA
<213> ORGANISM: Artificial Sequence
<220> FEATURE:
<223> OTHER INFORMATION: Synthetic DNA

<400> SEQUENCE: 59
ggacttaatg cggcgatctg tggtagag                               28

<210> SEQ ID NO 60
<211> LENGTH: 31
<212> TYPE: DNA
<213> ORGANISM: Artificial Sequence
<220> FEATURE:
<223> OTHER INFORMATION: Synthetic DNA

<400> SEQUENCE: 60
ggcattaatg ccagcatatt caaacccagt c                           31

<210> SEQ ID NO 61
<211> LENGTH: 29
<212> TYPE: DNA
<213> ORGANISM: Artificial Sequence
<220> FEATURE:
<223> OTHER INFORMATION: Synthetic DNA

```
<400> SEQUENCE: 61
ggtcttaatc acacaaccaa cctccgatc                                    29

<210> SEQ ID NO 62
<211> LENGTH: 31
<212> TYPE: DNA
<213> ORGANISM: Artificial Sequence
<220> FEATURE:
<223> OTHER INFORMATION: Synthetic DNA

<400> SEQUENCE: 62
agagcgatat gggttcctta gacaacggtt c                                 31

<210> SEQ ID NO 63
<211> LENGTH: 33
<212> TYPE: DNA
<213> ORGANISM: Artificial Sequence
<220> FEATURE:
<223> OTHER INFORMATION: Synthetic DNA

<400> SEQUENCE: 63
tctgcgattc acaaaggaac acttctcaaa acc                               33

<210> SEQ ID NO 64
<211> LENGTH: 32
<212> TYPE: DNA
<213> ORGANISM: Artificial Sequence
<220> FEATURE:
<223> OTHER INFORMATION: Synthetic DNA

<400> SEQUENCE: 64
agagcgatat gagttcactc tccaacgctt cc                                32

<210> SEQ ID NO 65
<211> LENGTH: 29
<212> TYPE: DNA
<213> ORGANISM: Artificial Sequence
<220> FEATURE:
<223> OTHER INFORMATION: Synthetic DNA

<400> SEQUENCE: 65
tctgcgattc acatgagagg caggctgtg                                    29

<210> SEQ ID NO 66
<211> LENGTH: 28
<212> TYPE: DNA
<213> ORGANISM: Artificial Sequence
<220> FEATURE:
<223> OTHER INFORMATION: Synthetic DNA

<400> SEQUENCE: 66
agagcgatgg gttcccttga caatggtt                                     28

<210> SEQ ID NO 67
<211> LENGTH: 32
<212> TYPE: DNA
<213> ORGANISM: Artificial Sequence
<220> FEATURE:
<223> OTHER INFORMATION: Synthetic DNA

<400> SEQUENCE: 67
tctgcgattt agagaggcac acttcggaga ac                                32

<210> SEQ ID NO 68
<211> LENGTH: 33
```

<212> TYPE: DNA
<213> ORGANISM: Artificial Sequence
<220> FEATURE:
<223> OTHER INFORMATION: Synthetic DNA

<400> SEQUENCE: 68
agagcgatat gagtagttta tcaaatgcca gtc					33

<210> SEQ ID NO 69
<211> LENGTH: 27
<212> TYPE: DNA
<213> ORGANISM: Artificial Sequence
<220> FEATURE:
<223> OTHER INFORMATION: Synthetic DNA

<400> SEQUENCE: 69
tctgcgattc acatcaatgg caaggaa						27

<210> SEQ ID NO 70
<211> LENGTH: 32
<212> TYPE: DNA
<213> ORGANISM: Artificial Sequence
<220> FEATURE:
<223> OTHER INFORMATION: Synthetic DNA

<400> SEQUENCE: 70
agatatacca tgcgtcatgt tgaacatacc gt					32

<210> SEQ ID NO 71
<211> LENGTH: 34
<212> TYPE: DNA
<213> ORGANISM: Artificial Sequence
<220> FEATURE:
<223> OTHER INFORMATION: Synthetic DNA

<400> SEQUENCE: 71
atggctgctt tatgcggtaa ctgtaccaac acca					34

<210> SEQ ID NO 72
<211> LENGTH: 29
<212> TYPE: DNA
<213> ORGANISM: Artificial Sequence
<220> FEATURE:
<223> OTHER INFORMATION: Synthetic DNA

<400> SEQUENCE: 72
atatacatat gagcggtcgt aaaacctttt					29

<210> SEQ ID NO 73
<211> LENGTH: 31
<212> TYPE: DNA
<213> ORGANISM: Artificial Sequence
<220> FEATURE:
<223> OTHER INFORMATION: Synthetic DNA

<400> SEQUENCE: 73
atatccaatt ttaatcctct tcttcttgtt c					31

<210> SEQ ID NO 74
<211> LENGTH: 25
<212> TYPE: DNA
<213> ORGANISM: Artificial Sequence
<220> FEATURE:
<223> OTHER INFORMATION: Synthetic DNA

<400> SEQUENCE: 74

```
agagcgatga gacacgttga acaca                                           25
```

<210> SEQ ID NO 75
<211> LENGTH: 27
<212> TYPE: DNA
<213> ORGANISM: Artificial Sequence
<220> FEATURE:
<223> OTHER INFORMATION: Synthetic DNA

<400> SEQUENCE: 75

```
tctgcgattt atgcagttac ggtacca                                         27
```

<210> SEQ ID NO 76
<211> LENGTH: 26
<212> TYPE: DNA
<213> ORGANISM: Artificial Sequence
<220> FEATURE:
<223> OTHER INFORMATION: Synthetic DNA

<400> SEQUENCE: 76

```
agagcgatgt ccggtagaaa gacctt                                          26
```

<210> SEQ ID NO 77
<211> LENGTH: 30
<212> TYPE: DNA
<213> ORGANISM: Artificial Sequence
<220> FEATURE:
<223> OTHER INFORMATION: Synthetic DNA

<400> SEQUENCE: 77

```
tctgcgattt aatcttcttc ttcttgttcg                                      30
```

<210> SEQ ID NO 78
<211> LENGTH: 31
<212> TYPE: DNA
<213> ORGANISM: Artificial Sequence
<220> FEATURE:
<223> OTHER INFORMATION: Synthetic DNA

<400> SEQUENCE: 78

```
agagcgatat ggagtttcgc ttgcttatcc t                                    31
```

<210> SEQ ID NO 79
<211> LENGTH: 37
<212> TYPE: DNA
<213> ORGANISM: Artificial Sequence
<220> FEATURE:
<223> OTHER INFORMATION: Synthetic DNA

<400> SEQUENCE: 79

```
tctgcgattt aattcttctt caactttcc gacttag                               37
```

<210> SEQ ID NO 80
<211> LENGTH: 36
<212> TYPE: DNA
<213> ORGANISM: Artificial Sequence
<220> FEATURE:
<223> OTHER INFORMATION: Synthetic DNA

<400> SEQUENCE: 80

```
ggcttaatat gagttcactc tccaacgctt cccatc                               36
```

<210> SEQ ID NO 81
<211> LENGTH: 41
<212> TYPE: DNA
<213> ORGANISM: Artificial Sequence
<220> FEATURE:
<223> OTHER INFORMATION: Synthetic DNA

<400> SEQUENCE: 81
ggtttaattt acatgagagg caggctgtgg agaaggatag t          41

<210> SEQ ID NO 82
<211> LENGTH: 26
<212> TYPE: DNA
<213> ORGANISM: Artificial Sequence
<220> FEATURE:
<223> OTHER INFORMATION: Synthetic DNA

<400> SEQUENCE: 82
ggcttaatat gaggcatgtc gagcat          26

<210> SEQ ID NO 83
<211> LENGTH: 31
<212> TYPE: DNA
<213> ORGANISM: Artificial Sequence
<220> FEATURE:
<223> OTHER INFORMATION: Synthetic DNA

<400> SEQUENCE: 83
ggtttaattt atgccgtgac agttccgaca c          31

<210> SEQ ID NO 84
<211> LENGTH: 26
<212> TYPE: DNA
<213> ORGANISM: Artificial Sequence
<220> FEATURE:
<223> OTHER INFORMATION: Synthetic DNA

<400> SEQUENCE: 84
ggcttaatat gtccggacgt aagacg          26

<210> SEQ ID NO 85
<211> LENGTH: 31
<212> TYPE: DNA
<213> ORGANISM: Artificial Sequence
<220> FEATURE:
<223> OTHER INFORMATION: Synthetic DNA

<400> SEQUENCE: 85
ggtttaattt aatcttcctc ctcctgttca a          31

<210> SEQ ID NO 86
<211> LENGTH: 36
<212> TYPE: DNA
<213> ORGANISM: Artificial Sequence
<220> FEATURE:
<223> OTHER INFORMATION: Synthetic DNA

<400> SEQUENCE: 86
ggcttaatat ggaattcaga ttgttgatat tggcct          36

<210> SEQ ID NO 87
<211> LENGTH: 41
<212> TYPE: DNA
<213> ORGANISM: Artificial Sequence
<220> FEATURE:
<223> OTHER INFORMATION: Synthetic DNA

<400> SEQUENCE: 87
ggtttaattt attttttcgaa ttgtggatga gaccaagcag a          41

<210> SEQ ID NO 88
<211> LENGTH: 29
<212> TYPE: DNA
<213> ORGANISM: Artificial Sequence
<220> FEATURE:
<223> OTHER INFORMATION: Synthetic DNA

<400> SEQUENCE: 88
ggggacaagt ttgtacaaaa aagcaggct                              29

<210> SEQ ID NO 89
<211> LENGTH: 54
<212> TYPE: DNA
<213> ORGANISM: Artificial Sequence
<220> FEATURE:
<223> OTHER INFORMATION: Synthetic DNA

<400> SEQUENCE: 89
ttatttttcg aattgtggat gagaccaagc agagtgcaaa aaggcacctg cagt    54

<210> SEQ ID NO 90
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 90
gggtttaaug aggagcagag gatgcgg                                27

<210> SEQ ID NO 91
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 91
ggacttaaug tagtggtggt gctggtg                                27

<210> SEQ ID NO 92
<211> LENGTH: 30
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 92
ggcattaauc gcgtggaatt tggaagagag                              30

<210> SEQ ID NO 93
<211> LENGTH: 28
<212> TYPE: DNA
<213> ORGANISM: Artificial Sequence
<220> FEATURE:
<223> OTHER INFORMATION: Synthetic DNA

```
<220> FEATURE:
<221> NAME/KEY: misc_feature
<222> LOCATION: (9)..(9)
<223> OTHER INFORMATION: u is deoxy

<400> SEQUENCE: 93
ggtcttaaug tgctcgggga cgtgaaag                                      28

<210> SEQ ID NO 94
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 94
gggtttaaug gtcgtctgtc aaggagttg                                     29

<210> SEQ ID NO 95
<211> LENGTH: 31
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 95
ggacttaaug cagtgctgta tatgggtctt g                                  31

<210> SEQ ID NO 96
<211> LENGTH: 33
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 96
ggcattaaug agtttgtgag atgttcagga tgg                                33

<210> SEQ ID NO 97
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 97
ggtcttaaug aggtgaagga cacagcg                                       27

<210> SEQ ID NO 98
<211> LENGTH: 31
<212> TYPE: DNA
<213> ORGANISM: Artificial Sequence
<220> FEATURE:
```

```
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 98
gggtttaauc gcagagacta ggacacaagt g                              31

<210> SEQ ID NO 99
<211> LENGTH: 28
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 99
ggacttaaug cggcgatctg tggtagag                                  28

<210> SEQ ID NO 100
<211> LENGTH: 31
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 100
ggcattaaug ccagcatatt caaacccagt c                              31

<210> SEQ ID NO 101
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 101
ggtcttaauc acacaaccaa cctccgatc                                 29

<210> SEQ ID NO 102
<211> LENGTH: 31
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 102
agagcgauat gggttcctta gacaacggtt c                              31

<210> SEQ ID NO 103
<211> LENGTH: 33
<212> TYPE: DNA
<213> ORGANISM: Artificial Sequence
```

```
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 103
tctgcgautc acaaaggaac acttctcaaa acc                               33

<210> SEQ ID NO 104
<211> LENGTH: 32
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 104
agagcgauat gagttcactc tccaacgctt cc                                32

<210> SEQ ID NO 105
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 105
tctgcgautc acatgagagg caggctgtg                                    29

<210> SEQ ID NO 106
<211> LENGTH: 28
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 106
agagcgaugg gttcccttga caatggtt                                     28

<210> SEQ ID NO 107
<211> LENGTH: 32
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 107
tctgcgautt agagaggcac acttcggaga ac                                32

<210> SEQ ID NO 108
<211> LENGTH: 33
<212> TYPE: DNA
```

```
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 108
agagcgauat gagtagttta tcaaatgcca gtc                              33

<210> SEQ ID NO 109
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 109
tctgcgautc acatcaatgg caaggaa                                     27

<210> SEQ ID NO 110
<211> LENGTH: 32
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (11)..(11)
<223> OTHER INFORMATION: u is deoxy

<400> SEQUENCE: 110
agatatacca ugcgtcatgt tgaacatacc gt                               32

<210> SEQ ID NO 111
<211> LENGTH: 34
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: u is deoxy

<400> SEQUENCE: 111
atggctgcut tatgcggtaa ctgtaccaac acca                             34

<210> SEQ ID NO 112
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (10)..(10)
<223> OTHER INFORMATION: u is deoxy

<400> SEQUENCE: 112
atatacatau gagcggtcgt aaaaccttt                                   29

<210> SEQ ID NO 113
<211> LENGTH: 31
```

```
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (10)..(10)
<223> OTHER INFORMATION: u is deoxy

<400> SEQUENCE: 113
atatccaatu ttaatcctct tcttcttgtt c                              31

<210> SEQ ID NO 114
<211> LENGTH: 25
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 114
agagcgauga gacacgttga acaca                                    25

<210> SEQ ID NO 115
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 115
tctgcgautt atgcagttac ggtacca                                  27

<210> SEQ ID NO 116
<211> LENGTH: 26
<212> TYPE: DNA
<213> ORGANISM: Artificial Sequence
<220> FEATURE:
<223> OTHER INFORMATION: Synthetic DNA

<400> SEQUENCE: 116
agagcgaugt ccggtagaaa gacctt                                   26

<210> SEQ ID NO 117
<211> LENGTH: 30
<212> TYPE: DNA
<213> ORGANISM: Artificial Sequence
<220> FEATURE:
<223> OTHER INFORMATION: Synthetic DNA

<400> SEQUENCE: 117
tctgcgautt aatcttcttc ttcttgttcg                               30

<210> SEQ ID NO 118
<211> LENGTH: 31
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
```

<223> OTHER INFORMATION: u is deoxy

<400> SEQUENCE: 118
agagcgauat ggagtttcgc ttgcttatcc t    31

<210> SEQ ID NO 119
<211> LENGTH: 37
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 119
tctgcgautt aattcttctt caactttcc gacttag    37

<210> SEQ ID NO 120
<211> LENGTH: 36
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 120
ggcttaauat gagttcactc tccaacgctt cccatc    36

<210> SEQ ID NO 121
<211> LENGTH: 41
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 121
ggtttaautt acatgagagg caggctgtgg agaaggatag t    41

<210> SEQ ID NO 122
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 122
ggcttaauat gaggcatgtc gagcat    26

<210> SEQ ID NO 123
<211> LENGTH: 31
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 123
ggtttaautt atgccgtgac agttccgaca c                               31

<210> SEQ ID NO 124
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 124
ggcttaauat gtccggacgt aagacg                                    26

<210> SEQ ID NO 125
<211> LENGTH: 31
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 125
ggtttaautt aatcttcctc ctcctgttca a                               31

<210> SEQ ID NO 126
<211> LENGTH: 36
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 126
ggcttaauat ggaattcaga ttgttgatat tggcct                          36

<210> SEQ ID NO 127
<211> LENGTH: 41
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(8)
<223> OTHER INFORMATION: u is deoxy

<400> SEQUENCE: 127
ggtttaautt atttttcgaa ttgtggatga gaccaagcag a                    41

<210> SEQ ID NO 128
<211> LENGTH: 29
<212> TYPE: DNA

```
<213> ORGANISM: Artificial Sequence
<220> FEATURE:
<223> OTHER INFORMATION: Synthetic DNA

<400> SEQUENCE: 128
ggggaccact ttgtacaaga aagctgggt                                    29
```